US010584388B2

(12) United States Patent
Pestova et al.

(10) Patent No.: US 10,584,388 B2
(45) Date of Patent: Mar. 10, 2020

(54) DETECTION OF CHROMOSOMAL ABNORMALITIES ASSOCIATED WITH ENDOMETRIAL CANCER

(71) Applicants: MAYO FOUNDATION FOR MEDICAL EDUCATION AND RESEARCH, Rochester, MN (US); ABBOTT MOLECULAR, Des Plaines, IL (US)

(72) Inventors: Ekaterina Pestova, Glenview, IL (US); Larry E. Morrison, Oro Valley, AZ (US); Jesse S. Voss, Rochester, MN (US); Lisa M. Peterson, Rochester, MN (US); Kevin C. Halling, Rochester, MN (US)

(73) Assignees: Mayo Foundation for Medical Eduction And Research, Rochester, MN (US); Abbott Molecular, Des Plaines, IL (US)

( * ) Notice: Subject to any disclaimer, the term of this patent is extended or adjusted under 35 U.S.C. 154(b) by 177 days.

(21) Appl. No.: 15/072,222

(22) Filed: Mar. 16, 2016

(65) Prior Publication Data
US 2016/0304963 A1   Oct. 20, 2016

Related U.S. Application Data

(63) Continuation of application No. 13/951,209, filed on Jul. 25, 2013, now abandoned, which is a continuation of application No. 13/068,451, filed on May 10, 2011, now abandoned.

(60) Provisional application No. 61/395,303, filed on May 10, 2010.

(51) Int. Cl.
*C12Q 1/6886* (2018.01)
*C12Q 1/6837* (2018.01)
*C12Q 1/6841* (2018.01)

(52) U.S. Cl.
CPC ......... *C12Q 1/6886* (2013.01); *C12Q 1/6837* (2013.01); *C12Q 1/6841* (2013.01); *C12Q 2600/118* (2013.01)

(58) Field of Classification Search
None
See application file for complete search history.

(56) References Cited

U.S. PATENT DOCUMENTS

| 4,227,537 A | 10/1980 | Suciu et al. |
| 5,143,854 A | 9/1992 | Pirrung et al. |
| 5,713,369 A | 2/1998 | Tao et al. |
| 8,211,634 B2 | 7/2012 | DePinho et al. |
| 2004/0248107 A1* | 12/2004 | Sokolova ............ C12O 1/6886 435/6.14 |
| 2007/0059747 A1 | 3/2007 | Bastian et al. |
| 2011/0281263 A1 | 11/2011 | Matthiesen et al. |
| 2012/0065085 A1 | 3/2012 | Pestova et al. |
| 2014/0031254 A1 | 1/2014 | Pestova et al. |

FOREIGN PATENT DOCUMENTS

| WO | WO 93/18186 | 9/1993 |
| WO | WO 96/17958 | 6/1996 |
| WO | WO 96/39154 | 12/1996 |
| WO | WO 97/03211 | 1/1997 |
| WO | WO 2011/142818 | 11/2011 |

OTHER PUBLICATIONS

Guled (Modern Pathology, 2008, 21, 770-778).*
U.S. Office Action dated Mar. 25, 2013 issued in U.S. Appl. No. 13/068,451.
U.S. Office Action dated May 18, 2015 issued in U.S. Appl. No. 13/951,209.
U.S. Final Office Action dated Oct. 16, 2015 issued in U.S. Appl. No. 13/951,209.
PCT Invitation to pay Additional Fees dated Aug. 2, 2011 issued in PCT/US2011/000834 (WO/2011/142818).
PCT International Search Report and Written Opinion dated Oct. 11, 2011 issued in PCT/US2011/000834 (WO/2011/142818).
PCT International Preliminary Report on Patentability and Written Opinion dated Nov. 13, 2012 issued in PCT/US2011/000834 (WO/2011/142818).
European Supplementary Search Report dated Oct. 25, 2013 issued in EP 11 780 917.8.
European Office Action dated Oct. 16, 2014 issued in EP 11 780 917.8.
European Office Action dated Nov. 3, 2015 issued in EP 11 780 917.8.
Altekruse et al. *SEER Cancer Statistics Review, 1975-2007*, National Cancer Institute. Bethesda, MD, http://seer.cancer.gov/csr/1975_2007/, based on Nov. 2009 SEER data submission, posted to the SEER web site, 2010; pp. 1-3.
Baloglu et al. (2001) "Atypical endometrial hyperplasia shares genomic abnormalities with endometrioid carcinoma by comparative genomic hybridization," *Human Pathology* 32(6):615-22.
Bansal et al. (2009) "The molecular biology of endometrial cancers and the implications for pathogenesis, classification, and targeted therapies," *Cancer Control* 16:8-13.
Barringer et al. (1990) "Blunt-end and Single-strand Ligations by *Escherichia coli* Ligase: Influence on an in Vitro Amplification Scheme," *Gene* 89(1):117-122.

(Continued)

*Primary Examiner* — Sarae L Bausch
(74) *Attorney, Agent, or Firm* — Emily M. Haliday; Weaver Austin Villeneuve & Sampson LLP

(57) ABSTRACT

The methods and compositions described herein address the need for diagnostic method that could be offered to women during yearly checkups to allow for early detection, diagnosis and classification, and treatment of endometrial cancer. In addition, these methods and compositions address the current need for improving diagnostic accuracy of biopsy procedures in symptomatic patients.

6 Claims, 27 Drawing Sheets

(56) References Cited

OTHER PUBLICATIONS

Bokhman (1983) "Two pathogenetic types of endometrial carcinoma," *Gynecologic oncology* 15:10-17.
Critchley et al. (2004) "Evaluation of abnormal uterine bleeding: comparison of three outpatient procedures within cohorts defined by age and menopausal status," *Health Technol Assess* 8(34):iii-iv, 1-158.
Crooke et al. (1993) "Antisense Research and Applications," *CRC Press*, Table of Contents, pp. 1-3.
Dafou et al. (2009) "Chromosomes 6 and 18 induce neoplastic suppression in epithelial ovarian cancer cells," *International Journal of Cancer* 124(5):1037-1044.
Del Priore et al. (2001) "Endometrial brush biopsy for the diagnosis of endometrial cancer," *J Reprod Med* 46(5):439-443.
Eckstein (1991) "Oligonucleotides and Analogues," *IRL Press*, Table of Contents, pp. 1-11.
Faruqi et al. (2008) "Mixed mullerian tumor of endometrium: A case study with sixteen DNA probes using fluorescent in situ hybridization," *Cancer Ther.* 6:389-394.
Fles et al. (2010) "Genomic Profile of Endometrial Tumors Depends on Morphological Subtype, Not on Tamoxifen Exposure," *Genes, Chromosomes & Cancer* 49:699-710.
Fodor et al. (1991) "Light-directed, Spatially Addressable Parallel Chemical Synthesis," *Science* 251(4995):767-773.
Furlan et al. (2005) "Allelotypes and fluorescence In situ hybridization profiles of poorly differentiated endocrine carcinomas of different sites," *Clinical Cancer Research* 11:1765-1775.
Grushko et al. (2008) "An exploratory analysis of HER-2 amplification and overexpression in advanced endometrial carcinoma: a Gynecologic Oncology Group study," *Gynecologic Oncology* 108:3-9.
Guatelli et al. (1990) "Isothermal, in Vitro Amplification of Nucleic Acids by a Multienzyme Reaction Modeled after Retroviral Replication," *PNAS* 87(5):1874-1878.
Guido et al. (1995) "Pipelle endometrial sampling. Sensitivity in the detection of endometrial cancer," *J Reprod Med* 40(8):553-555.
Hirasawa et al. (2003) "Unfavorable prognostic factors associated with high frequency of microsatellite instability and comparative genomic hybridization analysis in endometrial cancer," *Clin Cancer Res.* 9(15):5675-82.
Innis et al. (1990) "PCR Protocols—A Guide to Methods and Applications," *Academic Press Inc.*, Table of Contents, pp. 1-8.
Kawasaki et al. (2003) "11q23-24 loss is associated with chromosomal instability in endometrial cancer," *Int J Mol Med.* 12(5):727-731.
Kim et al. (2007) "Analysis of Chromosomal Changes in Serous Ovarian Carcinoma Using High-Resolution Array Comparative Genomic Hybridization: Potential Predictive Markers of Chemoresistant Disease," *Genes, Chromosomes & Cancer* 46:1-9.
Kipp et al. (2008) "Chromosomal alterations detected by fluorescence in situ hybridization in urothelial carcinoma and rarer histologic variants of bladder cancer," *American journal of clinical pathology* 130:552-559.
Kipp et al (2008) "Direct uterine sampling with the Tao brush sampler using a liquid-based preparation method for the detection of endometrial cancer and atypical hyperplasia: a feasibility study," *Cancer* 114(4):228-235.
König et al. (Jul. 1996) "Gain and Loss of Chromosomes 1, 7, 8, 10, 18, and Y in 46 Prostate Cancers," *Human Pathology*, 27(7):720-727.
Kwoh et al (1989) "Transcription-Based Amplification System and Detection of Amplified Human Immunodeficiency Virus Type 1 with a Bead-Based Sandwich Hybridization Format," *PNAS* 86(16):1173-1177.
Landegren et al. (1988) "A ligase-mediated Gene Detection Technique," *Science* 241(4869):1077-1080.
Levan et al. (2006) "Chromosomal alterations in 98 endometrioid adenocarcinomas analyzed with comparative genomic hybridization," *Cytogenet Genome Res.* 115(1):16-22.
Liehr (2004) "Multicolor FISH probe sets and their applications," *Histology and Histopathology* 19:227-237.
Llobet et al. (2009) "Molecular pathology of endometrial carcinoma: practical aspects from the diagnostic and therapeutic viewpoints," *Journal of clinical pathology* 62:777-785.
Maksem (2000) "Performance characteristics of the Indiana University Medical Center endometrial sampler (Tao Brush) in an outpatient office setting, first year's outcomes: recognizing histological patterns in cytology preparations of endometrial brushings," *Diagn Cytopathol* 22(3):186-195.
Mata et al. (1997) "A Hexameric Phosphorothioate Oligonucleotide Telomerase Inhibitor Arrests Growth of Burkitt's Lymphoma Cells in Vitro and in Vivo," *Toxicology and Applied Pharmacology* 144(1):189-197.
Mayr et al. (2006) "Analysis of Gene Amplification and Prognostic Markers in Ovarian Cancer Using Comparative Genomic Hybridization for Microarrays and Immunohistochemical Analysis for Tissue Microarrays," *Am J Clin Pathol.* 126(1):101-109.
Micci et al. (2004) "Genomic Aberrations in Carcinomas of Uterine Corpus," *Genes, Chromosomes & Cancer* 40:229-246.
Milligan et al. (1993) "Current Concepts in Antisense Drug Design," *Journal of Medicinal Chemistry* 36(14):1923-1937.
Morrison et al. (2002) "Labeling Fluorescence In Situ Hybridization Probes for Genomic Targets," *Methods in Molecular Biology* 204:21-40.
Morrison et al. (2006) "HER-2 is an independent prognostic factor in endometrial cancer: association with outcome in a large cohort of surgically staged patients," *J Clin Oncol* 24:2376-2385.
Morrison et al. (2010) "A GOG 210 aCGH study of gain at 1q23 in endometrioid endometrial cancer in the context of racial disparity and outcome," *Genes, Chromosomes & Cancer* 49:791-802.
Muresu et al. (2002) "Chromosomal abnormalities and microsatellite instability in sporadic endometrial cancer," *Eur J Cancer* 38:1802-1809.
Muslumanoglu et al. (2005) "Genetic imbalances in endometrial hyperplasia and endometrioid carcinoma detected by comparative genomic hybridization," *Eur J Obstet Gynecol Reprod Biol.* 120(1):107-114.
Odicino et al. (2008) "HER-2/neu overexpression and amplification in uterine serous papillary carcinoma: comparative analysis of immunohistochemistry, real-time reverse transcription-polymerase chain reaction, and fluorescence in situ hybridization," *Inti Gynecol Cancer* 18:14-21.
O'Toole et al. (2006) "Genome-wide analysis of deoxyribonucleic acid in endometrial cancer using comparative genomic hybridization microarrays," *Int J Gynecol Cancer* 16:834-42.
Peiro et al. (2002) "CAS (Cellular Apoptosis Susceptibility) Gene Expression in Ovarian Carcinoma: Correlation With 20q13.2 Copy Number and Cyclin D1, p53, and Rb Protein Expression," *Am J Clin Pathol.* 118(6): 922-929.
Qian et al. (2010) "Detection of chromosomal anomalies in endometrial atypical hyperplasia and carcinoma by using fluorescence in situ hybridization," *Cancer cytopathology* 118:97-104.
Riben et al. (1997) "Identification of HER-2/neu oncogene amplification by fluorescence in situ hybridization in stage I endometrial carcinoma," *Mod Pathol* 10:823-831.
Saffari et al. (1995) "Amplification and overexpression of HER-2/neu (c-erbB2) in endometrial cancers: correlation with overall survival," *Cancer Research* 55:5693-5698.
Samarnthai et al. (2010) "Molecular profiling of endometrial malignancies," *Obstetrics and gynecology international* Article ID 162363, 16 Pages.
Sambrook (2001) "Molecular Cloning: A Laboratory Manual," *3rd Edition, Cold Spring D Harbor Laboratory*, Table of Contents pp. 1-18.
Samstag (1996) "Synthesis and Properties of New Antisense Oligodeoxynucleotides Containing Benzylphosphonate Linkages," *Antisense and Nucleic Acid Drug Development* 6(3):153-156.
Samuelson et al. (2008) "Recurrent gene amplifications in human type I endometrial adenocarcinoma detected by fluorescence in situ hybridization," *Cancer Genet Cytogenet.* 181(1):25-30.

(56) References Cited

OTHER PUBLICATIONS

Santin et al. (2005) "Amplification of c-erbB2 oncogene: a major prognostic indicator in uterine serous papillary carcinoma," *Cancer* 104:1391-1397.
Schulten et al. (2004) "Overrepresentation of 8q in carcinosarcomas and endometrial adenocarcinomas," *Am J Clin Pathol.* 122(4):546-551.
Shah et al. (1994) "Cytogenetic and FISH analysis of endometrial carcinoma," *Cancer Genetics and Cytogenetics* 73:142-146.
Sonoda et al. (1997) "Detection of DNA gains and losses in primary endometrial carcinomas by comparative genomic hybridization," *Genes Chromosomes & Cancer* 18(2):115-25.
Strauss-Soukup et al. (1997) "Effects of Neutralization Pattern and Stereochemistry on DNA Bending by Methylphosphonate Substitutions," *Biochemistry* 36(29): 8692-8698.
Suehiro et al. (2000) "Genetic aberrations detected by comparative genomic hybridization predict outcome in patients with endometrioid carcinoma," *Genes, Chromosomes & Cancer* 29:75-82.
Suehiro et al. (2008) "Aneuploidy predicts outcome in patients with endometrial carcinoma and is related to lack of CDH13 hypermethylation," *Clin Cancer Res* 14:3354-3361.
Susumu et at. (2005) "Diagnostic clinical application of two-color fluorescence in situ hybridization that detects chromosome 1 and 17 alterations to direct touch smear and liquid-based thin-layer cytologic preparations of endometrial cancers," *Int J Gynecol Cancer* 15:70-80.
Suzuki et al. (1997) "Frequent gains on chromosome aims lq and/or 8q in human endometrial cancer," *Hum Genet.* 100(5-6):629-36.
Tanner et al. (2000) "Frequent Amplification of Chromosomal Region 20q12-q13 in Ovarian Cancer," *Clin Cancer Res.* 6(5):1833-1839.
Tijssen et al. (1993) "Hybridization with Nucleic Acid Probes," *Laboratory Techniques in Biochemistry and Molecular Biology*; Van der VLIET P. C., ed, Elsevier Publisher 24(2):19-78.
Wiklund et al. (2004) "Genetic Analysis of the RNASEL Gene in Hereditary Familial, and Sporadic Prostate Cancer," *Clinical Cancer Res.* 10(21):7150-7156.
Williams et al. (1999) "Fluorescence in situ hybridization analysis of HER-2/neu, c-myc, and p53 in endometrial cancer," *Experimental and molecular pathology* 67:135-143.
Williams et al. (2008) "Factors affecting adequacy of Pipelle and Tao Brush endometrial sampling," *Bjog* 115(8):1028-1036.
Wu et al. (1989) "The Ligation Amplification Reaction (LAR)—Amplification of Specific DNA Sequences Using Sequential Rounds of Template-Dependent Ligation," *Genomics* 4:560-569.
Yang et al. (2000) "Endometrial biopsy using the Tao Brush method. A study of 50 women in a general gynecologic practice," *J Reprod Med* 45(2):109-114.
Canadian Office Action dated Feb. 21, 2017 issued in CA 2,798,190.
Canadian Office Action dated Mar. 7, 2018 issued in CA 2,798,190.
Fouladi et al. (2003) "Clear Cell Ependymoma: A Clinicopathologic and Radiographic Analysis of 10 Patients" *Cancer* 98:2232-44.
Ribeiro et al. (2007) "Relative Copy No. Gain of MYC in Diagnostic Needle Biopsies is an Independent Prognostic Factor for Prostate Cancer Patients" *European Urology* 52: 116-125.
Canadian Office Action dated Feb. 4, 2019 issued in CA 2,798,190.

\* cited by examiner

| FIG. 1A | FIG. 1B | FIG. 1C |

*FIG. 1*

| FIG. 2A-1 | FIG. 2A-2 | FIG. 2A-3 |

*FIG. 2A*

| FIG. 2B-1 | FIG. 2B-2 | FIG. 2B-3 |

*FIG. 2B*

| FIG. 4A | FIG. 4B | FIG. 4C |
| FIG. 4D | FIG. 4E | FIG. 4F |
| FIG. 4G | FIG. 4H | FIG. 4I |

| Sp # | Gr# | Tumor Type | Test or Ref? | Sp # | Age | MYC %gain >4 | CEP18 %gain >4 | 1q24 %gain >6 | 20q13.2 %gain >4 | MAX of 4 | Max /50 | CEP10 %Imba I>12 | CEP10 %loss >10 | FGFR %gain >1 | PTEN %loss >18 |
|---|---|---|---|---|---|---|---|---|---|---|---|---|---|---|---|
| 101 | 1 | Normal | N+Hyper | 101 | Age=64 | 0 | 0 | 0 | 0 | 0 | 0 | 10 | 10 | 0 | 12 |
| 102 | 1 | Normal | N+Hyper | 102 | Age=40 | 0 | 0 | 0 | 0 | 0 | 0 | 6 | 6 | 0 | 6 |
| 103 | 1 | Normal | N+Hyper | 103 | Age=48 | 0 | 0 | 0 | 0 | 0 | 0 | 8 | 8 | 0 | 14 |
| 104 | 1 | Normal | N+Hyper | 104 | Age=47 | 0 | 0 | 0 | 4 | 4 | 2 | 2 | 2 | 0 | 8 |
| 105 | 1 | Normal | N+Hyper | 105 | Age=64 | 0 | 0 | 0 | 0 | 0 | 0 | 6 | 6 | 0 | 18 |
| 106 | 1 | Normal | N+Hyper | 106 | Age=60 | 0 | 0 | 0 | 0 | 0 | 0 | 4 | 4 | 0 | 4 |
| 107 | 1 | Normal | N+Hyper | 107 | Age=83 | 0 | 0 | 0 | 0 | 0 | | | | | |
| 108 | 1 | Normal | N+Hyper | 108 | Age=55 | 0 | 0 | 0 | 0 | 0 | | | | | |
| 109 | 1 | Normal | N+Hyper | 109 | Age=62 | 0 | 0 | 0 | 0 | 0 | | | | | |
| 110 | 1 | Normal | N+Hyper | 110 | Age=38 | 0 | 0 | 0 | 4 | 4 | | | | | |
| 86 | 2 | Simple hyperplasia | N+Hyper | 86 | Age=72 | 0 | 2 | 2 | 0 | 2 | 1 | 26 | 26 | 0 | 28 |
| 88 | 2 | Simple hyperplasia | N+Hyper | 88 | Age=78 | 12 | 6 | 8 | 0 | | 6 | 8 | 8 | 0 | 10 |
| 96 | 2 | Simple hyperplasia | N+Hyper | 96 | Age=50 | 0 | 2 | 2 | 0 | 2 | | | | | |
| 97 | 2 | Simple hyperplasia | N+Hyper | 97 | Age=50 | 0 | 2 | 2 | 4 | 4 | 2 | 10 | 10 | 0 | 14 |
| 100 | 2 | Simple hyperplasia | N+Hyper | 100 | Age=55 | 0 | 0 | 0 | 0 | 0 | 0 | 8 | 8 | 0 | 10 |
| 85 | 3 | Complex hyperplasia | N+Hyper | 85 | Age=68 | 72 | 8 | 6 | 2 | | | | | | |
| 87 | 3 | Complex hyperplasia | N+Hyper | 87 | Age=59 | 2 | 4 | 0 | 2 | 4 | 2 | 2 | 2 | 0 | 6 |
| 89 | 3 | Complex hyperplasia | N+Hyper | 89 | Age=38 | 0 | 2 | 0 | 0 | 2 | 1 | 4 | 4 | 0 | 6 |
| 90 | 3 | Complex hyperplasia | N+Hyper | 90 | Age=52 | 4 | 2 | 2 | 0 | 4 | | | | | |
| 91 | 3 | Complex hyperplasia | N+Hyper | 91 | Age=58 | 0 | 4 | 4 | 0 | 4 | | | | | |
| 93 | 3 | Complex hyperplasia | N+Hyper | 93 | Age=60 | 2 | 2 | 6 | 2 | 6 | | | | | |
| 2 | 4 | Endometrioid Grade Ca | | 2 | Age=58 | 0 | 0 | 0 | 0 | 0 | 0 | 18 | 18 | 2 | 26 |
| 3 | 4 | Endometrioid Grade Ca | | 3 | Age=58 | 58 | 8 | 10 | 4 | | 29 | 18 | 14 | 0 | 18 |
| 4 | 4 | Endometrioid Grade Ca | | 4 | Age=77 | 14 | 8 | 82 | 12 | | 41 | 12 | 8 | 0 | 8 |
| 5 | 4 | Endometrioid Grade Ca | | 5 | Age=79 | 28 | 16 | 38 | 10 | | 19 | 26 | 12 | 24 | 14 |
| 14 | 4 | Endometrioid Grade Ca | | 14 | Age=47 | 56 | 44 | 36 | 16 | | 28 | 26 | 8 | 12 | 10 |
| 15 | 4 | Endometrioid Grade Ca | | 15 | Age=60 | 4 | 4 | 4 | 10 | | 5 | 18 | 18 | 2 | 18 |
| 16 | 4 | Endometrioid Grade Ca | | 16 | Age=64 | 0 | 2 | 4 | 4 | 4 | 2 | 26 | 26 | 4 | 28 |
| 18 | 4 | Endometrioid Grade Ca | | 18 | Age=0 | 8 | 10 | 80 | 0 | | 40 | 8 | 4 | 2 | 4 |
| 56 | 4 | Endometrioid Grade Ca | | 56 | Age=57 | 0 | 4 | 0 | 0 | 4 | 2 | 22 | 22 | 0 | 26 |
| 57 | 4 | Endometrioid Grade Ca | | 57 | Age=58 | 8 | 2 | 2 | 0 | | 4 | 22 | 22 | 0 | 26 |
| 58 | 4 | Endometrioid Grade Ca | | 58 | Age=76 | 2 | 6 | 2 | 12 | | 6 | 26 | 16 | 8 | 16 |
| 59 | 4 | Endometrioid Grade Ca | | 59 | Age=65 | 0 | 0 | 8 | 2 | | 4 | 16 | 16 | 0 | 22 |
| 61 | 4 | Endometrioid Grade Ca | | 61 | Age=81 | 4 | 8 | 6 | 2 | | 4 | 14 | 12 | 0 | 12 |
| 63 | 4 | Endometrioid Grade Ca | | 63 | Age=81 | 8 | 6 | 86 | 2 | | 43 | 14 | 10 | 0 | 14 |
| 65 | 4 | Endometrioid Grade Ca | | 65 | Age=55 | 2 | 6 | 2 | 0 | 6 | 3 | 34 | 34 | 4 | 38 |
| 7 | 5 | Endometrioid Grade Ca | | 7 | Age=69 | 74 | 16 | 8 | 0 | | | | | | |
| 8 | 5 | Endometrioid Grade Ca | | 8 | Age=54 | 14 | 10 | 2 | 4 | | | | | | |
| 33 | 5 | Endometrioid Grade Ca | | 33 | Age=86 | 6 | 14 | 88 | 2 | | | | | | |
| 34 | 5 | Endometrioid Grade Ca | | 34 | Age=70 | 26 | 0 | 2 | 4 | | 13 | 10 | 8 | 52 | 16 |
| 35 | 5 | Endometrioid Grade Ca | | 35 | Age=70 | 18 | 6 | 12 | 2 | | | | | | |
| 36 | 5 | Endometrioid Grade Ca | | 36 | Age=79 | 62 | 28 | 68 | 56 | | | | | | |
| 37 | 5 | Endometrioid Grade Ca | | 37 | Age=54 | 10 | 12 | 70 | 2 | | | | | | |
| 66 | 5 | Endometrioid Grade Ca | | 66 | Age=59 | 14 | 24 | 90 | 10 | | | | | | |
| 67 | 5 | Endometrioid Grade Ca | | 67 | Age=85 | 0 | 0 | 0 | 2 | 2 | | | | | |
| 70 | 5 | Endometrioid Grade Ca | | 70 | Age=60 | 80 | 8 | 12 | 4 | | | | | | |
| 83 | 5 | Endometrioid Grade Ca | | 83 | Age=48 | 28 | 10 | 26 | 12 | | | | | | |
| 9 | 6 | Endometrioid Grade Ca | | 9 | Age=44 | 62 | 18 | 18 | 0 | | | | | | |
| 42 | 6 | Endometrioid Grade Ca | | 42 | Age=77 | 16 | 18 | 82 | 16 | | | | | | |
| 43 | 6 | Endometrioid Grade Ca | | 43 | Age=71 | 80 | 30 | 92 | 10 | | | | | | |
| 44 | 6 | Endometrioid Grade Ca | | 44 | Age=66 | 14 | 12 | 90 | 4 | | | | | | |
| 45 | 6 | Endometrioid Grade Ca | | 45 | Age=42 | 24 | 28 | 32 | 8 | | | | | | |
| 47 | 6 | Endometrioid Grade Ca | | 47 | Age=68 | 98 | 76 | 78 | 80 | | | | | | |
| 75 | 6 | Endometrioid Grade Ca | | 75 | Age=56 | 30 | 18 | 34 | 10 | | | | | | |
| 76 | 6 | Endometrioid Grade Ca | | 76 | Age=59 | 42 | 0 | 28 | 16 | | | | | | |
| 77 | 6 | Endometrioid Grade Ca | | 77 | Age=47 | 82 | 88 | 56 | 44 | | | | | | |
| 1 | 7 | Serous | Ca | 1 | Age=60 | 74 | 50 | 64 | 48 | | | | | | |
| 6 | 7 | Serous | Ca | 6 | Age=92 | 84 | 76 | 84 | 74 | | | | | | |
| 10 | 7 | Serous | Ca | 10 | Age=64 | 94 | 72 | 50 | 50 | | | | | | |
| 49 | 7 | Serous | Ca | 49 | Age=42 | 94 | 100 | 92 | 86 | | | | | | |
| 50 | 7 | Serous | Ca | 50 | Age=76 | 62 | 22 | 64 | 34 | | | | | | |
| 51 | 7 | Serous | Ca | 51 | Age=80 | 92 | 66 | 84 | 98 | | | | | | |
| 79 | 7 | Serous | Ca | 79 | Age=77 | 62 | 30 | 64 | 82 | | | | | | |
| 80 | 7 | Serous | Ca | 80 | Age=87 | 96 | 42 | 84 | 98 | | | | | | |
| 94 | 7 | Serous | Ca | 94 | Age=59 | 84 | 70 | 78 | 18 | | | | | | |
| 11 | 8 | Carcinosarcoma/MMM | Ca | 11 | Age=86 | 90 | 2 | 6 | 56 | | | | | | |
| 12 | 8 | Carcinosarcoma/MMM | Ca | 12 | Age=68 | 76 | 12 | 56 | 66 | | | | | | |
| 78 | 8 | Carcinosarcoma/MMM | Ca | 78 | Age=67 | 90 | 52 | 86 | 60 | | | | | | |
| 54 | 9 | Clear cell | Ca | 54 | Age=75 | 94 | 22 | 92 | 88 | | | | | | |
| 81 | 9 | Clear cell | Ca | 81 | Age=84 | 94 | 60 | 90 | 42 | | | | | | |
| | | | | | Total | 42 | 41 | 38 | 29 | | | 14 | 12 | 9 | 7 |

*FIG. 10*

DETECTION OF CHROMOSOMAL ABNORMALITIES ASSOCIATED WITH ENDOMETRIAL CANCER

CROSS-REFERENCE TO RELATED APPLICATIONS

This application is a continuation of U.S. application Ser. No. 13/951,209, filed Jul. 25, 2013, which is a continuation of U.S. application Ser. No. 13/068,451, filed May 10, 2011, which claims the benefit of U.S. provisional application No. 61/395,303, filed May 10, 2010, which are hereby incorporated by reference in their entireties.

FIELD OF THE INVENTION

The present invention relates generally to the area of detecting, diagnosing, and monitoring of endometrial hyperplasia and carcinoma.

BACKGROUND OF THE INVENTION

Uterine cancer is the fourth most common malignancy diagnosed in women in the United States (estimated 42,793 cases in 2009) and is the seventh most common cause of cancer death among U.S. women. Over 95% of all uterine cancers are cancers of the endometrium (lining of the body of the uterus). Lifetime probability of developing cancer of the uterus is 1 in 40 (U.S.). 35-50% of women ages 35-70 present with one or more risk factors for endometrial cancer.

Two different clinicopathologic subtypes are recognized based on light microscopic appearance, clinical behavior, and epidemiology: the estrogen-related (type I, endometrioid) and the non-estrogen-related types (type II, nonendometrioid such as papillary serous and clear cell). Despite it aggressiveness, endometrial cancer is difficult to diagnose, thus many patients present with symptoms of the late-stage cancer.

SUMMARY OF THE INVENTION

In particular embodiments, the present invention provides a method of detecting the presence of endometrial carcinoma in a biological sample from a subject. The method entails contacting the sample with one or more probes for one or more chromosome regions selected from the group consisting of: 1q, 2p, 2q, 3p, 3q, 7p, 8p, 8q, 9p, 9q, the centromeric region of chromosome 10, 10q, 15q, 16q, 17p, the centromeric region of chromosome 18, 18q, 19p, 20q, and 22q. The one or more probes are incubated with the sample under conditions in which each probe binds selectively with a polynucleotide sequence on its target chromosome or chromosomal region to form a stable hybridization complex. Hybridization of the one or more probes is detected, wherein a hybridization pattern showing at least one gain or loss or imbalance at a chromosomal region targeted by the probes is indicative of endometrial carcinoma.

In certain embodiments, a hybridization pattern showing a gain in one or more chromosome regions selected from the group consisting of: 1q, 2p, 3q, 8q, 10q, and 20q is indicative of endometrial carcinoma. In specific embodiments, a hybridization pattern showing a gain in one or more chromosome regions selected from the group consisting of: 1q, 10p, and 10q is indicative of endometrioid carcinoma. In other specific embodiments, a hybridization pattern showing a gain in one or more chromosome regions selected from the group consisting of: 3q, 8q, 18q, and 20q is indicative of non-endometrioid carcinoma. In an illustrative embodiment, a hybridization pattern showing a gain in 1q31-qtel is indicative of endometrial carcinoma.

In certain embodiments, a hybridization pattern showing a loss in one or more chromosome regions selected from the group consisting of: 9p, 9q, 15q, 16q, 17p, 18q, 19p, and 22q is indicative of endometrial carcinoma. In illustrative embodiments, a hybridization pattern showing a loss in one or more chromosome regions selected from the group consisting of: 15q11-q13, 18q21, and 19ptel is indicative of endometrial carcinoma.

In certain embodiments, the one or more probes are for one or more chromosome subregions selected from the group consisting of: 1q25, 2p24, 2q26, 3p21, 3q27-q29, 7p21, 8p11, 8q24, 9q34, the centromeric region of chromosome 10, 10q23, 10q26, 15q11-q13, 16q24, the centromeric region of chromosome 18, 18q21, 20q12 and 20q13.

In particular embodiments, the sample is contacted with a combination of at least 3 probes for a set of chromosome subregions selected from the group consisting of:
1q25, 8q24, 15q11-q13;
1q25, 10q26, 15q11-q13;
1q25, 2p24, 8q24
1q25, 8q24, 10q26;
1q25, 8p11, 15q11-q13;
1q25, 2p24, 8p11;
1q25, 8p11, 10q26;
1q25, 8p11, 8q24;
1q25, 2p24, 10q26;
1q25, 2p24, 15q11-q13;
8q24, 10q26, 15q11-q13;
1q25, 8p11, 20q13;
1q25, 8q24, 20q13;
1q25, 15q11-q13, 20q13;
1 q25, 10q26, 20q13;
8p11, 10q26, 15q11-q13;
1q25, 2p24, 20q13;
2p24, 8p11, 10q26;
2p24, 8q24, 10q26;
2p24, 10q26, 15q11-q13;
2p24, 8q24, 15q11-q13;
10q26, 15q11-q13, 20q13;
1q25, 8p11, 18q21;
1q25, 8q24, 18q21;
1q25, 10q26, 18q21;
1q25, 15q11-q13, 18q21;
8p11, 8q24, 10q26;
8q24, 10q26, 20q13;
1q25, 2p24, 18q21;
2p24, 8p11, 8q24;
2p24, 8p11, 15q11-q13;
8p11, 8q24, 15q11-q13;
2p24, 10q26, 20q13;
8p11, 10q26, 20q13;
2p24, 8p11, 20q13;
2p24, 8q24, 20q13;
8q24, 15q11-q13, 20q13; and
8p11, 15q11-q13, 20q13.

In certain embodiments, the sample is contacted with a combination of at least 3 probes for a set of chromosome subregions selected from the group consisting of:
1q25, 18q21, CEP18, 8q24;
2p24, 2q26, 10q26, 2q13; and
10q23, CEP10, and 8p11.

In particular embodiments, the sample is contacted with a combination of at least 2 probes for a set of chromosome subregions selected from the group consisting of:

18q21, 1q24, 8q24, CEP18;
1q24, 8q24, 10q26, CEP18;
18q21, 1q24, 10q26, CEP18;
1q24, 8q24, CEP18, 3q27-q29;
18q21, 1q24, 8q24, 10q26;
1q24, 2p24, 10q26, CEP18;
1q24, 10q26, CEP18, 3q27-q29;
1q24, 10q26, CEP18, 20q13;
1q24, CEP18, 3q27-q29, 20q13;
1q24, 2p24, CEP18, 3q27-q29;
18q21, 1q24, 10q26, 20q13;
1q24, 8q24, CEP18;
18q21, 1q24, CEP18; and
1q24, CEP18.

In illustrative embodiments, the sample is contacted with a combination of at least 4 probes for a set of chromosome subregions selected from the group consisting of:

1q24, 8q24, CEP18, 20q13;
1q24, CEP18, 3q27-q29, 20q13;
1q24, CEP18, 20q13, 10q26;
CEP10, 8q24, CEP18, 1q24;
10q26, CEP10, 1q24, 8q24;
8q24, 1q24, 20q13, CEP18; 10q26;
20q13, CEP10, 1q24, 10q26, wherein a hybridization pattern showing a gain in one or more of these chromosome subregions is indicative of endometrial carcinoma.

In specific embodiments, one or more of a gain at one of more of 1q24, 8q24, CEP18, and 20q13 are indicative of endometrial carcinoma. In alternative specific embodiments, one or more of a 20q13 gain, a 1q24 gain, a CEP10 imbalance, and a 10q26 gain are indicative of endometrial carcinoma.

In particular embodiments, the sample is contacted with a combination of at least 2 probes for a set of chromosome subregions selected from the group consisting of:

18q21, 1q25, 8q24, CEP18;
1q25, 8q24, 10q26, CEP18;
18q21, 1q25, 10q26, CEP18;
1q25, 8q24, CEP18, 3q27-q29;
18q21, 1q25, 8q24, 10q26;
1q25, 2p24, 10q26, CEP18;
1q25, 10q26, CEP18, 3q27-q29;
1q25, 10q26, CEP18, 20q13;
1q25, CEP18, 3q27-q29, 20q13;
1q25, 2p24, CEP18, 3q27-q29;
18q21, 1q25, 10q26, 20q13;
1q25, 8q24, CEP18;
18q21, 1q25, CEP18; and
1q25, CEP18.

In illustrative embodiments, the sample is contacted with a combination of at least 4 probes for a set of chromosome subregions selected from the group consisting of:

1q25, 8q24, CEP18, 20q13;
1q25, CEP18, 3q27-q29, 20q13;
1q25, CEP18, 20q13, 10q26;
CEP10, 8q24, CEP18, 1q25;
10q26, CEP10, 1q25, 8q24;
8q24, 1q25, 20q13, CEP18; 10q26;
20q13, CEP10, 1q25, 10q26, wherein a hybridization pattern showing a gain in one or more of these chromosome subregions is indicative of endometrial carcinoma.

In specific embodiments, one or more of a gain at one of more of 1q25, 8q24, CEP18, and 20q13 are indicative of endometrial carcinoma. In alternative specific embodiments, one or more of a 20q13 gain, a 1q25 gain, a CEP10 imbalance, and a 10q26 gain are indicative of endometrial carcinoma.

In variations of any of the preceding embodiments, the probe combination can distinguish samples including endometrial carcinoma from samples that do not include endometrial carcinoma with a sensitivity of at least 93% and a specificity of at least 90%. For example, the sensitivity can be at least 95% and the specificity can be at least 90.4%. In specific embodiments, the sensitivity is least 96% and the specificity is at least 91%.

In variations of any of the preceding embodiments, the probe combination can include between 2 and 10 probes. In particular embodiments, the probe combination includes between 3 and 8 probes. In an illustrative embodiment, the probe combination includes 4 probes.

In any of preceding embodiments, the method can be carried out by array comparative genomic hybridization (aCGH) to probes immobilized on a substrate. Alternatively, the method can be carried out by fluorescence in situ hybridization, and each probe in the probe combination can be labeled with a different fluorophore.

In any of the preceding embodiments, the sample can be an endometrial brushing specimen or an endometrial biopsy specimen.

In any of the preceding claims, when the results of the method indicate endometrial carcinoma, the method can additionally include treating the subject for endometrial carcinoma.

The invention also provides, in certain embodiments, a combination of probes including between 2 and 10 probes selected from any of the groups set forth above, wherein the combination of probes has a sensitivity of at least 93% and a specificity of at least 90% for distinguishing samples including endometrial carcinoma from samples that do not include endometrial carcinoma. In particular embodiments, the combination of probes has a sensitivity of at least 95% and a specificity of at least 90.4%. In illustrative embodiments, the combination of probes has a sensitivity of at least 96% and a specificity of at least 91%. In various embodiments, the probe combination includes between 3 and 8 probes, e.g., 4 probes.

Another aspect of the invention includes a kit for diagnosing endometrial carcinoma, wherein the kit includes a combination of probes including between 2 and 10 probes selected from any of the groups set forth above, wherein the combination of probes has a sensitivity of at least 93% and a specificity of at least 90% for distinguishing samples including endometrial carcinoma from samples that do not include endometrial carcinoma. In particular embodiments, the combination of probes has a sensitivity of at least 95% and a specificity of at least 90.4%. In illustrative embodiments, the combination of probes has a sensitivity of at least 96% and a specificity of at least 91%. In various embodiments, the probe combination includes between 3 and 8 probes, e.g., 4 probes.

In various embodiments, a chromosomal gain, loss, or imbalance detected by at least 2, 3, 4, 5, 6, 7, 8, 9, or 10 probes is indicative of endometrial carcinoma.

BRIEF DESCRIPTION OF THE DRAWINGS

FIG. 10: Evaluation of additional probes to improve sensitivity of endometrial cancer detection.

DETAILED DESCRIPTION

Figure 1A:
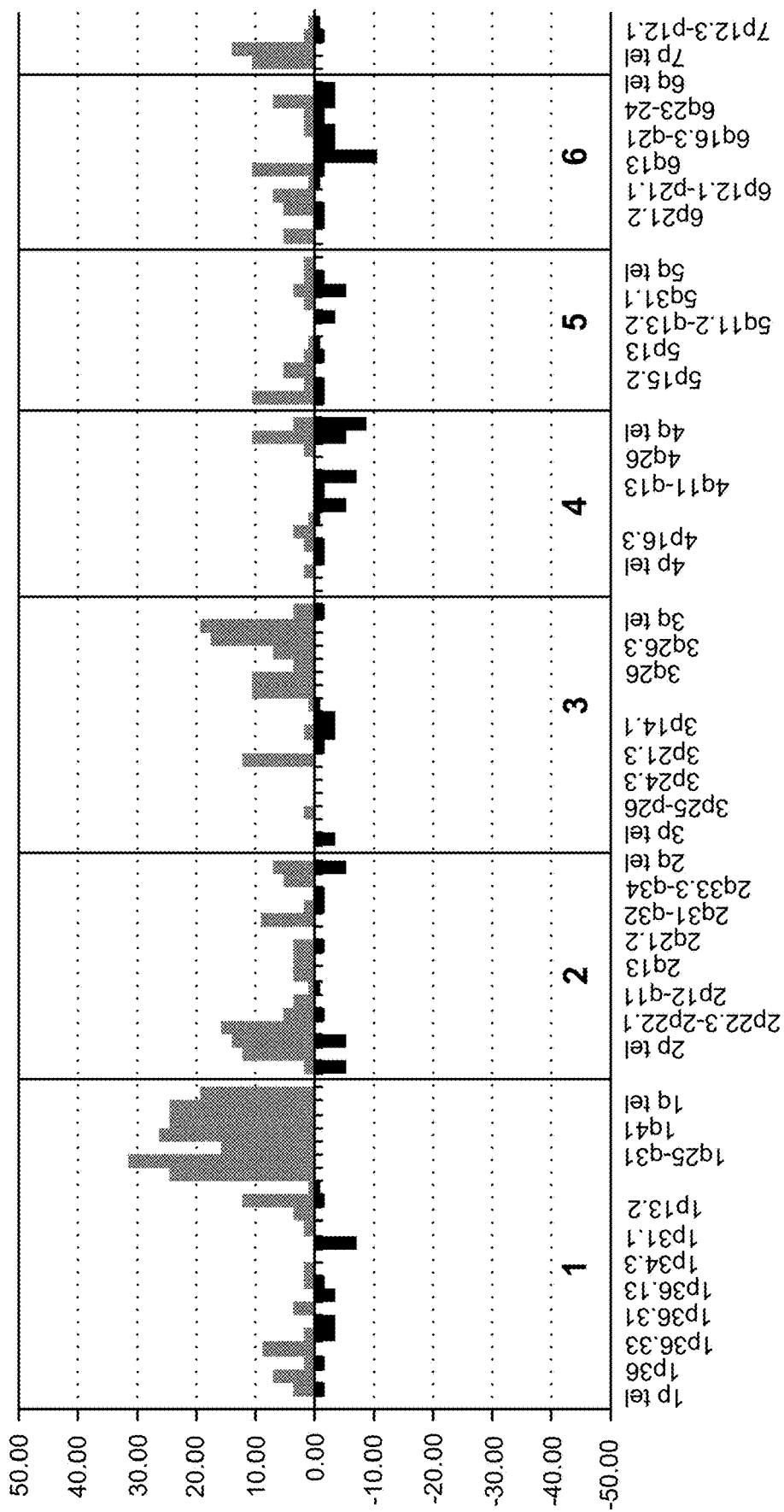
FIG. 1A-C: The frequency of genomic changes in all cancers from CGH data. A, 1ptel-7p12.3-p12.1; B, 7q11.23-15qtel; C, 16ptel-22qtel.
Figure 1B:
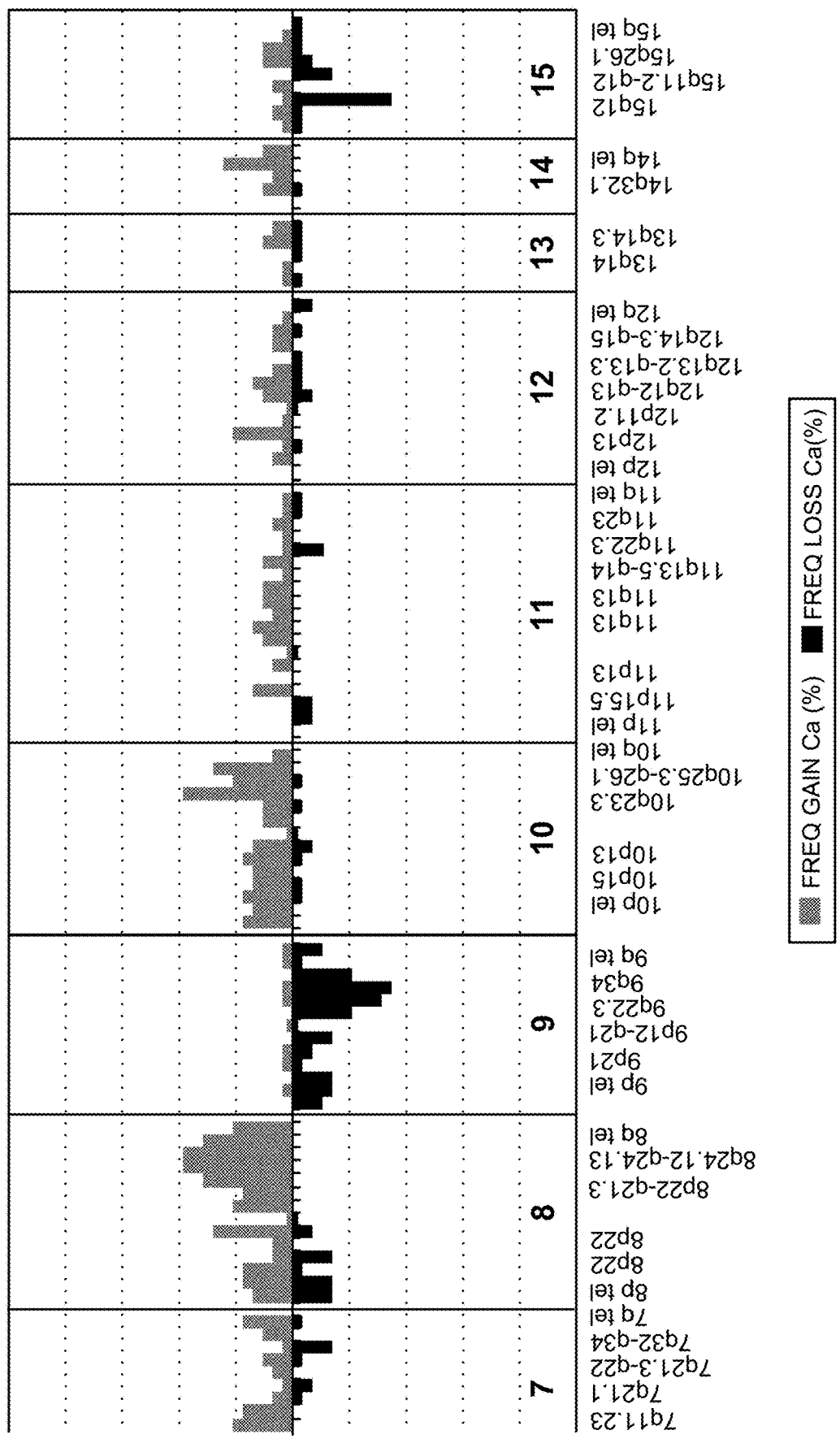
Figure 1C:
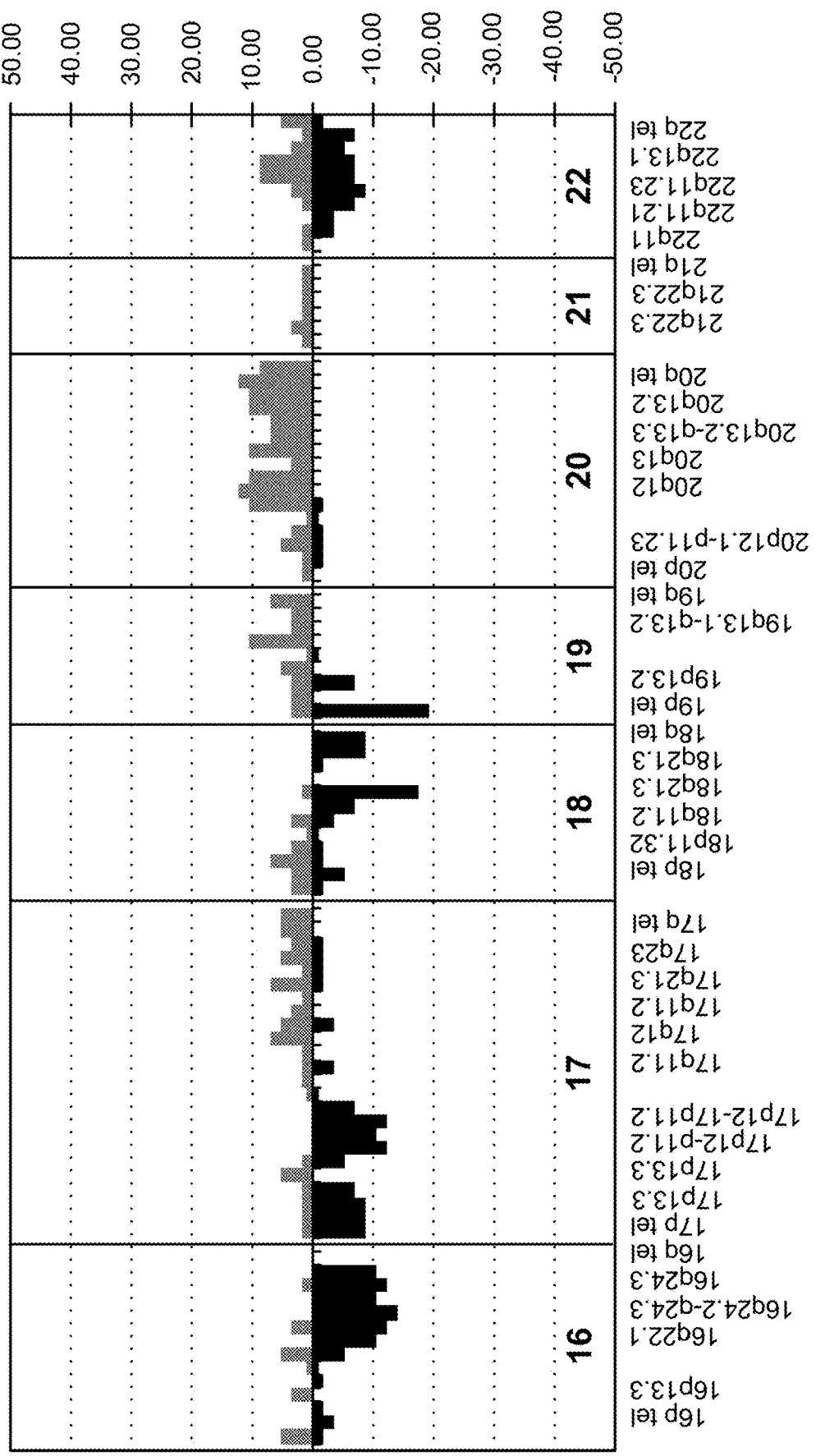

The present invention provides a method of detection of chromosomal abnormalities associated with endometrial carcinoma of both endometrioid and non-endometrioid types, as well as probe combinations and diagnostic kits. The methods can utilize techniques known as Comparative Genomic Hybridization on a microarray (aCGH) and in situ hybridization (e.g., Fluorescence In Situ Hybridization (FISH)) using a combination of Locus Specific Identifier (LSI) and Chromosome Enumerator (CEP) probes to detect cells that have chromosomal abnormalities consistent with a diagnosis of endometrial cancer. The methods described herein can be used to detect endometrial cancer in various types of specimens (e.g., endometrial brushing specimen or endometrial biopsy specimen) obtained in the doctors office or operating room.

There is currently no cytological diagnostic test for the early detection of endometrial cancer available today, and there is no test or procedure to routinely screen women at risk for endometrial cancer. Endometrial biopsy is recommended as the initial evaluation of women with abnormal uterine bleeding. The disadvantages of biopsy are that it an invasive and uncomfortable procedure for the patient. Moreover, tumors comprising <50% of the endometrium may be inadequately sampled by endometrial biopsy. Inadequate sampling by biopsy may result in false negative results and necessitate additional endometrial biopsies to determine the cause of persistent abnormal uterine bleeding. As endometrial cancers are relatively fast growing, patients often present after the cancers have already developed and spread locally.

Conventional cytology collected with an endometrial sampling device such as the Tao brush offers the advantage of being relatively non-invasive and therefore more comfortable for the patient. In addition, endometrial sampling for cytology is less likely than biopsy to result in false negative results due to inadequate sampling. The problem with conventional cytology is that most pathologists do not have experience with interpreting endometrial cytology and many consider it difficult to interpret. Furthermore, even experienced cytopathologists find that there are significant fraction of cases that cannot be definitely diagnosed as either positive or negative for cancer and which must be categorized as indeterminate for the presence of cancer.

The methods and compositions described herein will provide means for screening and improved diagnosis of endometrial cancer. Specifically, the methodology described herein can provide one or more of the following benefits: distinguish cancer from difficult benign conditions; distinguish benign tissue from pre-cancerous lesions and pre-cancerous lesions from cancer; distinguish endometrioid and non-endometrioid tumors; provide an early screening tool for outpatient tests on cytology specimens; aid in diagnosis of endometrial cancer in biopsy or surgical specimens (aid histological tissue evaluation); and provide an aid in monitoring of cancer and pre-cancerous conditions during therapy.

Advantages of the methods described herein can include one or more of the following: use of stable DNA for detection of chromosomal abnormalities (deletion, amplification, aneusomy, translocation); rapid detection: results could be obtained in 18-36 hours; implementation possibilities include multiplexed methods (e.g., microarray) and multicolor FISH; use as stand-alone test or as adjuncts to other tests (histology, PSA, nomogram, methylation, mutation); use on cytology specimens or biopsy (fresh-frozen or FFPE); combination of several probes increases sensitivity and specificity as compared to a single-analyte assay; increased sensitivity compared to conventional cytology.

Definitions

Terms used in the claims and specification are defined as set forth below unless otherwise specified.

The term "endometrial carcinoma" refers to a malignant neoplasm of the endometrium, which is the mucous membrane lining the uterus. Two different clinicopathologic subtypes are recognized based on light microscopic appearance, clinical behavior, and epidemiology: the estrogen-related (type I, "endometrioid") and the non-estrogen-related types (type II, "nonendometrioid", such as papillary serous and clear cell).

The terms "tumor" or "cancer" in an animal refer to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. The term tumor includes both benign and malignant neoplasms. The term "neoplastic" refers to both benign and malignant atypical growth.

The term "biological sample" or "specimen" is intended to mean a sample obtained from a subject suspected of having, or having endometrial carcinoma. In some embodiments, the sample includes a formalin-fixed paraffin-embedded biopsy. In addition to subjects suspected of having endometrial carcinoma, the biological sample may further be derived from a subject that has been diagnosed with endometrial carcinoma for confirmation of diagnosis or establishing that all of the tumor was removed ("clear margin"). The sample may be derived from a endometrial brushing specimen or endometrial biopsy specimen.

The terms "nucleic acid" or "polynucleotide," as used herein, refer to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzyl-phosphonate linkages (Samstag (1996) Antisense Nucleic Acid Drug Dev 6: 153-156).

The terms "hybridizing specifically to," "specific hybridization," and "selectively hybridize to," as used herein, refer to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization (e.g., as in array, Southern or Northern hybridization, or FISH) are sequence-dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, N.Y., and detailed discussion, below).

A "chromosomal probe" or "chromosomal probe composition" refers to one or more polynucleotides that specifically hybridize to a region of a chromosome. The target sequences to which the probe can bind vary in length, e.g., from about 25,000 nucleotides to about 800,000 nucleotides. Smaller probes, e.g., that hybridize to a region of less than 100,000 nucleotides, or to a region of less than 10,000 nucleotides, can also be employed. Thus, in various embodiments, the probe can hybridize target sequences that are 25,000 nucleotides, 30,000 nucleotides, 50,000 nucleotides, 100,000 nucleotides, 150,000 nucleotides, 200,000 nucleotides, 250,000 nucleotides, 300,000 nucleotides, 350,000 nucleotides, 400,000 nucleotides, 450,000 nucleotides, 500,000 nucleotides, 550,000 nucleotides, 600,000 nucleotides, 650,000 nucleotides, 700,000 nucleotides, 750,000 nucleotides, or 800,00 nucleotides in length or that have a length falling in any range having any of these values as endpoints. A probe to a particular chromosomal region can include multiple polynucleotide fragments, e.g., ranging in size from about 50 to about 1,000 nucleotides in length.

A chromosome enumeration probe (CEP) is any probe able to enumerate the number of specific chromosomes in a cell.

The term "label containing moiety" or "detection moiety" generally refers to a molecular group or groups associated with a chromosomal probe, either directly or indirectly, that allows for detection of that probe upon hybridization to its target.

The term "target region" or "nucleic acid target" refers to a nucleotide sequence that resides at a specific chromosomal location whose loss and/or gain is indicative of the presence of endometrial carcinoma.

Introduction

The methods described herein are based, in part, on the identification of highly sensitive and specific chromosomal probe combinations that can be used to selectively detect endometrial carcinoma. The probe combinations provide higher sensitivity and specificity than individual probes. The probes encompass locus-specific probes as well as chromosome enumeration probes (CEPs), which typically hybridize to centromeric regions. The methods are carried by hybridizing one or more probes to nucleic acids from, e.g., cytology specimens (uterine brushings, washings, swabs) or cells from frozen specimens or fixed specimens, such as formalin-fixed, paraffin-embedded tissue.

Chromosomal Probes

Probes for use in the invention are used for hybridization to nucleic acids that are present in biological samples from subjects where there is some degree of suspicion of endometrial carcinoma. In certain embodiments, the probes are labeled with detectable labels, e.g., fluorescent labels.

Chromosome Enumeration Probe

A chromosome enumeration probe typically recognizes and binds to a region near to (referred to as "peri-centromeric") or at the centromere of a specific chromosome, typically a repetitive DNA sequence. The centromere of a chromosome is typically considered to represent that chromosome entity since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals for the corresponding centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome.

In lieu of a centromeric probe for a chromosome, one of skill in the art will recognize that a chromosomal arm probe may alternately be used to approximate whole chromosomal loss or gain. However, such probes are not as accurate at enumerating chromosomes since the loss of signals for such probes may not always indicate a loss of the entire chromosomes. Examples of chromosome enumeration probes include CEP® probes (e.g., CEP® 12 and X/Y probes) commercially available from Abbott Molecular, DesPlaines, Ill. (formerly Vysis, Inc., Downers Grove, Ill.).

Chromosome enumerator probes and locus-specific probes that target a chromosome region or subregion can readily be prepared by those in the art or can be obtained commercially, e.g., from Abbott Molecular, Molecular Probes, Inc. (Eugene, Oreg.), or Cytocell (Oxfordshire, UK). Such probes are prepared using standard techniques. Chromosomal probes may be prepared, for example, from protein nucleic acids, cloned human DNA such as plasmids, bacterial artificial chromosomes (BACs), and P1 artificial chromosomes (PACs) that contain inserts of human DNA sequences. A region of interest may be obtained via PCR amplification or cloning. Alternatively, chromosomal probes may be prepared synthetically.

Locus-Specific Probes

Probes that can be used in the method described herein include probes that selectively hybridize to chromosome regions (e.g., 1q, 2p, 2q, 3p, 3q, 7p, 8p, 8q, 9p, 9q, 10q, 15q, 16q, 17p, 18q, 19p, 20q, and 22q) or subregions of the chromosome regions (e.g., 1q25, 2p24, 2q26, 3p21, 3q27-q29, 7p21, 8p11, 8q24, 9q34, 10q23, 10q26, 15q11-q13, 16q24, 18q21, 20q12 and 20q13). (The subregion designations as used herein include the designated band and typically about 10 megabases of genomic sequence to either side.) Such probes are also referred to as "locus-specific probes." A locus-specific probe selectively binds to a specific locus at a chromosomal region that is known to undergo gain or loss in endometrial carcinoma. A probe can target coding or non-coding regions, or both, including exons, introns, and/or regulatory sequences, such as promoter sequences and the like.

When targeting of a particular gene locus is desired, probes that hybridize along the entire length of the targeted gene are preferred in some embodiments, although not required. In specific embodiments, a locus-specific probe can be designed to hybridize to an oncogene or tumor suppressor gene, the genetic aberration of which is correlated with endometrial carcinoma.

Probes useful in the methods described herein generally include a collection of one or more nucleic acid fragments whose hybridization to a target can be detected. Probes can be produced from a source of nucleic acids from one or more particular (preselected) portions of the genome, for example one or more clones, an isolated whole chromosome or chromosome fragment, or a collection of polymerase chain reaction (PCR) amplification products. Probes useful in the method described herein can be produced from nucleic acids found in the regions described herein. The probe may be processed in some manner, for example, by blocking or removal of repetitive nucleic acids or enrichment with unique nucleic acids.

In certain embodiments, e.g., in in situ hybridization (e.g., FISH)-based embodiments, locus-specific probe targets preferably include at least 100,000 nucleotides. For cells of a given sample, relative to those of a control, increases or decreases in the number of signals for a probe indicate a gain or loss, respectively, for the corresponding region.

Probes may also be employed as isolated nucleic acids immobilized on a solid surface (e.g., nitrocellulose), as in aCGH. In some embodiments, the probes may be members of an array of nucleic acids as described, for instance, in WO 96/17958, which is hereby incorporated by reference it its entirety and specifically for its description of array CGH. Techniques capable of producing high density arrays are well-known (see, e.g., Fodor et al. Science 767-773 (1991) and U.S. Pat. No. 5,143,854), both of which are hereby incorporated by reference for this description.

As described in detail below, loci that were putatively associated with endometrial cancer were identified and the sensitivity and specificity of this association was examined in detail using array Comparative Genomic Hybridization (aCGH) and Fluorescence In Situ Hybridization (FISH). The clones selected from aCGH analysis included: LAMC2 (1q25-q31), MYCN (2p24.1), RASSF (3p21.3), TP63 (3q27-q29), IL6 (7p21), FGFR1 (8p11.2-p11.1), MYC (8q24), TSC1 (9q34), PTEN (10q23.3), FGFR2 (10q26), UBE3A/D15S10 (15q11-q13), FANCA (16q24.3), DCC (18q21.3), NCOA3 (20q12), and ZNF217 (20q13.2). The probes in FISH analysis included: 1q25, PTEN (10q23.3), DCC (18q21.2), CEP10, CEP18, FGFR1 (8p11.2), MYC (8q24), MYCN (2p24.3), PIK3CA (2q26.32), FGFR2 (10q26.13), and ZNF217 (20q13.2). New FISH probes were developed for NMYC, FGFR1, and FGFR2.

Probe Selection Methods

Probe combinations can be selected for their ability to simply detect endometrial carcinoma, but are typically selected for the ability to discriminate between endometrial carcinoma and other conditions. Thus, analyses of probe combinations are typically performed to determine the DFI values of different probe combinations for discriminating between endometrial carcinoma and other conditions or normal tissue. In particular embodiments, probe combinations can be analyzed to discriminate between endometrioid and non-endometrioid types of endometrial carcinoma.

Probe combinations for use in the methods of the present invention can be selected using the principles described in the examples. Combinations of chromosomal probes within a probe combination are chosen for sensitivity, specificity, and detectability regarding endometrial carcinoma. Sensitivity refers to the ability of a test (e.g. FISH) to detect disease (e.g. endometrial carcinoma) when it is present. More precisely, sensitivity is defined as True Positives/(True Positives+False Negatives). A test with high sensitivity has few false negative results, while a test with low sensitivity has many false negative results. In particular embodiments, the combination of probes has a sensitivity of least about: 93, 94, 95, 96, 97, 98, 99, or 100%, or a sensitivity falling in a range with any of these values as endpoints.

Specificity, on the other hand, refers to the ability of test (e.g. FISH) to give a negative result when disease is not present. More precisely, specificity is defined as True Negatives/(True Negatives+False Positives). A test with high specificity has few false positive results, while a test with a low specificity has many false positive results. In certain embodiments, the combination of probes has a specificity of at about: 88, 89, 90, 91, 92, 93, 94, or 95%, or a specificity falling in a range with any of these values as endpoints.

In general, chromosomal probe combinations with the highest combined sensitivity and specificity for the detection of endometrial carcinoma are preferred. In exemplary embodiments the combination of probes has a sensitivity and specificity of at least about: 93% and 88%, 95% and 90%, 96% and 91%, 97% and 92%, respectively, or any combination of sensitivity and specificity based on the values given above for each of these parameters.

The combined sensitivity and specificity of a probe combination can be represented by the parameter distance from ideal (DFI), defined as $[(1\text{-sensitivity})^2+(1\text{-specificity})^2]^{1/2}$ DFI values range from 0 to 1.414, with 0 representing a probe combination having 100% sensitivity and 100% specificity and 1.414 representing a probe combination with 0% sensitivity and 0% specificity.

There is no limit to the number of probes that can be employed in a combination, although, in certain embodiments, no more than ten probes are combined. Additionally, in some embodiments, the number of probes within a set that is to be viewed by a human observer (and not with computer assisted imaging techniques) may be restricted for practical reasons, e.g., by the number of unique fluorophores that provide visually distinguishable signals upon hybridization. For example, typically four or five unique fluorophores (e.g., which appear as red, green, aqua, and gold signals to the human eye) can be conveniently employed in a single probe combination. Generally, the sensitivity of an assay increases as the number of probes within a set increases. However, the increases in sensitivity become smaller and smaller with the addition of more probes and at some point the inclusion of additional probes to a probe combination is not associated with significant increases in the sensitivity of the assay ("diminishing returns"). Increasing the number of probes in a probe combination may decrease the specificity of the assay. Accordingly, a probe combination of the present invention typically includes two, three, or four chromosomal probes, as necessary to provide optimal balance between sensitivity and specificity.

Individual probes can be chosen for inclusion in a probe combination based on their ability to complement other probes within the combination. Specifically, they are targeted to chromosomes or chromosomal subregions that are not frequently altered simultaneously within a given endometrial carcinoma. Thus, each probe in a probe combination complements the other(s), i.e., identifies endometrial carcinoma where the other probes in the combination sometime fail to identify. One method for determining which probes complement one another is to identify single probes with the lowest DFI values for a group of tumor specimens. Then additional probes can be tested on the tumor samples that the initial probe failed to identify, and the probe with the lowest DFI value measured in combination with the initial probe(s) is added to the set. This may then be repeated until a full set of chromosomal probes with the desired DFI value is achieved.

Discrimination analysis is one method that can be used to determine which probes are best able to detect endometrial carcinoma. This method assesses if individual probes are able to detect a statistically different percentage of abnormal cells in test specimens (e.g., endometrial carcinoma) when compared to normal specimens. The detection of cells with chromosomal (or locus) gains or chromosomal (or locus) losses can both be used to identify neoplastic cells in endometrial carcinoma patients. However, chromosomal losses sometimes occur as an artifact in normal cells because of random signal overlap and/or poor hybridization. In sections of formalin-fixed paraffin-embedded material, commonly used to assess biopsies, truncation of nuclei in the sectioning process can also produce artifactual loss of chromosomal material. Consequently, chromosomal gains are often a more reliable indicator of the presence of neoplastic cells.

Cutoff values for individual chromosomal gains and losses must be determined when choosing a probe combination. The term "cutoff value" is intended to mean the value of a parameter associated with chromosomal aberration that divides a population of specimens into two groups—those specimens above the cutoff value and those specimens below the cutoff value. For example, the parameter may be the absolute number or percentage of cells in a population that have genetic aberrations (e.g., losses or gains for target regions). If the number or percentage of cells in the specimen harboring losses or gains for a particular probe is higher than the cutoff value, the sample is determined to be positive for endometrial carcinoma.

Useful probe combinations are discussed in detail in the Example below. In exemplary combinations, one or more of a gain at one of more of 1q24, 8q24, CEP18, and 20q13 are indicative of endometrial carcinoma, as are (i) one or more of a gain at one of more of 1q25, 8q24, CEP18, and 20q13 and (ii) one or more of a 20q13 gain, a 1q24 gain, a CEP10 imbalance, and a 10q26 gain. Also of note are that different genomic changes were observed when comparing endometrioid and non-endometrioid subtypes. Gains in chromosomal arms 1q, 10p and 10q were common in endometrioid carcinomas. Multiple gains across the genome were identified in non-endometrioid carcinomas with the most common gains seen in 3q, 8q and 20q.

Probe Hybridization

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, solvent composition, temperature, and duration of incubation. At least one denaturation step may precede contact of the probes with the targets. Alternatively, both the probe and nucleic acid target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4.times. SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696 (the contents of which are herein incorporated by reference in their entirety, and specifically for the description of the use of blocking nucleic acid), may be used in conjunction with the methods of the present invention. Other conditions may be readily employed for specifically hybridizing the probes to their nucleic acid targets present in the sample, as would be readily apparent to one of skill in the art.

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

Detection of Probe Hybridization Patterns

The hybridization probes can be detected using any means known in the art. Label-containing moieties can be associated directly or indirectly with chromosomal probes. Different label-containing moieties can be selected for each individual probe within a particular combination so that each hybridized probe is visually distinct from the others upon detection. Where FISH is employed, the chromosomal probes can conveniently be labeled with distinct fluorescent label-containing moieties. In such embodiments, fluorophores, organic molecules that fluoresce upon irradiation at a particular wavelength, are typically directly attached to the chromosomal probes. A large number of fluorophores are commercially available in reactive forms suitable for DNA labeling.

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both of which are herein incorporated by reference for their descriptions of labeling probes.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SPECTRUMORANGE™ (Abbott Molecular, Des Plaines, Ill.) and SPECTRUM-GOLD™ (Abbott Molecular).

One of skill in the art will recognize that other agents or dyes can be used in lieu of fluorophores as label-containing moieties. Suitable labels that can be attached to probes include, but are not limited to, radioisotopes, fluorophores, chromophores, mass labels, electron dense particles, magnetic particles, spin labels, molecules that emit luminescence, electrochemically active molecules, enzymes, cofactors, and enzyme substrates. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for FISH.

Chromosomal probes hybridized to target regions may alternatively be visualized by enzymatic reactions of label moieties with suitable substrates for the production of insoluble color products. Each probe may be discriminated from other probes within the set by choice of a distinct label moiety. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for HRP.

In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present invention for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

In array CGH, the probes are not labeled, but rather are immobilized at distinct locations on a substrate, as described in WO 96/17958. In this context, the probes are often referred to as the "target nucleic acids." The sample nucleic acids are typically labeled to allow detection of hybridization complexes. The sample nucleic acids used in the hybridization may be detectably labeled prior to the hybridization reaction. Alternatively, a detectable label may be selected which binds to the hybridization product. In dual- or multi-color aCGH, the target nucleic acid array is hybridized to two or more collections of differently labeled nucleic acids, either simultaneously or serially. For example, sample nucleic acids (e.g., from endometrial carcinoma biopsy) and reference nucleic acids (e.g., from normal endometrium) are each labeled with a separate and distinguishable label. Differences in intensity of each signal at each target nucleic acid spot can be detected as an indication of a copy number difference. Although any suitable detectable label can be employed for aCGH, fluorescent labels are typically the most convenient.

Preferred methods of visualizing signals are described in WO 93/18186, which is hereby incorporated by reference for this description. To facilitate the display of results and to improve the sensitivity of detecting small differences in fluorescence intensity, a digital image analysis system can be used. An exemplary system is QUIPS (an acronym for quantitative image processing system), which is an automated image analysis system based on a standard fluorescence microscope equipped with an automated stage, focus control and filterwheel (Ludl Electronic Products, Ltd., Hawthorne, N.Y.). The filterwheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.) which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

Screening and Diagnosis of Patients for Endometrial Carcinoma

The detection methods of the invention include obtaining a biological sample from a subject having endometrial carcinoma or suspected of having endometrial carcinoma. The biological sample can be a cytology specimen, (e.g, uterine brushing, washing, or swab). In particular embodiments, the biological sample is a frozen or fixed specimen, such as formalin-fixed and paraffin embedded specimen. The sample is contacted with one or more chromosomal probe(s) to selectively detect endometrial carcinoma in the sample, if any, under conditions for specifically hybridizing the probes to their nucleic acid targets present in the sample. Probes of a combination can be hybridized concurrently or sequentially with the results of each hybridization imaged digitally, the probe or probes stripped, and the sample thereafter hybridized with the remaining probe or probes. Multiple probe combinations can also be hybridized to the sample in this manner.

The biological sample can be from a patient suspected of having endometrial carcinoma or from a patient diagnosed with endometrial carcinoma, e.g., for confirmation of diagnosis or establishing a clear margin, or for the detection of endometrial carcinoma cells in other tissues such as lymph nodes. The biological sample can also be from a subject with an ambiguous diagnosis in order to clarify the diagnosis. The biological sample can also be from a subject with a histopathologically benign lesion to confirm the diagnosis. Biological samples can be obtained using any of a number of methods known in the art.

As noted, a biological sample can be treated with a fixative such as formaldehyde and embedded in paraffin and sectioned for use in the methods of the invention. Alternatively, fresh or frozen tissue can be pressed against glass slides to form monolayers of cells known as touch preparations, which contain intact nuclei and do not suffer from the truncation artifact of sectioning. These cells may be fixed, e.g., in alcoholic solutions such as 100% ethanol or 3:1 methanol:acetic acid. Nuclei can also be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution such as formaldehyde.

Prescreening of Samples

Prior to detection, cell samples may be optionally preselected based on apparent cytologic abnormalities. Preselection identifies suspicious cells, thereby allowing the screening to be focused on those cells. Pre-selection allows for faster screening and increases the likelihood that a positive result will not be missed. During pre-selection, cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes such as propidium iodide or 4,6-diamidino-2-phenylindole dihydrochloride (DAPI) usually following hybridization of probes to their target DNAs. Typically, neoplastic cells harbor nuclei that are enlarged, irregular in shape, and/or show a mottled staining pattern. Propidium iodide, typically used at a concentration of about 0.4 .mu.g/ml to about 5 .mu.g/ml, is a red-fluorescing DNA-specific dye that can be observed at an emission peak wavelength of 614 nm. DAPI, typically used at a concentration of about 125 ng/ml to about 1000 ng/ml, is a blue fluorescing DNA-specific stain that can be observed at an emission peak wavelength of 452 nm. In this case, only those cells pre-selected for detection are subjected to counting for chromosomal losses and/or gains. Preferably, preselected cells on the order of at least 20, and more preferably at least 30-40, in number are chosen for assessing chromosomal losses and/or gains. Preselection of a suspicious region on a tissue section may be performed on a serial section stained by conventional means, such as H&E or PAP staining, and the suspect region marked by a pathologist or otherwise trained technician. The same region can then be located on the serial section stained by FISH and nuclei enumerated within that region. Within the marked region, enumeration may be limited to nuclei exhibiting abnormal characteristics as described above.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

Hybridization Pattern

In Situ Hybridization

The hybridization pattern for the set of chromosomal probes to the target regions is detected and recorded for cells chosen for assessment of chromosomal losses and/or gains. Hybridization is detected by the presence or absence of the particular signals generated by each of the chromosomal probes. The term "hybridization pattern" is intended to refer to the quantification of chromosomal losses/gains for those cells chosen for such assessment, relative to the number of the same in an evenly matched control sample, for each probe throughout a chosen cell sample. The quantification of losses/gains can include determinations that evaluate the ratio of one locus to another on the same or a different chromosome. Once the number of target regions within each cell is determined, as assessed by the number of regions showing hybridization to each probe, relative chromosomal gains and/or losses may be quantified.

The relative gain or loss for each probe is determined by comparing the number of distinct probe signals in each cell to the number expected in a normal cell, i.e., where the copy number should be two. Non-neoplastic cells in the sample, such as keratinocytes, fibroblasts, and lymphocytes, can be used as reference normal cells. More than the normal number of probe signals is considered a gain, and fewer than the normal number is considered a loss. Alternatively, a minimum number of signals per probe per cell can be required to consider the cell abnormal (e.g., 5 or more signals). Likewise for loss, a maximum number of signals per probe can be required to consider the cell abnormal (e.g., 0 signals, or one or fewer signals).

The percentages of cells with at least one gain and/or loss are to be recorded for each locus. A cell is considered abnormal if at least one of the identified genetic aberrations identified by a probe combination of the present invention is found in that cell. A sample may be considered positive for a gain or loss if the percentage of cells with the respective gain or loss exceeds the cutoff value for any probes used in an assay. Alternatively, two or more genetic aberrations can be required in order to consider the cell abnormal with the effect of increasing specificity. For example, wherein gains are indicative of a endometrial carcinoma, a sample is considered positive if it contains, for example, at least four cells showing gains of at least two or more probe-containing regions.

aCGH

Array CGH can be carried out in single-color or dual- or multi-color mode. In single-color mode, only the sample nucleic acids are labeled and hybridized to the nucleic acid array. Copy number differences can be detected by detecting a signal intensity at a particular target nucleic acid spot on the array that differs significantly from the signal intensity observed at one or more spots corresponding to one or more loci that are present in the sample nucleic acids at a normal copy number. To facilitate this determination, the array can include target elements for one or more loci that are not expected to show copy number difference(s) in endometrial carcinoma.

In dual- or multi-color mode, signal corresponding to each labeled collection of nucleic acids (e.g., sample nucleic acids and normal, reference nucleic acids) is detected at each target nucleic acid spot on the array. The signals at each spot can be compared, e.g., by calculating a ratio. For example, if the ratio of sample nucleic acid signal to reference nucleic acid signal exceeds 1, this indicates a gain in the sample nucleic acids at the locus corresponding to the target nucleic acid spot on the array. Conversely, if t if the ratio of sample nucleic acid signal to reference nucleic acid signal is less than 1, this indicates a loss in the sample nucleic acids at the corresponding locus.

Other Methods of Detecting Copy Number Variations Associated with Endometrial Carcinoma Those of skill in the art appreciate that copy number variations at any of the loci described herein can be detected using other methods, including amplification-based methods and high-throughput DNA sequencing.

Amplification-Based Detection

In amplification-based assays, the target nucleic acids act as template(s) in amplification reaction(s) (e.g., Polymerase Chain Reaction (PCR)). In a quantitative amplification, the amount of amplification product is proportional to the amount of template in the original sample. Detailed protocols for quantitative PCR are provided in Innis et al. (1990) PCR Protocols, A Guide to Methods and Applications, Academic Press, Inc. N.Y.). A number of commercial quantitative PCR systems are available, for example the TaqMan system from Applied Biosystems.

Other suitable amplification methods include, but are not limited to, ligase chain reaction (LCR) (see Wu and Wallace (1989) Genomics 4: 560; Landegren et al. (1988) Science 241: 1077; and Barringer et al. (1990) Gene 89: 117), multiplex ligation-dependent probe amplification (MLPA), transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

Amplification is typically carried out using primers that specifically amplify one or more loci within each chromosome or chromosomal subregion to be queried. Detection can be carried out by any standard means, including a target-specific probe, a universal probe that binds, e.g., to a sequence introduced into all amplicons via one or both primers, or a double-stranded DNA-binding dye (such as, e.g., SYBR Green). In illustrative embodiments, padlock probes or molecular inversion probes are employed for detection.

High-Throughput DNA Sequencing

In particular embodiments, amplification methods are employed to produce amplicons suitable for high-throughput (i.e., automated) DNA sequencing. Generally, amplification methods that provide substantially uniform amplification of target nucleotide sequences are employed in preparing DNA sequencing libraries having good coverage. In the context of automated DNA sequencing, the term "coverage" refers to the number of times the sequence is measured upon sequencing. The counts obtained are typically normalized relative to a reference sample or samples to determine relative copy number. Thus, upon performing automated sequencing of a plurality of target amplicons, the normalized number of times the sequence is measured reflects the number of target amplicons including that sequence, which, in turn, reflects the number of copies of the target sequence in the sample DNA.

Amplification for sequencing may involve emulsion PCR isolates in which individual DNA molecules along with primer-coated beads are present in aqueous droplets within an oil phase. Polymerase chain reaction (PCR) then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "Polony sequencing") and SOLiD sequencing, (developed by Agencourt, now Applied Biosystems). Another method for in vitro clonal amplification for sequencing is bridge PCR, where fragments are amplified upon primers attached to a solid surface, as used in the Illumina Genome Analyzer. Some sequencing methods do not require amplification, for example, the single-molecule method developed by the Quake laboratory (later commercialized by Helicos). This method uses bright fluorophores and laser excitation to detect pyrosequencing events from individual DNA molecules fixed to a surface. Pacific Biosciences has also developed a single molecule sequencing approach that does not require amplification.

After in vitro clonal amplification (if necessary), DNA molecules that are physically bound to a surface are sequenced. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time, and detect fluorescence at each position in real time, by repeated removal of the blocking group to allow polymerization of another nucleotide. Pyrosequencing (used by 454) also uses DNA polymerization, adding one nucleotide species at a time and detecting and quantifying the number of nucleotides added to a given location through the light emitted by the release of attached pyrophosphates.

Pacific Biosciences Single Molecule Real Time (SMRT™) sequencing relies on the processivity of DNA polymerase to sequence single molecules and uses phospho-linked nucleotides, each type labeled with a different colored fluorophore. As the nucleotides are incorporated into a complementary DNA strand, each is held by the DNA polymerase within a detection volume for a greater length of time than it takes a nucleotide to diffuse in and out of that detection volume. The DNA polymerase then cleaves the bond that previously held the fluorophore in place and the dye diffuses out of the detection volume so that fluorescence signal returns to background. The process repeats as polymerization proceeds.

Sequencing by ligation uses a DNA ligase to determine the target sequence. Used in the Polony method and in the SOLiD technology, this method employs a pool of all possible oligonucleotides of a fixed length, labeled according to the sequenced position. Oligonucleotides are annealed and ligated; the preferential ligation by DNA ligase for matching sequences results in a signal informative of the nucleotide at that position.

Probe Combinations and Kits for Use in Diagnostic and/or Prognostic Applications The invention includes highly specific and sensitive combinations of probes, as described herein, that can be used to detect endometrial carcinoma and kits for use in diagnostic, research, and prognostic applications. Kits include probe combinations and can also include reagents such as buffers and the like. The kits may include instructional materials containing directions (i.e., protocols) for the practice of the methods of this invention. While the instructional materials typically include written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

REFERENCES

1. Int J Mol Med. 2003 November; 12(5):727-31. 11q23-24 loss is associated with chromosomal instability in endometrial cancer. Kawasaki K, Suehiro Y, Umayahara K, Morioka H, Ito T, Saito T, Tsukamoto N, Sugino N, Kato H, Sasaki K.
2. Hum Genet. 1997 October; 100(5-6):629-36. Frequent gains on chromosome arms 1q and/or 8q in human endometrial cancer. Suzuki A, Fukushige S, Nagase S, Ohuchi N, Satomi S, Horii A.
3. Cancer Genet Cytogenet. 2008 February; 181(1):25-30. Recurrent gene amplifications in human type I endometrial adenocarcinoma detected by fluorescence in situ hybridization. Samuelson E, Levan K, Adamovic T, Levan G, Horvath G.
4. Cytogenet Genome Res. 2006; 115(1):16-22. Chromosomal alterations in 98 endometrioid adenocarcinomas analyzed with comparative genomic hybridization. Levan K, Partheen K, Osterberg L, Helou K, Horvath G.
5. Eur J Obstet Gynecol Reprod Biol. 2005 May 1; 120(1): 107-14. Genetic imbalances in endometrial hyperplasia and endometrioid carcinoma detected by comparative genomic hybridization. Muslumanoglu H M, Oner U, Ozalp S, Acikalin M F, Yalcin O T, Ozdemir M, Artan S.
6. Am J Clin Pathol. 2004 October; 122(4):546-51. Overrepresentation of 8q in carcinosarcomas and endometrial adenocarcinomas. Schulten H J, Gunawan B, Enders C, Donhuijsen K, Emons G, Füzesi L.
7. Hum Genet. 1997 October; 100(5-6):629-36. Frequent gains on chromosome arms 1q and/or 8q in human endometrial cancer. Suzuki A, Fukushige S, Nagase S, Ohuchi N, Satomi S, Horii A.
8. Genes Chromosomes Cancer. 1997 February; 18(2):115-25. Detection of DNA gains and losses in primary endometrial carcinomas by comparative genomic hybridization. Sonoda G, du Manoir S, Godwin A K, Bell D W, Liu Z, Hogan M, Yakushiji M, Testa J R.
9. U.S. Pat. No. 5,713,369 entitled "Uterine endometrial tissue sample brush."
10. U.S. Pat. No. 4,227,537 entitled "Endometrial brush with slidable protective sleeve."
11. Guido R S, Kanbour-Shakir A, Rulin M C, Christopherson W A. Pipelle endometrial sampling. Sensitivity in the detection of endometrial cancer. J Reprod Med 1995; 40(8):553-5.
12. Critchley H O, Warner P, Lee A J, Brechin S, Guise J, Graham B. Evaluation of abnormal uterine bleeding: comparison of three outpatient procedures within cohorts defined by age and menopausal status. Health Technol Assess 2004; 8(34):iii-iv, 1-139.
13. Del Priore G, Williams R, Harbatkin C B, Wan L S, Mittal K, Yang G C. Endometrial brush biopsy for the diagnosis of endometrial cancer. J Reprod Med 2001; 46(5):439-43.
14. Kipp B R, Medeiros F, Campion M B, Distad T J, Peterson L M, Keeney G L, et al. Direct uterine sampling with the Tao brush sampler using a liquid-based preparation method for the detection of endometrial cancer and atypical hyperplasia: a feasibility study. Cancer 2008; 114(4):228-35.
15. Maksem J A. Performance characteristics of the Indiana University Medical Center endometrial sampler (Tao Brush) in an outpatient office setting, first year's outcomes: recognizing histological patterns in cytology preparations of endometrial brushings. Diagn Cytopathol 2000; 22(3):186-95.
16. Williams A R, Brechin S, Porter A J, Warner P, Critchley H O. Factors affecting adequacy of Pipelle and Tao Brush endometrial sampling. Bjog 2008; 115(8):1028-36.
17. Yang G C, Wan L S. Endometrial biopsy using the Tao Brush method. A study of 50 women in a general gynecologic practice. J Reprod Med 2000; 45(2):109-14.

All publications cited herein are explicitly incorporated by reference.

EXAMPLES

The following examples are offered to illustrate, but not to limit the claimed invention.

Example 1

Array CGH Studies

Study Design

In a collaborative study of Abbott Molecular and Mayo Clinic carried out in 2007-2009, fresh-frozen, biopsy from proven endometrial carcinoma specimens from 62 patients were obtained with informed consent at the time of surgery from Rochester Methodist Hospital at Mayo Clinic, Rochester, Minn. Serial 5-μm sections were cut from the collected tissue and sections were stained with hematoxylin and eosin (H&E) for histological analysis. Specimens with greater than 70% tumor were selected for aCGH analysis and remaining sections were left unstained for future clinical studies.

DNA from the selected specimens was extracted and amplified prior to CGH analysis by the GenoSensor™ system. Vysis GenoSensor DNA microarray slides obtained from Abbott Molecular (Des Plaines, Ill.) were used for CGH analysis. The microarray slides contained 287 DNA targets consisting of known oncogenes, tumor suppressor genes, and regions of gain, loss, or loss of heterozygosity commonly associated with cancer (Attachment 1). The targets were arrayed in triplicate from BAC libraries.

Test and normal reference DNA samples were random-prime labeled, using Vysis GeneSensor labeling reagents, with Cyanine3-dCTP, and Cyanine5-dCTP (Perkin Elmer/NEN), respectively. Random priming refers to the process whereby synthetic DNA octamers of random sequence bind to complementary DNA sequences (along a DNA template) and serve as templates for DNA synthesis and elongation by DNA Polymerase I (Klenow Fragment). Following additional purification, test and reference DNA were mixed in equal proportion (in hybridization buffer), denatured, and hybridized against the Vysis GenoSensor™ Array 300 human genomic DNA microarray. Hybridization proceeded at 30° C. for 72 hours, followed by washing and scanning of arrays. Array images were analyzed with GenoSensor™ software, which segments and identifies each target using the blue (DAPI) image plane. The software measures mean intensities from the green and red image planes, subtracts background, determines mean ratio of green/red signal, and calculates the ratio most representative of the modal DNA copy number of the sample DNA. Gender mismatched (male/female or female/male) hybridizations provided control with respect to the detection of autosomal copy number imbalances. Arrays were hybridizes at Mayo Clinic and aCGH data obtained was analyzed by Abbott Molecular.

In total, data for 57 Cancer specimens (44 endometrioid and 13 non-endometrioid) and 9 normal specimens was available for analysis.

Results

Figures 1, 2A:
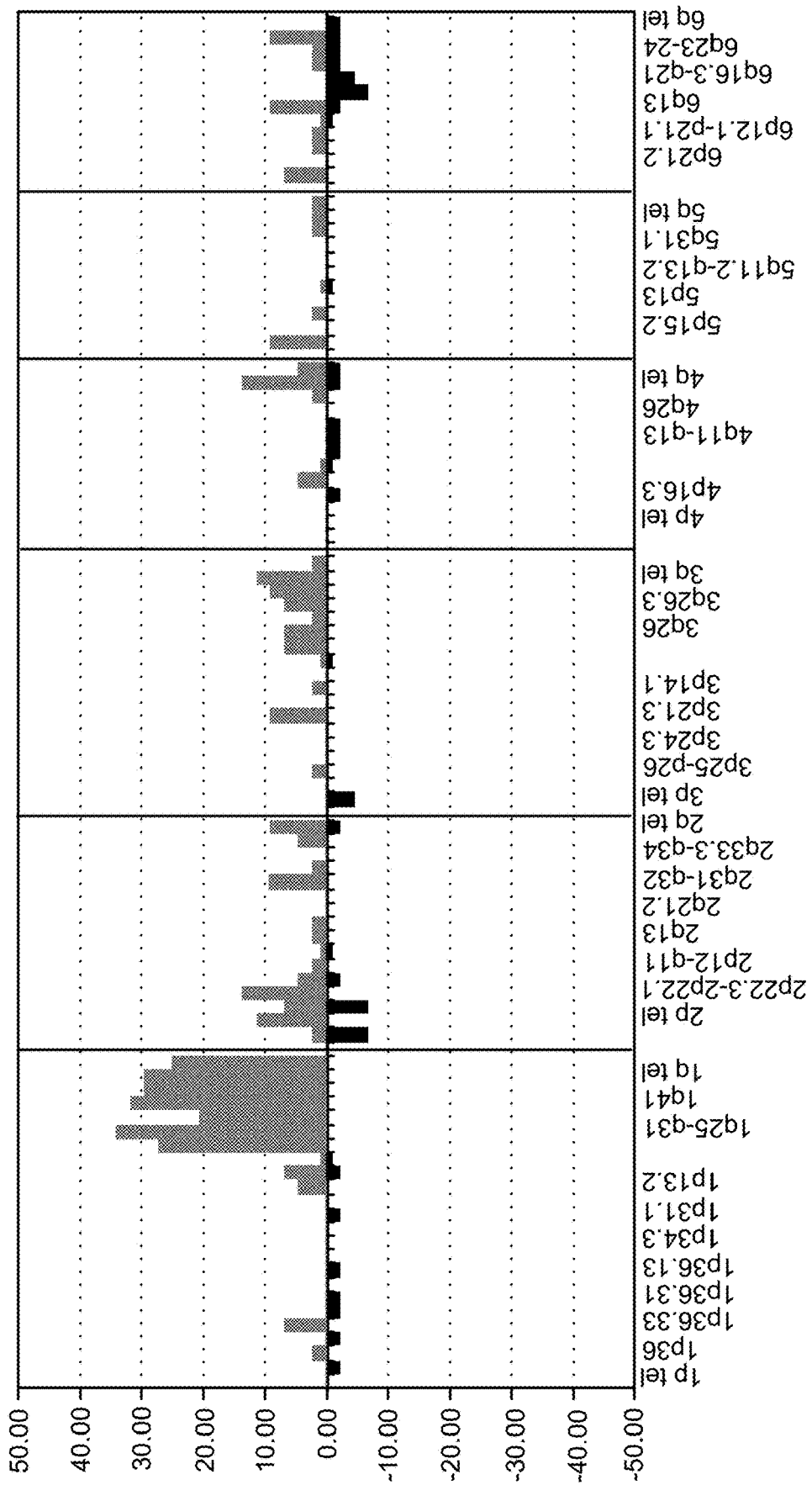
FIG. 2A(1-3)-B(1-3): The frequency of genomic changes in A, endometrioid cancers; B, non-endometrioid cancers from CGH data. A-1, 1ptel-6qtel; A-2, 7ptel-15q11.2-q12; A-3, 15q26.1-22qtel; B-1, 1ptel-6qtel; B-2, 7ptel-15q tel; B-3, 16ptel-22qtel.

The CGH data revealed several promising genomic targets for these investigational FISH probe sets (FIG. 1). The most frequent gains observed in all endometrial carcinomas included areas on chromosomal arms 1q, 2p, 3q, 8q, and 20q. Most common losses seen in all carcinomas included 9p, 9q, 16q, 17p, 18q, and 22q. Interestingly, different genomic changes were observed when comparing endometrioid and non-endometrioid subtypes. Gains in chromosomal arms 1q, 10p and 10q were common in endometrioid carcinomas. Multiple gains across the genome were identified in non-endometrioid carcinomas with the most common gains seen in 3q, 8q and 20q.

Gross analysis of chromosomal changes demonstrated that most frequent changes, of all cancers analyzed, were as follows:
1. Gains on 1q31-qtel (20-30%)
2. Gains on 3q, 8q and 10q (about 20%)
3. Gain on 2p (about 15%)
4. Losses on 9q (about 18%)
5. Losses on 15q11-q13 (about 18%)
6. Losses on 18q21.3 and 19ptel (about 18-19%)
7. Losses 16q and 17p (about 12%)

Table 1 provides details of the most frequently affected loci (by array clone).

TABLE 1

Loci with the frequently of genomic copy number imbalance of >10% in cancer specimens.

| Clone # | Clone Name | Cyto Location | FREQ GAIN (%) | FREQ LOSS (%) | FREQ GAIN Ca (%) | FREQ LOSS Ca (%) | FREQ IMBAL Ca (%) | FREQ GAIN EN (%) | FREQ LOSS EN (%) | FREQ GAIN NE (%) | FREQ LOSS NE (%) |
|---|---|---|---|---|---|---|---|---|---|---|---|
| 8 | AMC2 | q25-q31 | 7.27 | .00 | 1.58 | .00 | 1.58 | 4.09 | .00 | 3.08 | .00 |
| 0 | GFB2 | q41 | 2.73 | .00 | 6.32 | .00 | 6.32 | 1.82 | .00 | .69 | .00 |
| 7 | I-5663, I-13414 | q21 | 1.21 | .00 | 4.56 | .00 | 4.56 | 7.27 | .00 | 5.38 | .00 |
| 1 | KT3 | q44 | 2.73 | .00 | 4.56 | .00 | 4.56 | 9.55 | .00 | .69 | .00 |
| 2 | HGC-18290 | q tel | 2.73 | .00 | 4.56 | .00 | 4.56 | 9.55 | .00 | .69 | .00 |
| 36 | 29F16/SP6 | 9p tel | .03 | 6.67 | .51 | 9.30 | 2.81 | .27 | 8.18 | .69 | 3.08 |
| 3 | QTEL10 | q tel | 6.67 | .00 | 9.30 | .00 | 9.30 | 5.00 | .00 | .00 | .00 |
| 6 | YCN(N-myc) | p24.1 | 2.12 | .55 | 4.04 | .26 | 9.30 | .82 | .82 | 8.46 | .00 |
| 4 | FI2 | q tel | 6.67 | .00 | 9.30 | .00 | 9.30 | 1.36 | .00 | 6.15 | .00 |
| 10 | YC | g24.12-q24.13 | 6.67 | .00 | 9.30 | .00 | 9.30 | .82 | .00 | 1.54 | .00 |
| 11 | TK2 | q24-qter | 6.67 | .00 | 9.30 | .00 | 9.30 | .82 | .00 | 1.54 | .00 |
| 22 | SC1 | q34 | .52 | 5.15 | .75 | 7.54 | 9.30 | .27 | .09 | .00 | 6.15 |
| 35 | GFR2 | 0q26 | 6.67 | .00 | 9.30 | .00 | 9.30 | 0.45 | .00 | 5.38 | .00 |
| 82 | BE3A, 15S10 | 5q11-q13 | .52 | 5.15 | .75 | 7.54 | 9.30 | .27 | 3.64 | .00 | 0.77 |
| 31 | CC | 8q21.3 | .52 | 6.67 | .75 | 7.54 | 9.30 | .27 | .82 | .00 | 3.85 |
| 3 | P63 | q27-q29 | 5.15 | .00 | 7.54 | .00 | 7.54 | .09 | .00 | 6.15 | .00 |
| 06 | GFR1 | p11.2-p11.1 | 2.12 | .03 | 4.04 | .51 | 7.54 | .09 | .27 | 0.77 | .69 |
| 21 | BCCR1 | q33.2 | .52 | 3.64 | .75 | 5.79 | 7.54 | .27 | .82 | .00 | 6.15 |
| 6 | QTEL11 | q tel | 0.61 | .55 | 0.53 | .26 | 5.79 | 3.64 | .27 | .00 | 5.38 |
| 02 | 8S596 | p tel | .58 | .06 | .77 | .02 | 5.79 | .82 | .55 | 5.38 | 5.38 |
| 96 | RA16D | 6q23.2 | .03 | 0.61 | .51 | 2.28 | 5.79 | .00 | .09 | 5.38 | 3.08 |
| 70 | F2 | 2q12.2 | .58 | .06 | .77 | .02 | 5.79 | .82 | .82 | 5.38 | .69 |
| 71 | DGFB( SIS) | 2q13.1 | .69 | .15 | .77 | .02 | 5.79 | .82 | .27 | 5.38 | 3.08 |
| 9 | TGS2(COX2) | q31.1 | 3.64 | .00 | 5.79 | .00 | 5.79 | 0.45 | .00 | .00 | .00 |
| 7 | SH2, KCNK12 | p22.3-p22.1 | 3.64 | .00 | 5.79 | .00 | 5.79 | 3.64 | .00 | 3.08 | .00 |
| 09 | XT1 | g24.11-q24.13 | 3.64 | .00 | 5.79 | .00 | 5.79 | .82 | .00 | 6.15 | .00 |
| 12 | HGC-3110 | q tel | 3.64 | .00 | 5.79 | .00 | 5.79 | .55 | .00 | 3.85 | .00 |
| 6 | 1S2465, 1S3402 | p12 | 0.61 | .52 | 2.28 | .75 | 4.04 | .82 | .27 | 0.77 | .00 |
| 99 | ANCA | 6q24.3 | .52 | 0.61 | .75 | 2.28 | 4.04 | .27 | .09 | .00 | 3.08 |
| 0 | L6 | p21 | 2.12 | .00 | 4.04 | .00 | 4.04 | 1.36 | .00 | 3.08 | .00 |
| 01 | 8S504 | p tel | .06 | .06 | .02 | .02 | 4.04 | .82 | .55 | .69 | 5.38 |
| 37 | tSG27915 | 0q tel | 2.12 | .00 | 4.04 | .00 | 4.04 | 5.91 | .00 | .69 | .00 |
| 97 | DH13 | 6g24.2-q24.3 | .00 | 2.12 | .00 | 4.04 | 4.04 | .00 | .09 | .00 | 0.77 |
| 5 | PTEL27 | p tel | 0.61 | .00 | 2.28 | .00 | 2.28 | 1.36 | .00 | 5.38 | .00 |
| 8 | 2S447 | q tel | .06 | .55 | .02 | .26 | 2.28 | .09 | .27 | .00 | 5.38 |
| 5 | ASSF1 | p21.3 | 0.61 | .00 | 2.28 | .00 | 2.28 | .09 | .00 | 3.08 | .00 |
| 7 | 4S2930 | q tel | .03 | .58 | .51 | .77 | 2.28 | .55 | .27 | .00 | 0.77 |

TABLE 1-continued

Loci with the frequently of genomic copy number imbalance of >10% in cancer specimens.

| Clone # | Clone Name | Cyto Location | FREQ GAIN (%) | FREQ LOSS (%) | FREQ GAIN Ca (%) | FREQ LOSS Ca (%) | FREQ IMBAL Ca (%) | FREQ GAIN EN (%) | FREQ LOSS EN (%) | FREQ GAIN NE (%) | FREQ LOSS NE (%) |
|---|---|---|---|---|---|---|---|---|---|---|---|
| 8 | 84C11/T3 | p tel | .09 | .52 | 0.53 | .75 | 2.28 | .09 | .00 | 5.38 | .69 |
| 2 | TR1B | q13 | .09 | .52 | 0.53 | .75 | 2.28 | .09 | .27 | 5.38 | .00 |
| 36 | MBT1 | 0g25.3-q26.1 | .09 | .52 | 0.53 | .75 | 2.28 | 3.64 | .00 | .00 | .69 |
| 78 | GH(D14S308) | 4q tel | 2.12 | .00 | 2.28 | .00 | 2.28 | .09 | .00 | 3.08 | .00 |
| 08 | 17S125, 17S61 | 7p12-p11.2 | .00 | 0.61 | .00 | 2.28 | 2.28 | .00 | .55 | .00 | 8.46 |
| 10 | LGL1 | 7p12-17p11.2 | .00 | 0.61 | .00 | 2.28 | 2.28 | .00 | .82 | .00 | 0.77 |
| 48 | OP1 | 0q12-q13.1 | .09 | .52 | 0.53 | .75 | 2.28 | .55 | .27 | 0.77 | .00 |
| 49 | COA3(AIB1) | 0q12 | 0.61 | .00 | 2.28 | .00 | 2.28 | .27 | .00 | 6.15 | .00 |
| 57 | PD52L2, TOM | 0q tel | 0.61 | .00 | 2.28 | .00 | 2.28 | .55 | .00 | 8.46 | .00 |
| 69 | CR | 2q11.23 | .55 | .58 | .51 | .77 | 2.28 | .00 | .82 | 5.38 | 5.38 |

Figures 2, 2A:
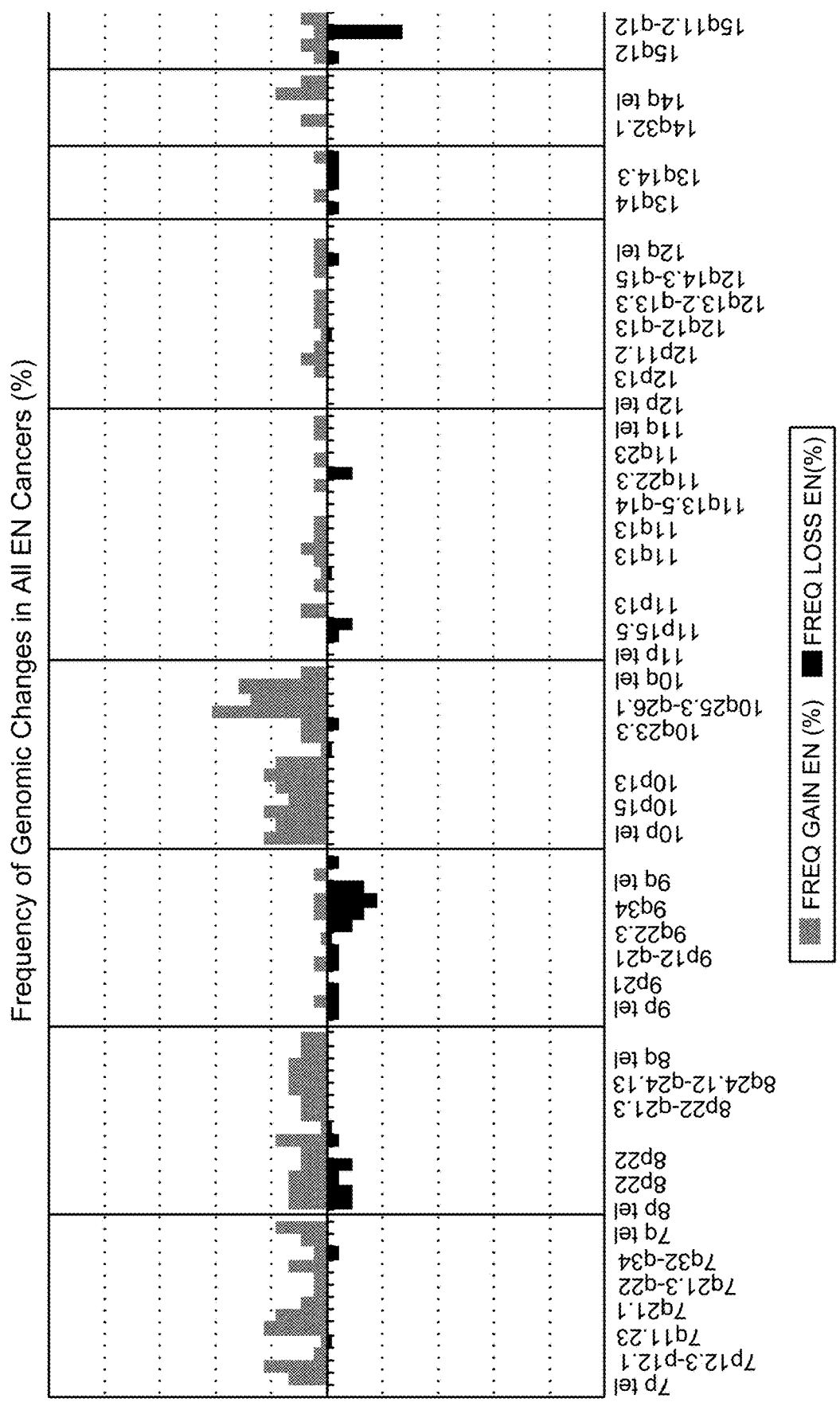

As evident from FIG. 2, Non-Endometrioid (NE) tumors had overall greater number of genomic changes as compared to Endometrioid (EN) tumors. In addition, the pattern of changes was different between EN and NE tumors. For example, changes at 1q and 10q loci were more prevalent in EN tumors, while changes at 8q and 18q appeared more prevalent in NE tumors.

Sensitivity and Specificity Analysis

Analysis was carried out to determine changes in which loci are most abundant in cancers (both NE and EN) and give the highest sensitivity and specificity in detecting cancer.

First, analysis has been carried out on individual loci and the loci with the best sensitivity and specificity value as represented by the DFI parameter calculated as:

$$DFI = \sqrt{(1-SENS)^2 + (1-SPEC)^2}$$

were selected. As shown below, the best performance was demonstrated by loci located on the long arm of chromosome 1.

| PROBE 1 | case # specimens | SENS | SPEC vs norm | DFI vs norm |
|---|---|---|---|---|
| LAMC2:18:1q25-q31 | 57 | 0.3158 | 1.0000 | 0.6842 |
| TGFB2:20:1q41 | 57 | 0.2632 | 1.0000 | 0.7368 |
| WI-5663, WI-13414:17:1q21 | 57 | 0.2456 | 1.0000 | 0.7544 |
| SHGC-18290:22:1q tel | 57 | 0.2456 | 1.0000 | 0.7544 |
| AKT3:21:1q44 | 57 | 0.2456 | 0.8889 | 0.7625 |

Then, we considered additional clones, and chosen a representative probe for a segment where several probes were located in one apparent contiguous region of rearrangement. It is evident (Table 2) that the sensitivity and specificity of the individual loci is low. Therefore, combinations of the loci listed below were evaluated.

TABLE 2

Individual clone performance for selected clones.

| Clone | | control # specimens | SENS | case # specimens | SENS | SPEC vs norm | DFI vs norm | Case marker(s)+ | Case marker(s)− | Control marker(s)+ | Control marker(s)− | chi sq prob |
|---|---|---|---|---|---|---|---|---|---|---|---|---|
| LAMC2:18:1q25-q31 | abnorm | 9 | 0.0000 | 57 | 0.3158 | 1.0000 | 0.6842 | 18 | 39 | 0 | 9 | 4.8060E−02 |
| MYCN(N-myc):26:2p24.1 | abnorm | 9 | 0.0000 | 57 | 0.1930 | 1.0000 | 0.8070 | 11 | 46 | 0 | 9 | 1.4883E−01 |
| RASSF1:45:3p21.3 | abnorm | 9 | 0.0000 | 57 | 0.1228 | 1.0000 | 0.8772 | 7 | 50 | 0 | 9 | 2.6617E−01 |
| TP63:53:3q27-q29 | abnorm | 9 | 0.0000 | 57 | 0.1754 | 1.0000 | 0.8246 | 10 | 47 | 0 | 9 | 1.7252E−01 |
| IL6:90:7p21 | abnorm | 9 | 0.0000 | 57 | 0.1404 | 1.0000 | 0.8596 | 8 | 49 | 0 | 9 | 2.3056E−01 |
| FGFR1:106:8p11.2-p11.1 | abnorm | 9 | 0.0000 | 57 | 0.1754 | 1.0000 | 0.8246 | 10 | 47 | 0 | 9 | 1.7252E−01 |
| MYC:110:8q24.12-q24.13 | abnorm | 9 | 0.0000 | 57 | 0.1930 | 1.0000 | 0.8070 | 11 | 46 | 0 | 9 | 1.4883E−01 |
| TSC1:122:9q34 | abnorm | 9 | 0.0000 | 57 | 0.1930 | 1.0000 | 0.8070 | 11 | 46 | 0 | 9 | 1.4883E−01 |
| PTEN:134:10q23.3 | abnorm | 9 | 0.2222 | 57 | 0.0702 | 0.7778 | 0.9560 | 4 | 53 | 2 | 7 | 1.4034E−01 |
| FGFR2:135:10q26 | abnorm | 9 | 0.0000 | 57 | 0.1930 | 1.0000 | 0.8070 | 11 | 46 | 0 | 9 | 1.4883E−01 |
| UBE3A, D15S10:182:15q11-q13 | abnorm | 9 | 0.0000 | 57 | 0.1930 | 1.0000 | 0.8070 | 11 | 46 | 0 | 9 | 1.4883E−01 |
| FANCA:199:16q24.3 | abnorm | 9 | 0.0000 | 57 | 0.1404 | 1.0000 | 0.8596 | 8 | 49 | 0 | 9 | 2.3056E−01 |
| DCC:231:18q21.3 | abnorm | 9 | 0.1111 | 57 | 0.1930 | 0.8889 | 0.8146 | 11 | 46 | 1 | 8 | 5.5398E−01 |
| NCOA3(AIB1):249:20q12 | abnorm | 9 | 0.0000 | 57 | 0.1228 | 1.0000 | 0.8772 | 7 | 50 | 0 | 9 | 2.6617E−01 |
| ZNF217(ZABC1):254:20q13.2 | abnorm | 9 | 0.0000 | 57 | 0.0702 | 1.0000 | 0.9298 | 4 | 53 | 0 | 9 | 4.1224E−01 |

Figures 2, 2A, 3:
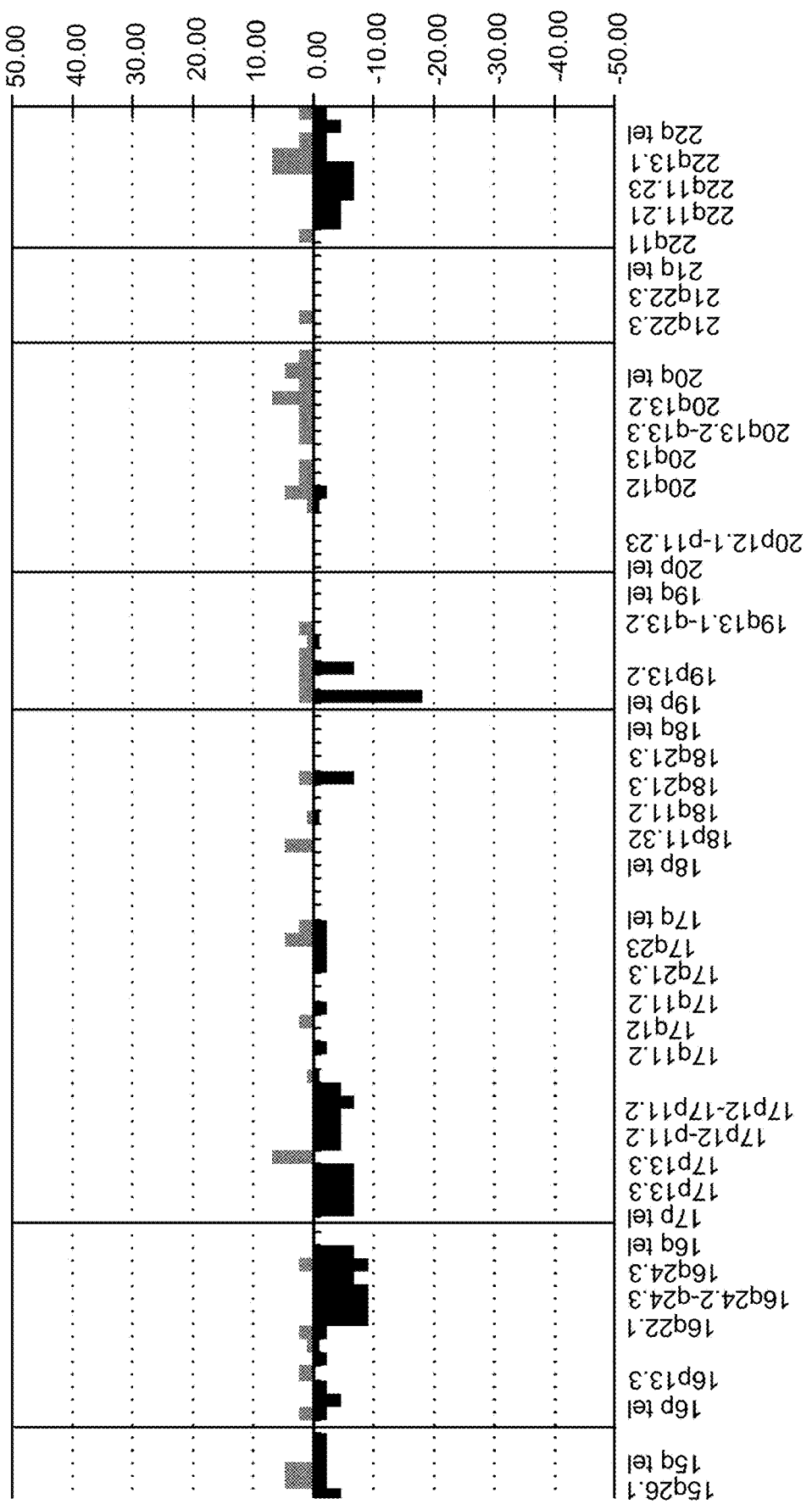
FIG. 3: Complementation of selected genomic array clones. A, Abnormal (gain or loss); NC, no change in copy number.
Figures 1, 2B:
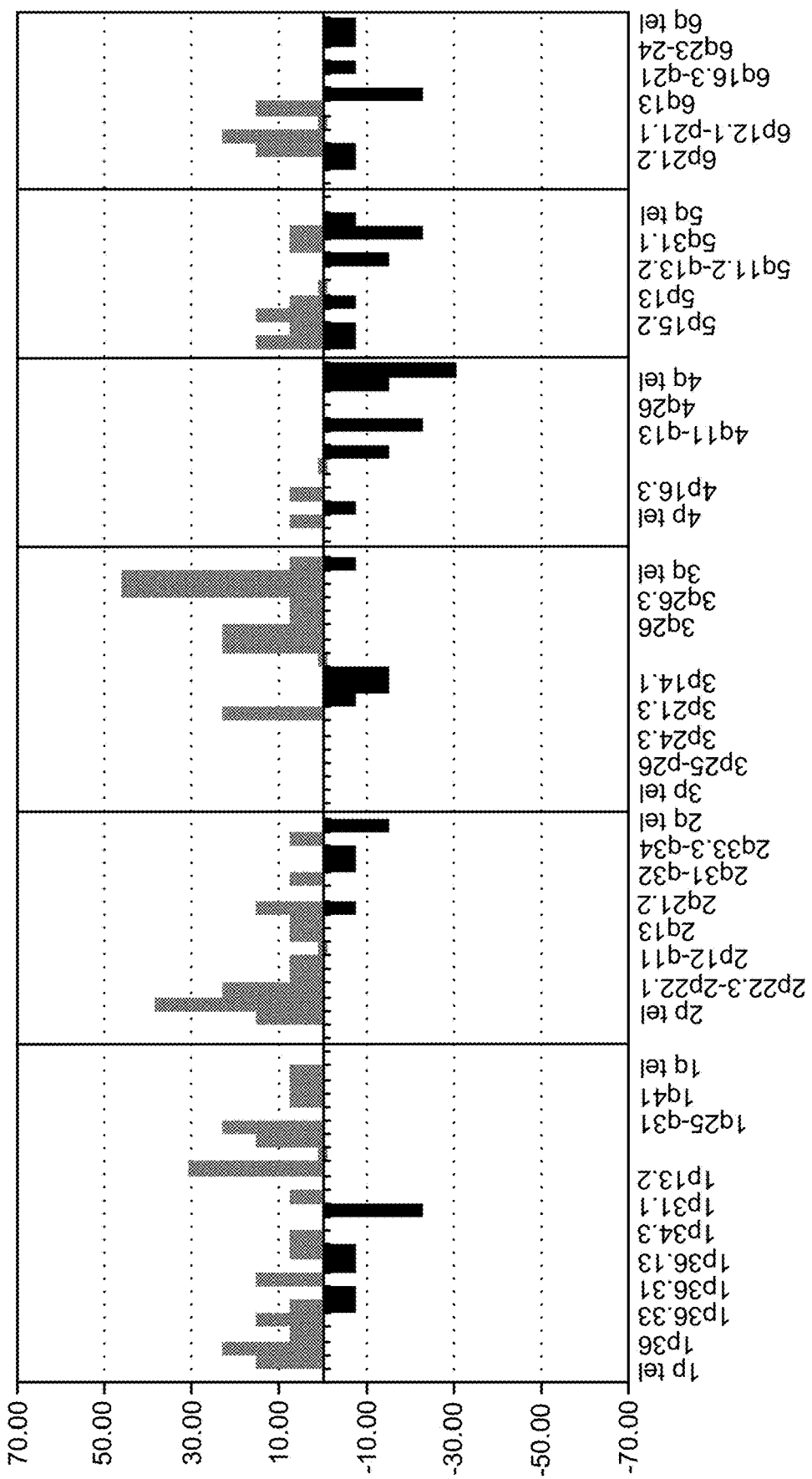
Figures 2, 2B:
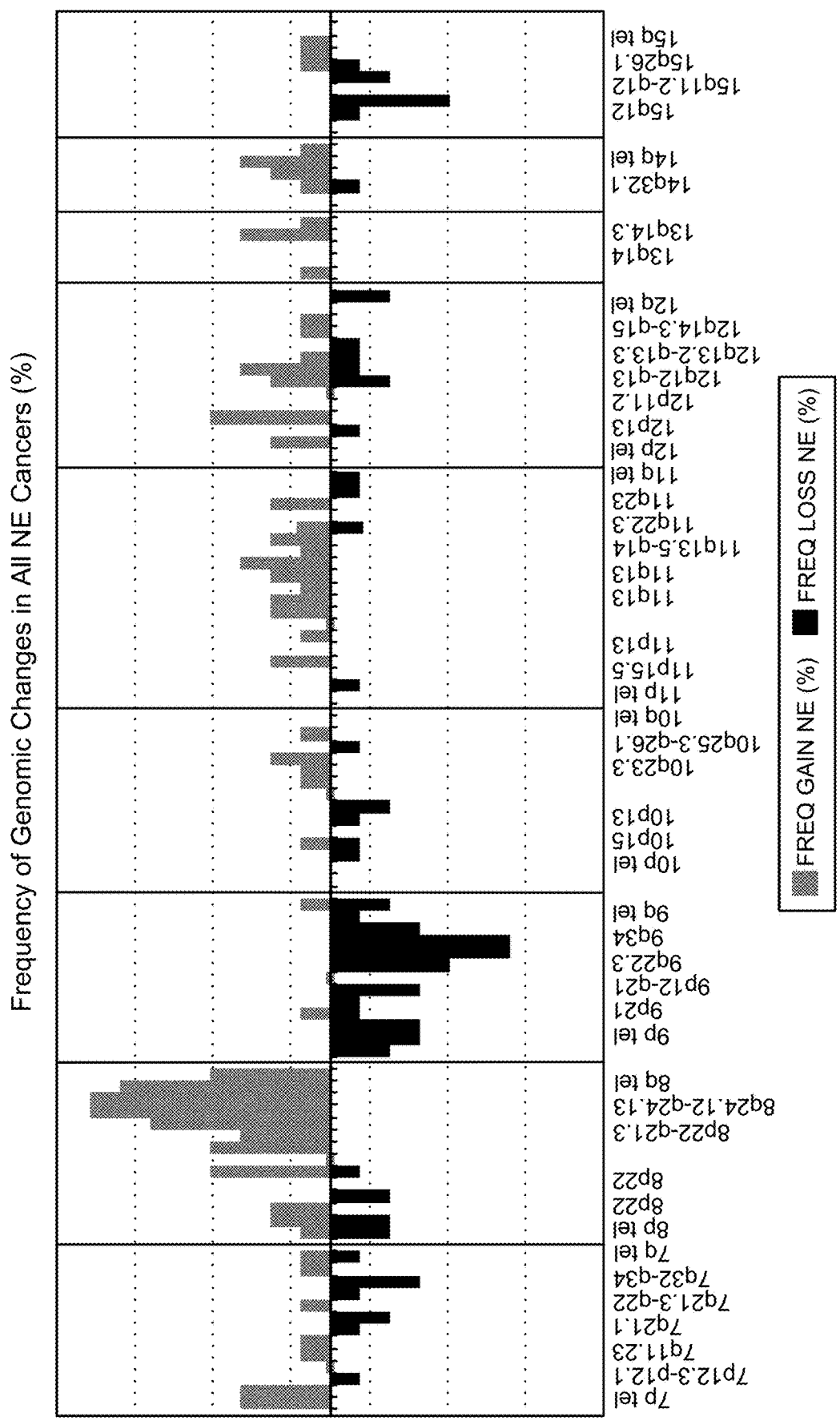
Figures 2, 2B, 3:
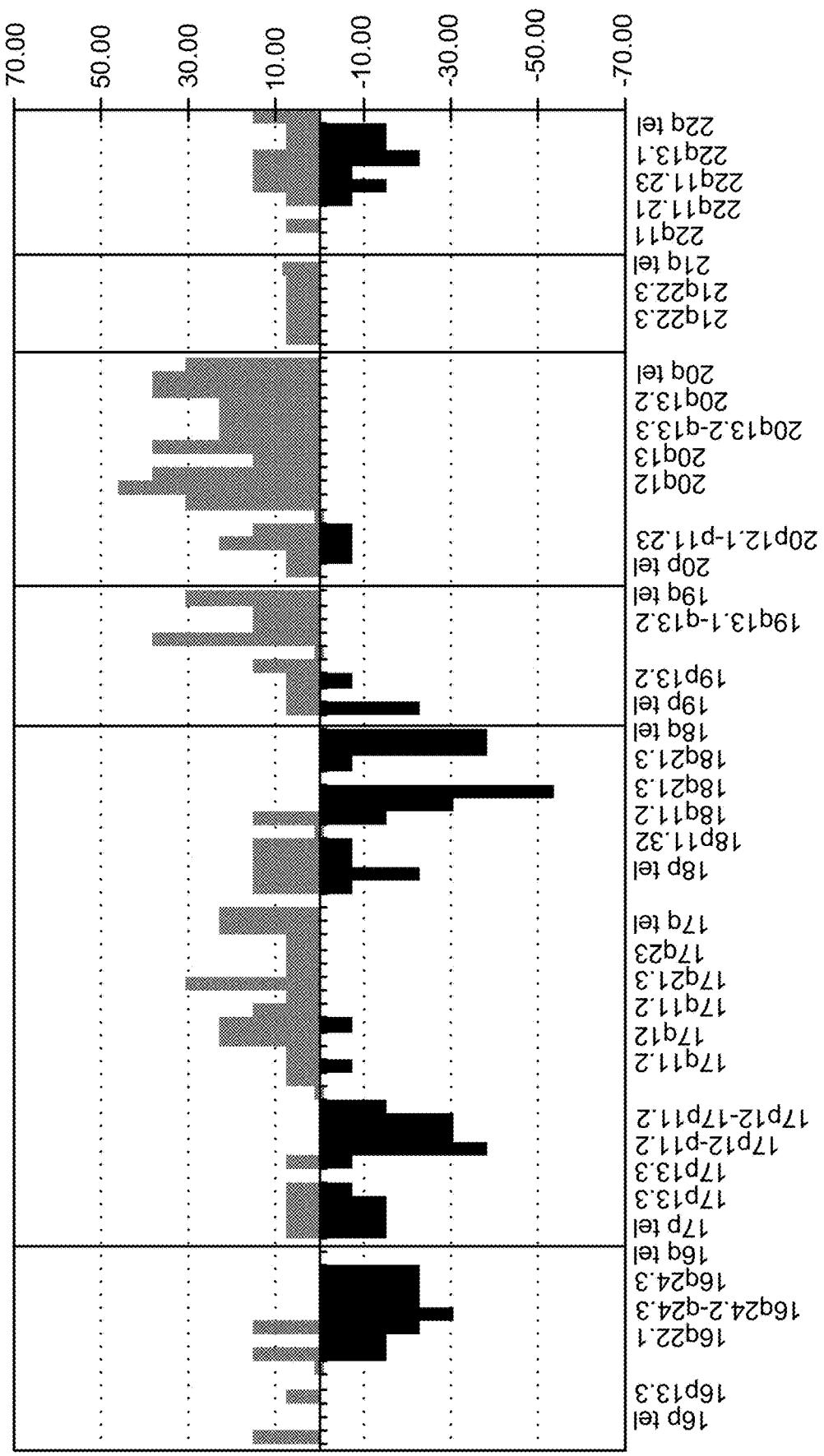
Figure 4A:
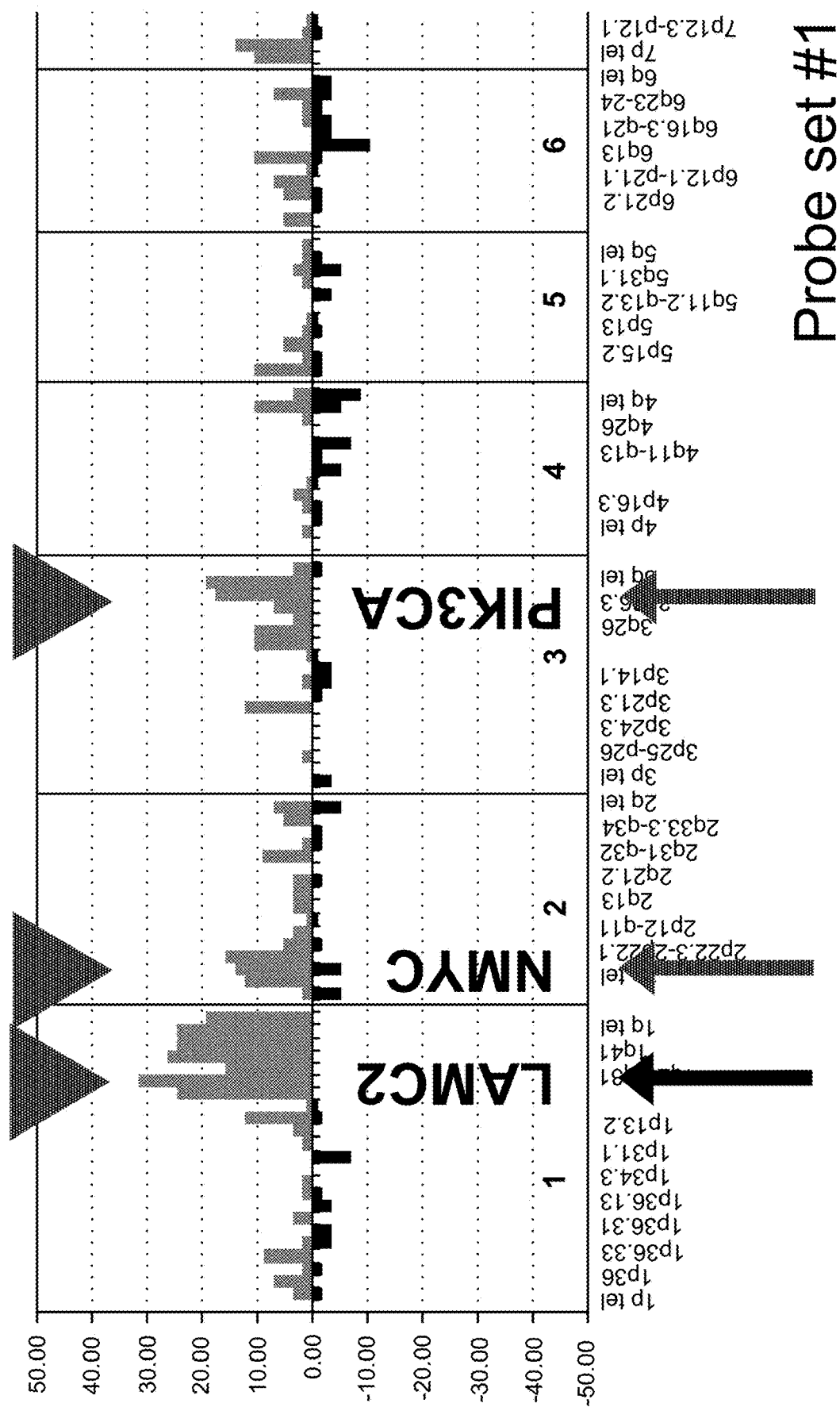
FIG. 4A-I: Probe sets 1 and 2 shown on the aCGH data output; frequency of genomic changes in all cancers: A, 1ptel-7p12.3-p12.1; B, 7q11.23-15qtel; C, 16ptel-22qtel. Frequency of genomic changes in endometrioid cancers: D, 1ptel-6qtel; E, 7ptel-15q11.2-q12; F, 15q26.1-22qtel. Frequency of genomic changes in non-endometrioid cancers: G, 1ptel-6qtel; H, 7ptel-15q tel; I, 16ptel-22qtel.
Figure 4B:
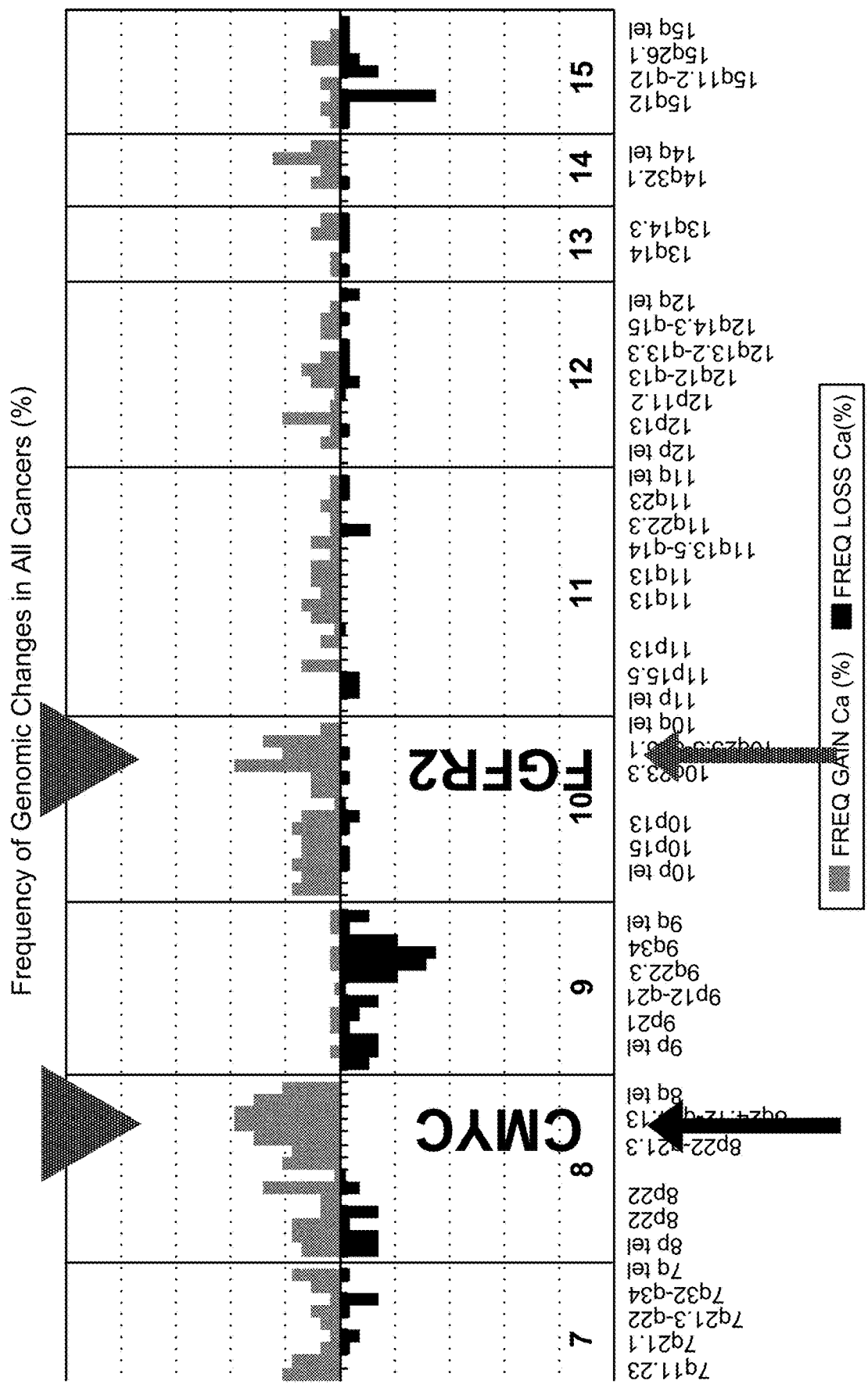
Figure 4C:
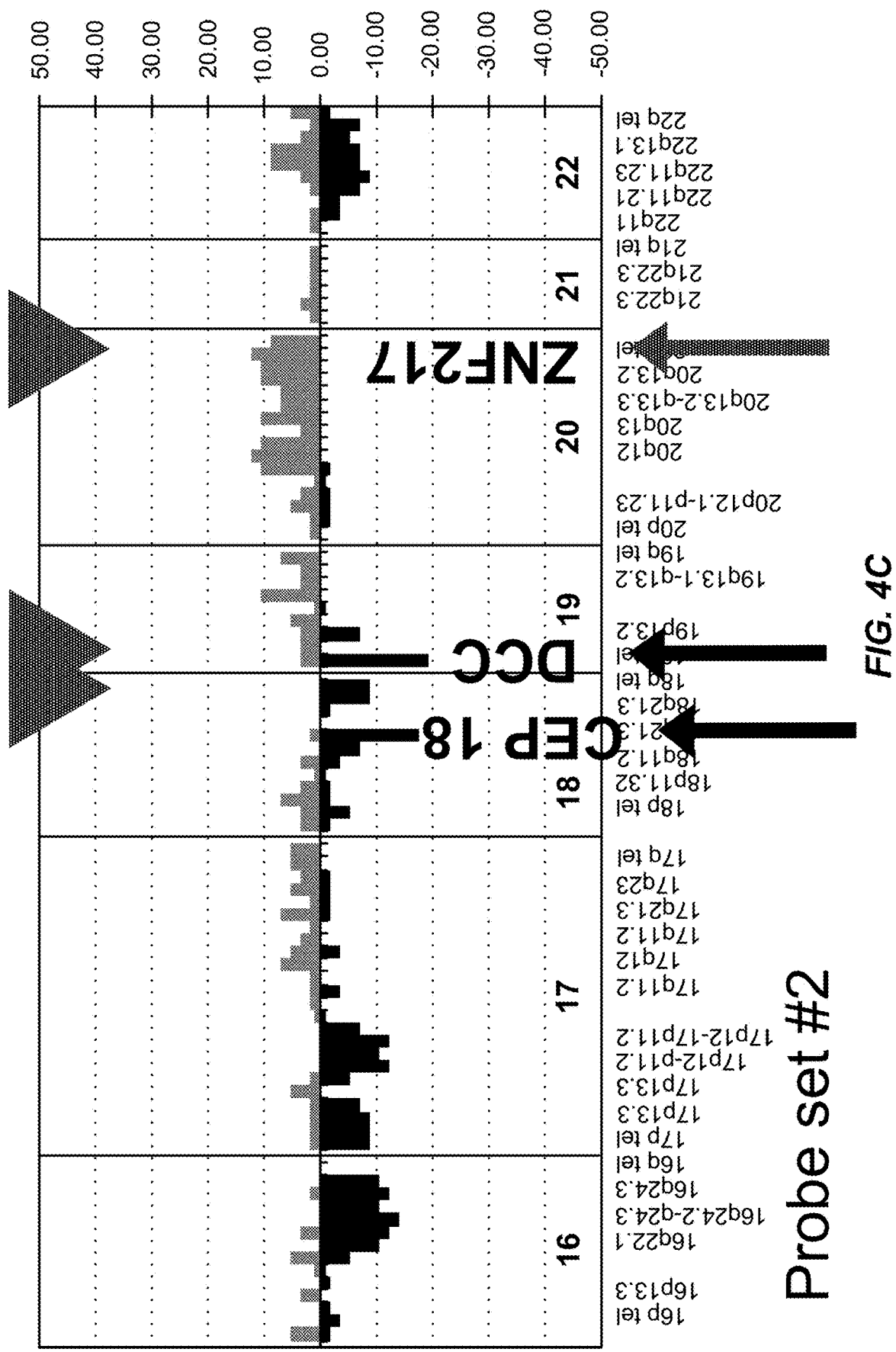
Figure 4D:
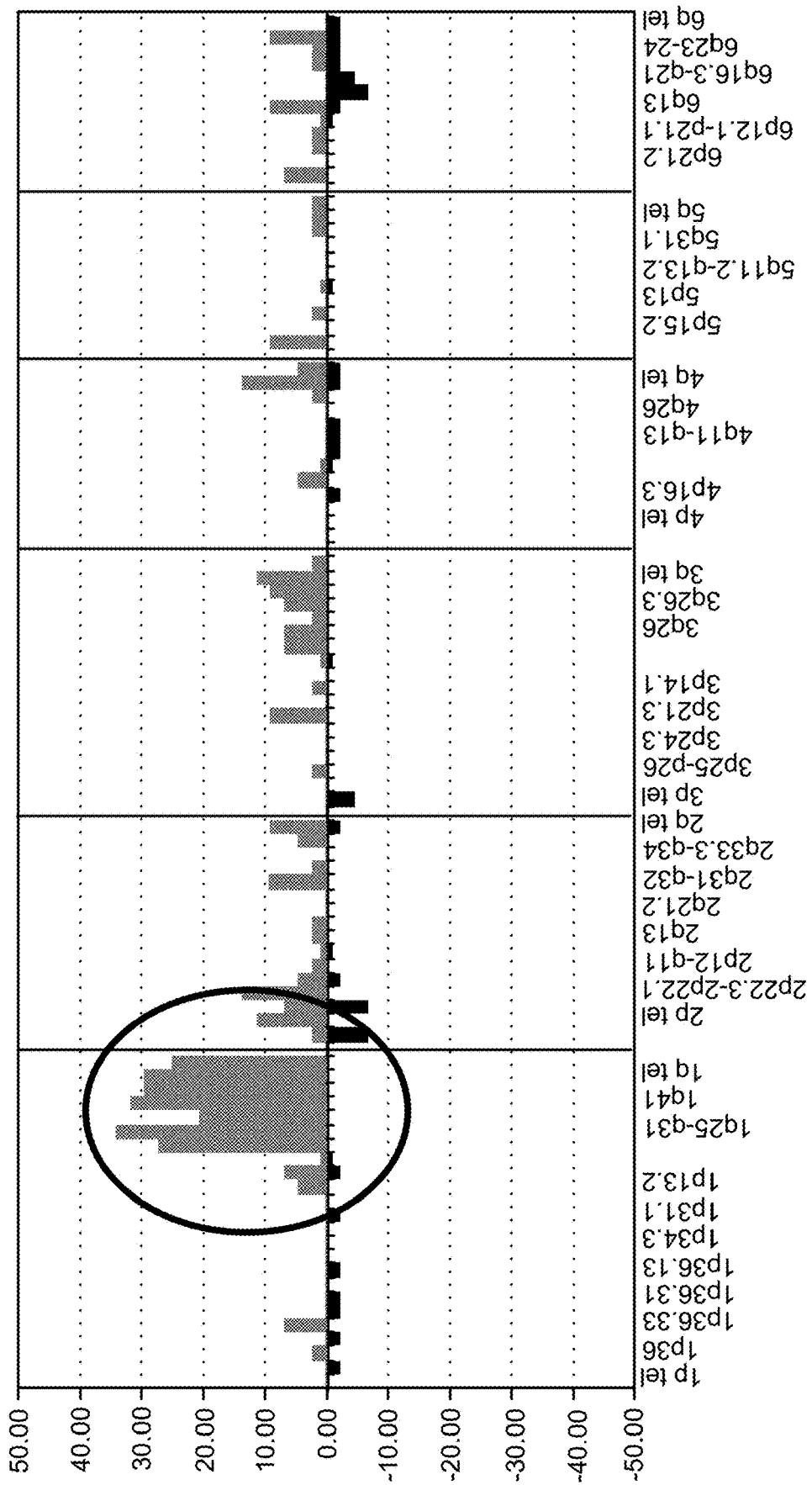
Figure 4E:
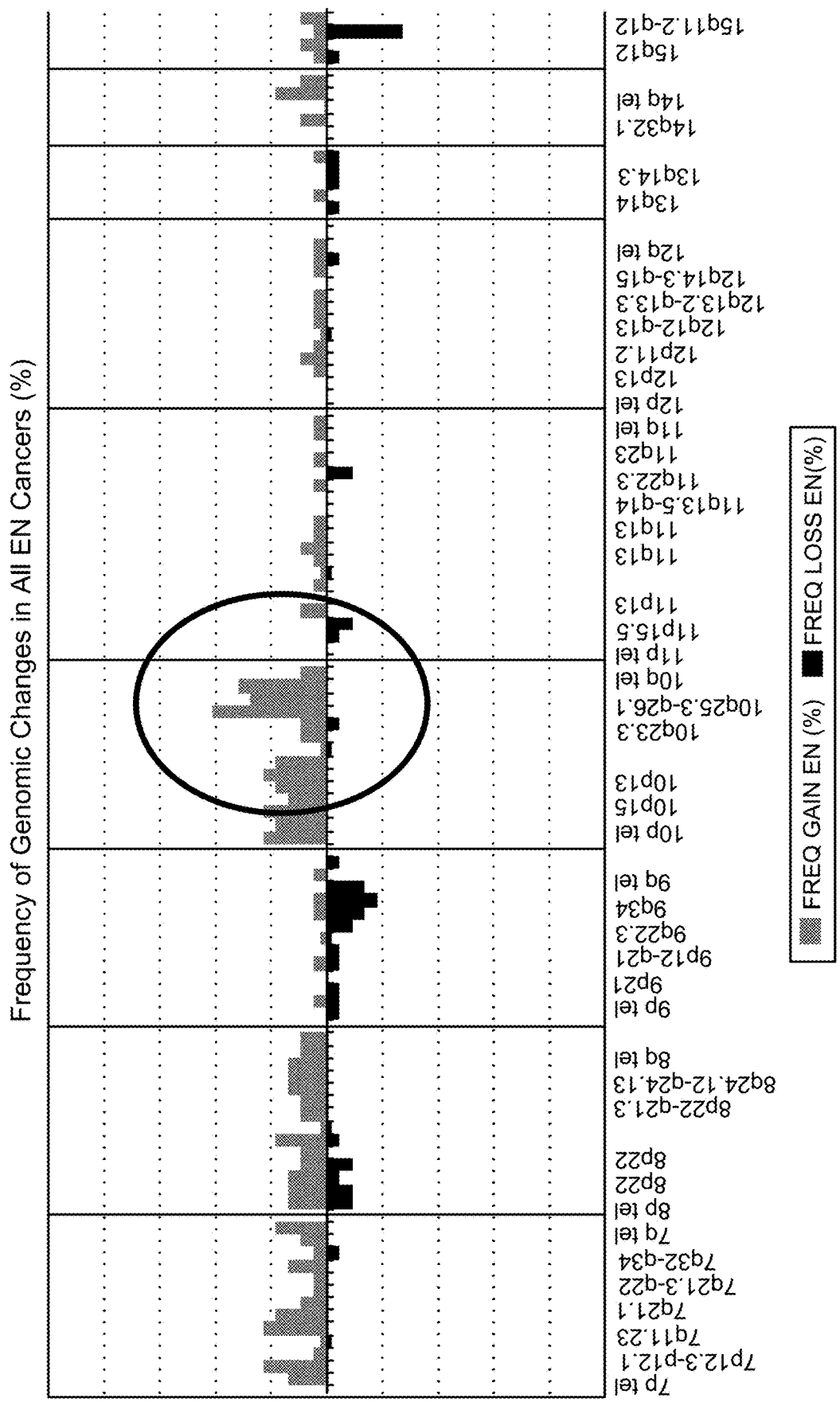
Figure 4F:
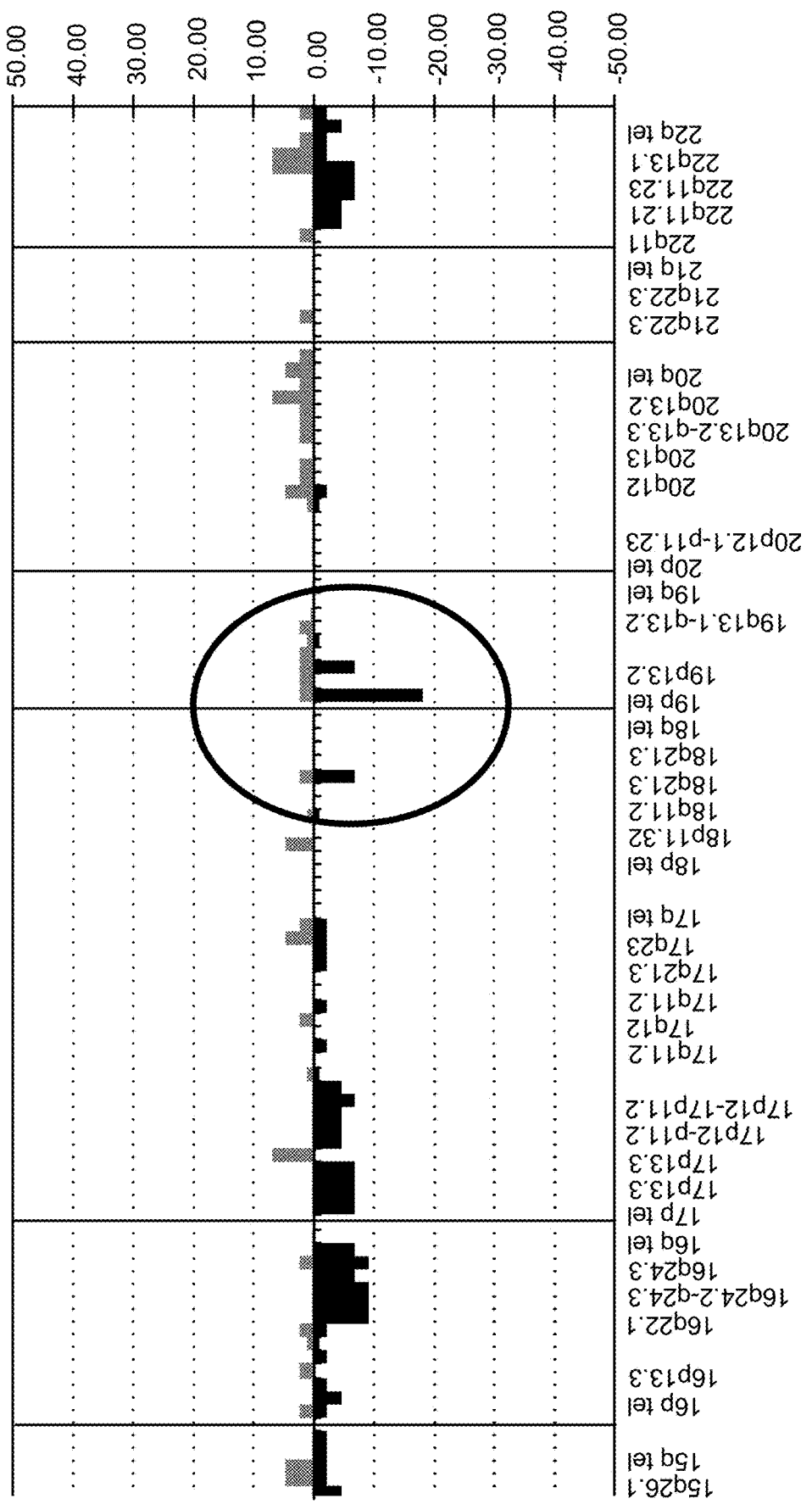
Figure 4G:
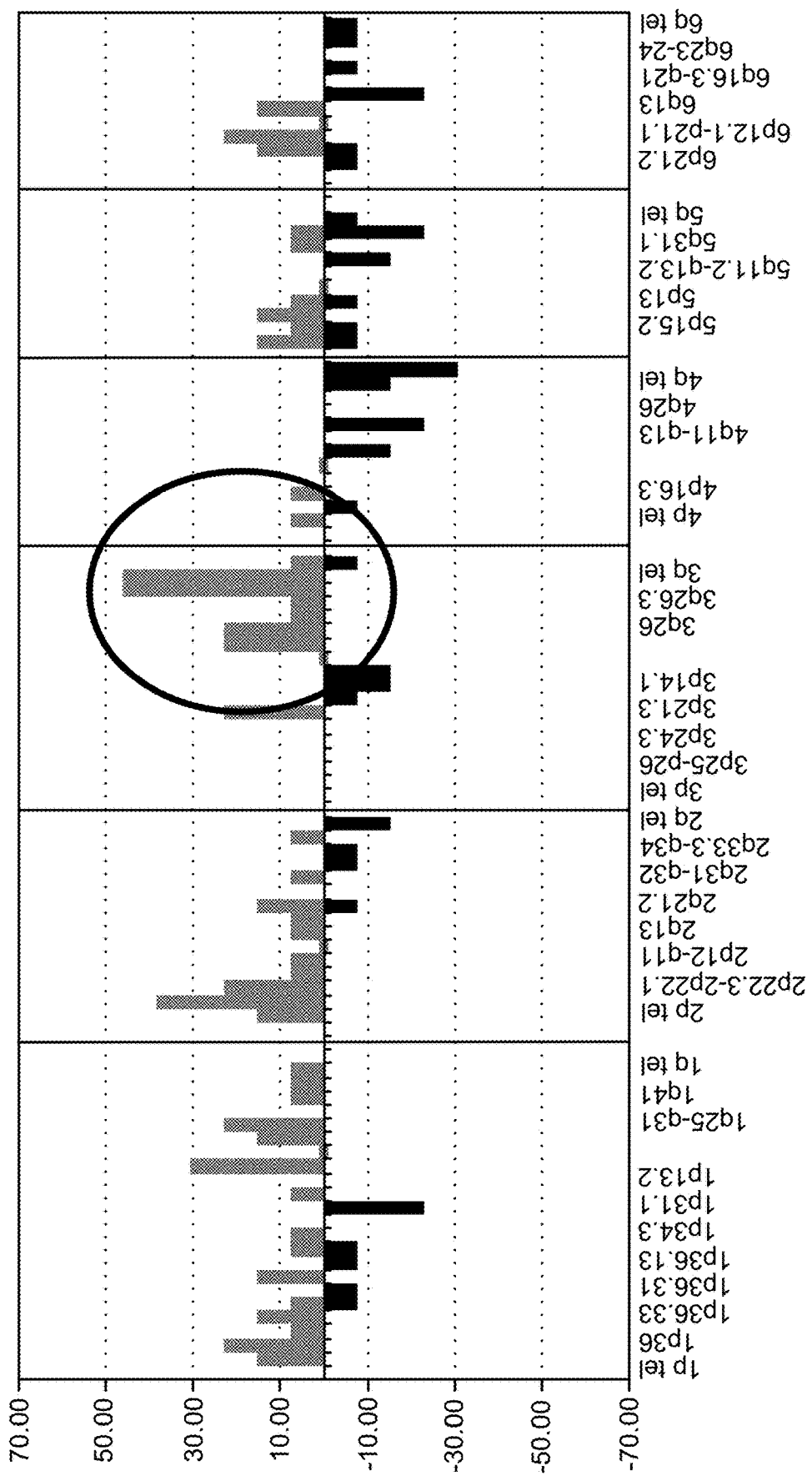
Figure 4H:
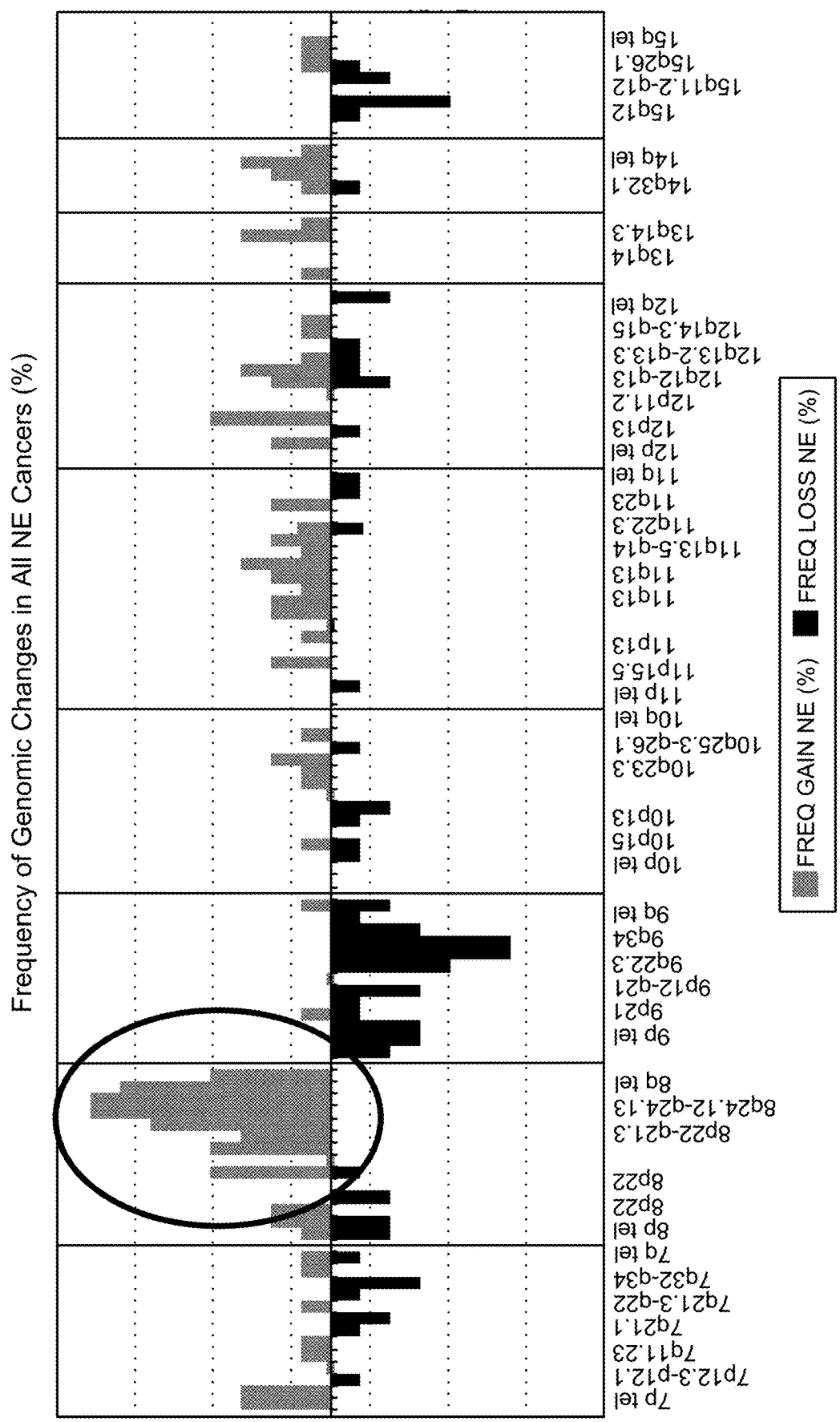
Figure 4I:
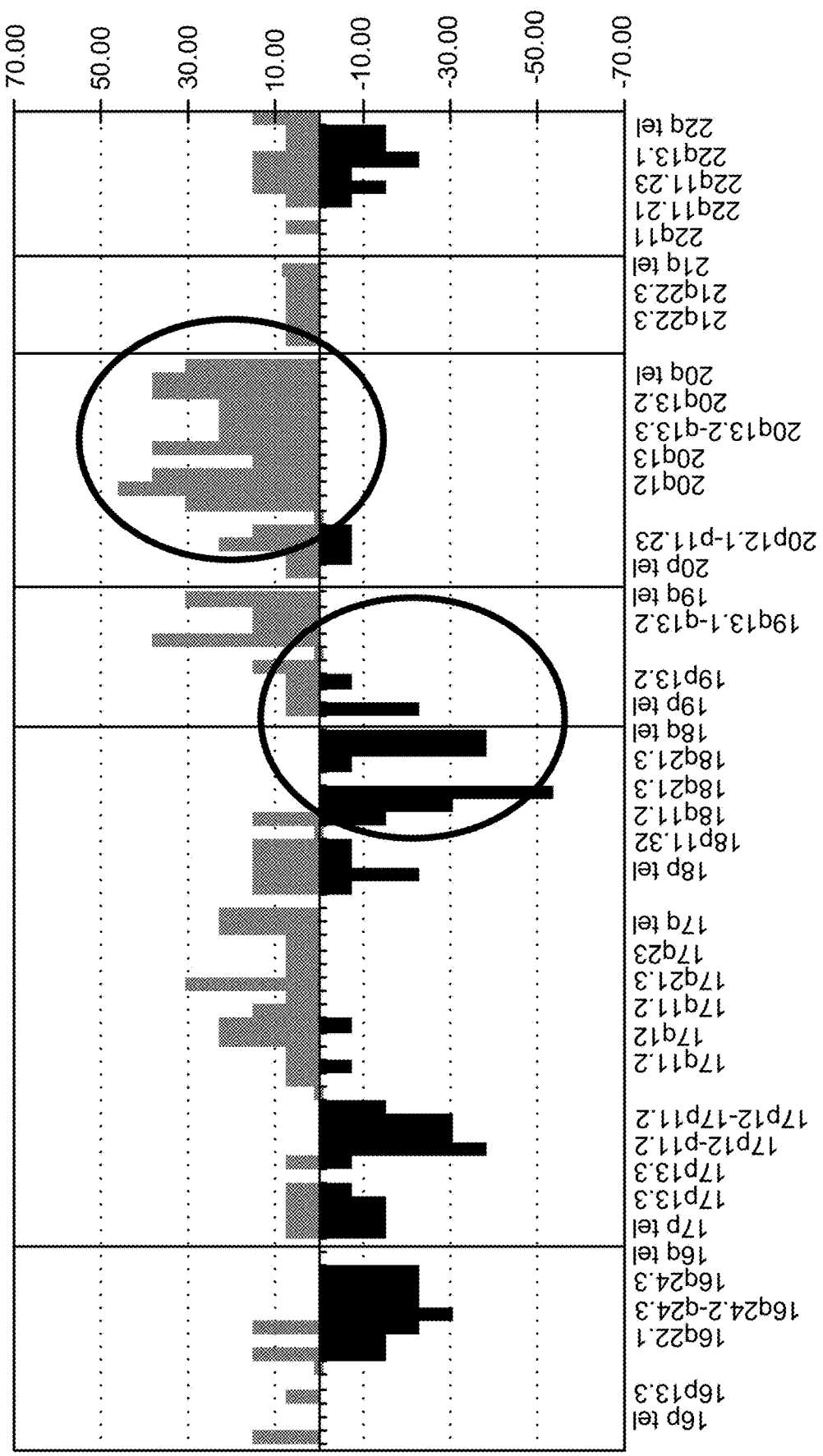

Complementation between the selected loci, in all of the tested specimens is represented in FIG. 3.

Sensitivity and specificity in tumor detection was then evaluated using JMP 8.0 statistical analysis software (SAS Institute), utilizing Fit X by Y contingency table analysis. In this analysis, all 13 loci, and groups of 10, 9 and 8 complimentary clones were evaluated. A sample was called positive when either one of the loci (at least one locus) in the group was positive.

| 1. A set of all 14 clones: | | | |
|---|---|---|---|
| Pos/Neg 14 Loci | | | |
| | Row % | NEG | POS |
| Tumor? | NORMAL | 88.89 | 11.11 |
| | TUMOR | 28.07 | 71.93 |
| Tests | | | |
| N | DF | −LogLike | RSquare (U) |
| 990 | 1 | 94.293904 | 0.1453 |
| Test | | ChiSquare | Prob > ChiSq |
| Likelihood Ratio | | 188.588 | <.0001* |
| Pearson | | 186.366 | <.0001* |
| Fisher's Exact Test | Prob | Alternative Hypothesis | |
| Left | 1.0000 | Prob(Pos/Neg 14 Loci = POS) is greater for Tumor? = NORMAL than TUMOR | |
| Right | <.0001* | Prob(Pos/Neg 14 Loci = POS) is greater for Tumor? = TUMOR than NORMAL | |
| 2-Tail | <.0001* | Prob(Pos/Neg 14 Loci = POS) is different across Tumor? | |

| 2. A representative subset of 10 clones: | | | | |
|---|---|---|---|---|
| DCC | IL6 | MYC | PTEN | TSC1 |
| FGFR2 | LAMC2 | MYCN(N-myc) | RASSF1 | UBE3A, D15S10 |

| Pos/Neg 10 | | | |
|---|---|---|---|
| | Row % | NEG | POS |
| Tumor? | NORMAL | 66.67 | 33.33 |
| | TUMOR | 26.32 | 73.68 |
| Tests | | | |
| N | DF | −LogLike | RSquare (U) |
| 924 | 1 | 37.838597 | 0.0655 |
| Test | | ChiSquare | Prob > ChiSq |
| Likelihood Ratio | | 75.677 | <.0001* |
| Pearson | | 81.670 | <.0001* |
| Fisher's Exact Test | Prob | Alternative Hypothesis | |
| Left | 1.0000 | Prob(Pos/Neg 10 = POS) is greater for Tumor? = NORMAL than TUMOR | |
| Right | <.0001* | Prob(Pos/Neg 10 = POS) is greater for Tumor? = TUMOR than NORMAL | |
| 2-Tail | <.0001* | Prob(Pos/Neg 10 = POS) is different across Tumor? | |

| 3. A representative subset of 9 clones | | |
|---|---|---|
| DCC | LAMC2 | RASSF1 |
| FGFR2 | MYC | TSC1 |
| IL6 | MYCN(N-myc) | UBE3A, D15S10 |

-continued

| Pos/Neg 9 | | | |
|---|---|---|---|
| | Row % | NEG | POS |
| Tumor? | NORMAL | 88.89 | 11.11 |
| | TUMOR | 28.07 | 71.93 |

| Tests | | | |
|---|---|---|---|
| N | DF | −LogLike | RSquare (U) |
| 924 | 1 | 88.007643 | 0.1453 |

| Test | ChiSquare | Prob > ChiSq |
|---|---|---|
| Likelihood Ratio | 176.015 | <.0001* |
| Pearson | 173.942 | <.0001* |

| Fisher's Exact Test | Prob | Alternative Hypothesis |
|---|---|---|
| Left | 1.0000 | Prob(Pos/Neg 9 = POS) is greater for Tumor? = NORMAL than TUMOR |
| Right | <.0001* | Prob(Pos/Neg 9 = POS) is greater for Tumor? = TUMOR than NORMAL |
| 2-Tail | <.0001* | Prob(Pos/Neg 9 = POS) is different across Tumor? |

| 4. A representative subset of 8 clones | | | |
|---|---|---|---|
| FGFR2 | LAMC2 | MYCN(N-myc) | TSC1 |
| IL6 | MYC | RASSF1 | UBE3A, D15S10 |

| Pos/Neg 8 | | | |
|---|---|---|---|
| | Row % | NEG | POS |
| Tumor? | NORMAL | 100.00 | 0.00 |
| | TUMOR | 29.82 | 70.18 |

| Tests | | | |
|---|---|---|---|
| N | DF | −LogLike | RSquare (U) |
| 924 | 1 | 133.24371 | 0.2151 |

| Test | ChiSquare | Prob > ChiSq |
|---|---|---|
| Likelihood Ratio | 266.487 | <.0001* |
| Pearson | 224.453 | <.0001* |

| Fisher's Exact Test | Prob | Alternative Hypothesis |
|---|---|---|
| Left | 1.0000 | Prob(Pos/Neg 8 = POS) is greater for Tumor? = NORMAL than TUMOR |
| Right | <.0001* | Prob(Pos/Neg 8 = POS) is greater for Tumor? = TUMOR than NORMAL |
| 2-Tail | <.0001* | Prob(Pos/Neg 8 = POS) is different across Tumor? |

FISH Probe Set Selection

To select 4-color probe sets for further FISH experiments, we evaluated the selected loci in greater detail supplementing statistical analysis with literature review. From the further analysis, for the probe selection, we excluded loci that were previously implicated in benign endometrial diseases. In addition, we considered NCOA3 and ZNF217 to be potentially located on one segment of rearrangement and thus picked available probe, ZNF 217, for further FISH studies.

| Clone on array: | Vysis FISH probe availability: |
|---|---|
| 1q25-q31, LAMC2 | 1q25 probe |
| 18q21.3, DCC: loss | probe available |
| 1q24, MYC | probe available |
| 10q26, FGFR2: gain (10q23 in literature) | no probe/clone PTENq23.3 |
| 15q11, UBE3A: deletion | PWS probe |
| 3q27-q29, TP63: gain (3q24-26.4 reported in literature) | 2 clones or substitute by PIK3CA |
| 3p21.3, RASSF1: gain | 2 clones |
| 7p21, IL6: gain | 1 clone |
| 2p24.1, MYCN: gain | SG, SO probes |
| 8p11.2, FGFR1: gain/deletion | 2 clones |
| 9q33-34 (TSC1): loss (found in endometriosis also) | |
| 20q12-q13 (NCOA3?): gain (in literature q13.2) 16q24.2-q24.3: loss (16q literature) | 20q11.2 HIRA, 20q13.2 ZNF217 |

As evident from the results outlined above, CGH data produced by the Genosenor array yielded several preliminary chromosomal targets which included LAMC2 (1q25), NMYC (2p24.1), PIK3CA (3q27-q29), MYC (8q24), FGFR2 (10q26), centromeric region of chromosome 18 (CEP18), DCC (18q21), and ZNF217 (20q13). Of these eight probes, numerous potential four-probe combinations have been identified and probes were grouped in probe sets.

Contingency table analysis was used to assess probe combinations, and the combinations were ranked by a chi square p value and by the DFI value. As at least some of the loci (such as DCC) represent deletions, we first assessed 3-probe combinations to allow one Chromosome Enumerator Probe (CEP) to be added to the probe set if required, as a control for a deletion probe. Shown below is the list of best 3-probe combination in detecting endometrial cancer (Table 3) with chi square p value of <0.05.

The following probe sets were selected and used in FISH experiments using Table 3 above as a guide. New probes were designed and manufactured in Abbott Molecular R&D as indicated below.

| Probe Set #1 | |
| --- | --- |
| 1q25 | SpectrumGold |
| DCC (18q21.2) | SpectrumRed |
| CEP18 | SpectrumGreen |
| MYC (8q24) | SpectrumAqua |
| Probe Set #2 | |
| MYCN (2p24.3) | SpectrumGreen (new probe) |
| PIK3CA (2q26.32) | SpectrumGold |
| FGFR2 (10q26.13) | SpectrumAqua (new probe) |
| ZNF217 (20q13.2) | pectrumRed |
| Probe Set #3 | |
| PTEN (10q23.3) | SpectrumOrange |
| CEP10 | SpectrumGreen |
| FGFR1 (8p11.2) | SpectrumAqua (new probe) |

TABLE 3

Selected best 3-probe combinations (p < 0.05)

| | | | | | Normal | | | | Cancer | | | | |
|---|---|---|---|---|---|---|---|---|---|---|---|---|---|
| PROBE 1 | PROBE 2 | PROBE 3 | # Probes | # specimens | SENS | marker (s)+ | marker (s)− | # specimens | SENS | SPEC vs norm | DFI vs norm | marker (s)+ | marker (s)− | chi sq prob |
| LAMC2:18:1q25-q31 | MYC:110:8q24.12-q24.13 | UBE3A, D15S10:182:15q11- | 3 | 9 | 0.0000 | 0 | 9 | 57 | 0.5439 | 1.0000 | 0.4561 | 31 | 26 | 0.0024 |
| LAMC2:18:1q25-q31 | FGFR1:106:8p11.2-p11.1 | UBE3A, D15S10:182:15q11- | 3 | 9 | 0.0000 | 0 | 9 | 57 | 0.5439 | 1.0000 | 0.4561 | 31 | 26 | 0.0024 |
| LAMC2:18:1q25-q31 | MYCN(N-myc):26:2p24.1 | MYC:110:8q24.12-q24.13 | 3 | 9 | 0.0000 | 0 | 9 | 57 | 0.5263 | 1.0000 | 0.4737 | 30 | 27 | 0.0032 |
| LAMC2:18:1q25-q31 | MYC:110:8q24.12-q24.13 | FGFR2:135:10q26 | 3 | 9 | 0.0000 | 0 | 9 | 57 | 0.5263 | 1.0000 | 0.4737 | 30 | 27 | 0.0032 |
| LAMC2:18:1q25-q31 | FGFR1:106:8p11.2-p11.1 | UBE3A, D15S10:182:15q11- | 3 | 9 | 0.0000 | 0 | 9 | 57 | 0.5263 | 1.0000 | 0.4737 | 30 | 27 | 0.0032 |
| LAMC2:18:1q25-q31 | MYCN(N-myc):26:2p24.1 | FGFR2:135:10q26 | 3 | 9 | 0.0000 | 0 | 9 | 57 | 0.5088 | 1.0000 | 0.4912 | 29 | 28 | 0.0043 |
| LAMC2:18:1q25-q31 | FGFR1:106:8p11.2-p11.1 | FGFR2:135:10q26 | 3 | 9 | 0.0000 | 0 | 9 | 57 | 0.5088 | 1.0000 | 0.4912 | 29 | 28 | 0.0043 |
| LAMC2:18:1q25-q31 | MYCN(N-myc):26:2p24.1 | MYC:110:8q24.12-q24.13 | 3 | 9 | 0.0000 | 0 | 9 | 57 | 0.4912 | 1.0000 | 0.5088 | 28 | 29 | 0.0056 |
| LAMC2:18:1q25-q31 | MYCN(N-myc):26:2p24.1 | FGFR2:135:10q26 | 3 | 9 | 0.0000 | 0 | 9 | 57 | 0.4737 | 1.0000 | 0.5263 | 27 | 30 | 0.0072 |
| LAMC2:18:1q25-q31 | FGFR2:135:10q26 | UBE3A, D15S10:182:15q11- | 3 | 9 | 0.0000 | 0 | 9 | 57 | 0.4737 | 1.0000 | 0.5263 | 27 | 30 | 0.0072 |
| MYC:110:8q24.12-q24.1 | FGFR1:106:8p11.2-p11.1 | ZNF217(ZABC1):254:20q13 | 3 | 9 | 0.0000 | 0 | 9 | 57 | 0.4737 | 1.0000 | 0.5263 | 27 | 30 | 0.0072 |
| LAMC2:18:1q25-q31 | MYC:110:8q24.12-q24.13 | ZNF217(ZABC1):254:20q13 | 3 | 9 | 0.0000 | 0 | 9 | 57 | 0.4737 | 1.0000 | 0.5263 | 27 | 30 | 0.0072 |
| LAMC2:18:1q25-q31 | UBE3A, D15S10:182:15q11 | ZNF217(ZABC1):254:20q13 | 3 | 9 | 0.0000 | 0 | 9 | 57 | 0.4561 | 1.0000 | 0.5439 | 26 | 31 | 0.0093 |
| LAMC2:18:1q25-q31 | FGFR2:135:10q26 | UBE3A, D15S10:182:15q11- | 3 | 9 | 0.0000 | 0 | 9 | 57 | 0.4386 | 1.0000 | 0.5614 | 25 | 32 | 0.0117 |
| LAMC2:18:1q25-q31 | MYCN(N-myc):26:2p24.1 | ZNF217(ZABC1):254:20q13 | 3 | 9 | 0.0000 | 0 | 9 | 57 | 0.4386 | 1.0000 | 0.5614 | 25 | 32 | 0.0117 |
| MYCN(N-myc):26:2p24. | FGFR1:106:8p11.2-p11.1 | FGFR2:135:10q26 | 3 | 9 | 0.1111 | 1 | 8 | 57 | 0.4211 | 1.0000 | 0.5789 | 24 | 33 | 0.0147 |
| LAMC2:18:1q25-q31 | FGFR1:106:8p11.2-p11.1 | FGFR2:135:10q26 | 3 | 9 | 0.1111 | 1 | 8 | 57 | 0.4211 | 1.0000 | 0.5789 | 24 | 33 | 0.0147 |
| MYCN(N-myc):26:2p24. | MYC:110:8q24.12-q24.13 | UBE3A, D15S10:182:15q11- | 3 | 9 | 0.0000 | 0 | 9 | 57 | 0.4035 | 1.0000 | 0.5965 | 23 | 34 | 0.0182 |
| MYCN(N-myc):26:2p24. | FGFR2:135:10q26 | UBE3A, D15S10:182:15q11- | 3 | 9 | 0.0000 | 0 | 9 | 57 | 0.3860 | 1.0000 | 0.6140 | 22 | 35 | 0.0225 |
| FGFR2:135:10q26 | UBE3A, D15S10:182:15q11 | ZNF217(ZABC1):254:20q13 | 3 | 9 | 0.0000 | 0 | 9 | 57 | 0.3860 | 1.0000 | 0.6140 | 22 | 35 | 0.0225 |
| LAMC2:18:1q25-q31 | FGFR1:106:8p11.2-p11.1 | DCC:231:18q21.3 | 3 | 9 | 0.1111 | 1 | 8 | 57 | 0.5088 | 0.8889 | 0.5036 | 29 | 28 | 0.0260 |
| LAMC2:18:1q25-q31 | MYC:110:8q24.12-q24.13 | DCC:231:18q21.3 | 3 | 9 | 0.1111 | 1 | 8 | 57 | 0.5088 | 0.8889 | 0.5036 | 29 | 28 | 0.0260 |
| LAMC2:18:1q25-q31 | FGFR2:135:10q26 | DCC:231:18q21.3 | 3 | 9 | 0.1111 | 1 | 8 | 57 | 0.3684 | 0.8889 | 0.6316 | 21 | 36 | 0.0260 |
| FGFR1:106:8p11.2-p11. | UBE3A, D15S10:182:15q11 | ZNF217(ZABC1):254:20q13 | 3 | 9 | 0.1111 | 1 | 8 | 57 | 0.3684 | 0.8889 | 0.6316 | 21 | 36 | 0.0274 |
| MYCN(N-myc):26:2p24. | FGFR2:135:10q26 | DCC:231:18q21.3 | 3 | 9 | 0.1111 | 1 | 8 | 57 | 0.4912 | 0.8889 | 0.5208 | 28 | 29 | 0.0274 |
| LAMC2:18:1q25-q31 | MYC:110:8q24.12-q24.13 | MYC:110:8q24.12-q24.13 | 3 | 9 | 0.0000 | 0 | 9 | 57 | 0.3509 | 1.0000 | 0.6491 | 20 | 37 | 0.0327 |
| MYCN(N-myc):26:2p24. | FGFR1:106:8p11.2-p11.1 | UBE3A, D15S10:182:15q11- | 3 | 9 | 0.0000 | 0 | 9 | 57 | 0.3509 | 1.0000 | 0.6491 | 20 | 37 | 0.0333 |
| FGFR1:106:8p11.2-p11. | FGFR1:106:8p11.2-p11.1 | UBE3A, D15S10:182:15q11- | 3 | 9 | 0.0000 | 0 | 9 | 57 | 0.3509 | 1.0000 | 0.6491 | 20 | 37 | 0.0333 |
| MYCN(N-myc):26:2p24. | FGFR2:135:10q26 | ZNF217(ZABC1):254:20q13 | 3 | 9 | 0.0000 | 0 | 9 | 57 | 0.3509 | 1.0000 | 0.6491 | 20 | 37 | 0.0333 |
| FGFR1:106:8p11.2-p11. | FGFR2:135:10q26 | ZNF217(ZABC1):254:20q13 | 3 | 9 | 0.0000 | 0 | 9 | 57 | 0.3333 | 1.0000 | 0.6667 | 19 | 38 | 0.0333 |
| MYCN(N-myc):26:2p24. | FGFR1:106:8p11.2-p11.1 | ZNF217(ZABC1):254:20q13 | 3 | 9 | 0.0000 | 0 | 9 | 57 | 0.3333 | 1.0000 | 0.6667 | 19 | 38 | 0.0401 |
| MYC:110:8q24.12-q24.1 | MYC:110:8q24.12-q24.13 | ZNF217(ZABC1):254:20q13 | 3 | 9 | 0.0000 | 0 | 9 | 57 | 0.3333 | 1.0000 | 0.6667 | 19 | 38 | 0.0401 |
| FGFR1:106:8p11.2-p11. | UBE3A, D15S10:182:15q11 | ZNF217(ZABC1):254:20q13 | 3 | 9 | 0.0000 | 0 | 9 | 57 | 0.3158 | 1.0000 | 0.6842 | 18 | 39 | 0.0481 |

Probe sets #1 and 2 in relation to aCGH data are shown in FIG. 4. The plot illustrates that the probes were chosen in such a manner as to be able to detect both endometrioid and non-endometrioid tumors.

Fluorescence In Situ Hybridization Studies

Study Design

A probe selection study is currently being performed to determine which four-probe combination of the eight FISH probes can most accurately detect endometrial carcinoma.

Archived formalin-fixed paraffin embedded endometrial tissue specimens taken from patients undergoing hysterectomy or Pipelle biopsy during 2000 to 2006 were utilized for this probe selection study. A variety of specimens diagnosed as endometrial carcinoma (endometrioid type and non-endometrioid type), simple and complex hyperplasia and normal endometrial epithelium were selected for FISH analysis (Table 4).

Ten histologically negative specimens from patients without a history of endometrial carcinoma were also evaluated as a normal value study. Six paraffin sectioned slides were prepared for each case, one was stained with hematoxylin and eosin (H&E) while five unstained slides were prepared for FISH analysis. The H&E slide was microscopically evaluated by a gynecologic pathologist and areas of interest (tumor in cancer specimens; normal epithelium in benign specimens) for FISH analysis were identified. This area of interest was concurrently marked on the unstained tissue slide and was hybridized with each of the two FISH probe sets (separate slides used for each of the two probe sets).

TABLE 4

Patient Population

| | Genosensor cases | Non Genosensor | Total |
|---|---|---|---|
| Normal | 0 | 10 | 10 |
| Simple Hyperplasia | 0 | 5 | 5 |
| Complex Hyperplasia | 2 | 4 | 6 |
| Endometrioid Grade 1 | 8 | 7 | 15 |
| Endometrioid Grade 2 | 7 | 3 | 10 |
| Endometrioid Grade 3 | 6 | 4 | 10 |
| Serous | 6 | 3 | 9 |
| Clear Cell | 1 | 1 | 2 |
| MMMT | 2 | 1 | 3 |
| Total | 32 | 38 | 70 |

Figure 5:
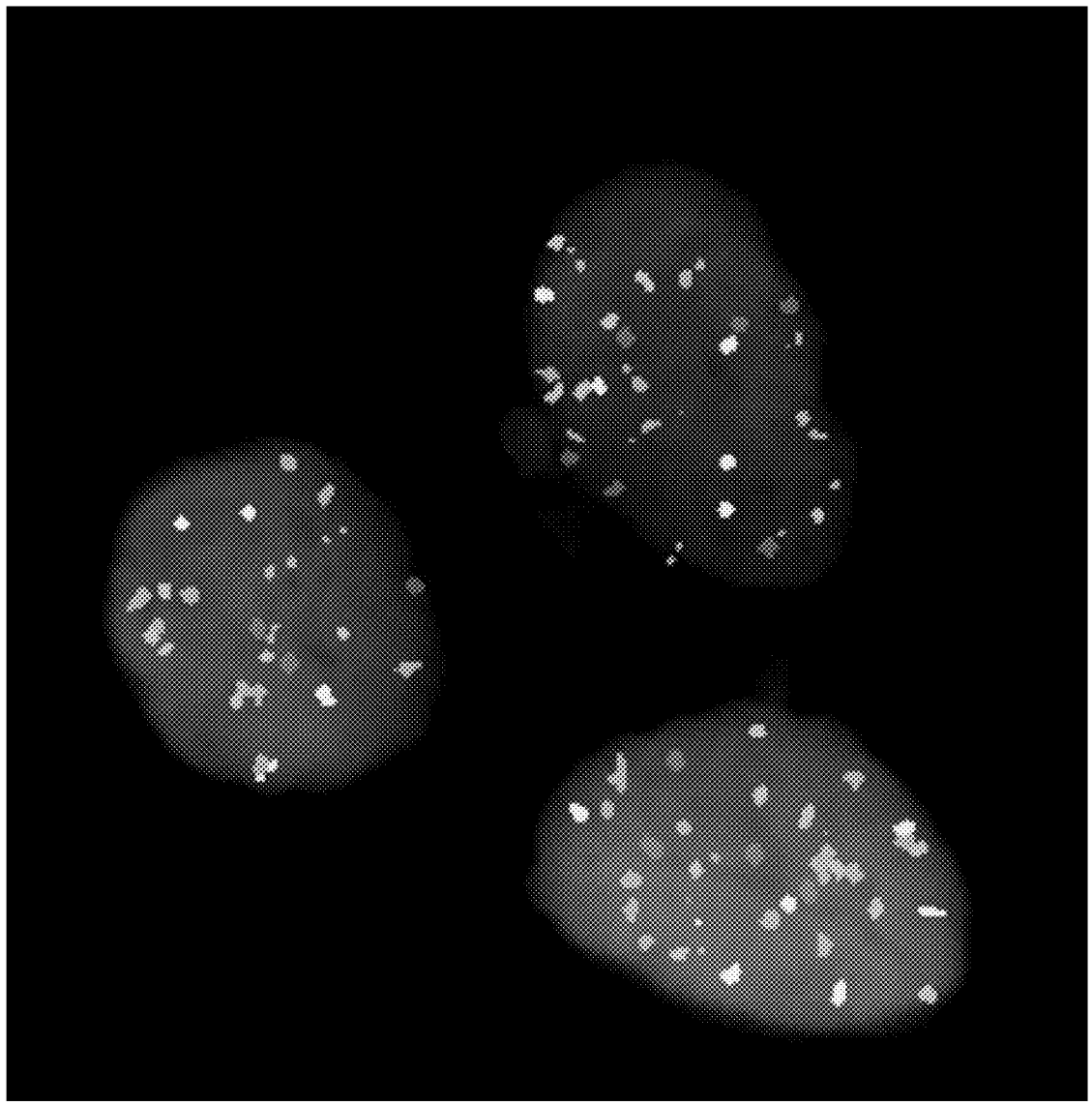
FIG. 5: Representative example of cells with FISH signals (amplification).

Hybridized slides were evaluated using a fluorescence microscope. The area of interest was identified, 50 cells were evaluated (50 tumor cells for the cancer or pre-neoplastic cases and 50 normal cells for the normal cases) and the number of signals from each of the four probes was recorded. A representative example of endometrial cancer cells exhibiting multiple gains for these probes is shown in FIG. 5. A statistical analysis was performed by Abbott Molecular, Inc. using the signal patterns from all recorded cells. The ten histologically negative specimens were used to calculate the number of signals present in normal endometrial tissue. ROC curve analyses were performed to determine the optimal cutoff values used to discriminate chromosomal abnormalities (gains and losses) from cells with normal chromosomal content for each probe analyzed. Numerous different four-probe combinations were evaluated using this technique to determine the best probe combination to distinguish endometrial cancer from normal endometrial tissue and precursor lesions.

Results

Probe Sets #1 and #2

Figure 6A:
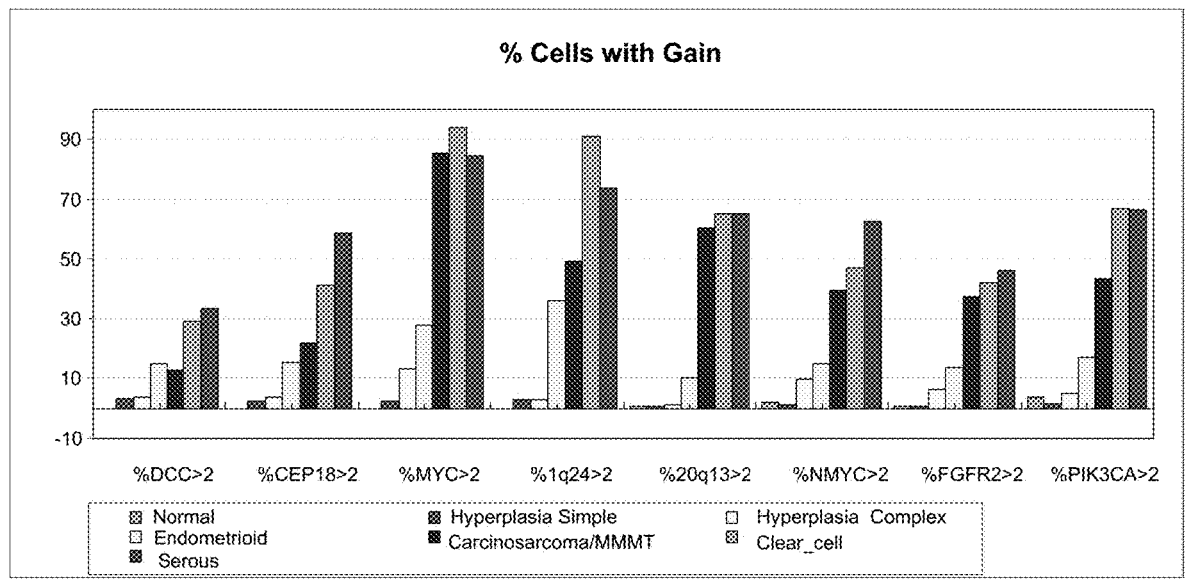
FIG. 6A-C: Probe sets 1 and 2. Average % abnormal cells in all specimens evaluated. A, % Cells with Gain; B, % Cells with Loss; C, % Cells with Gains and Losses.
Figure 6B:
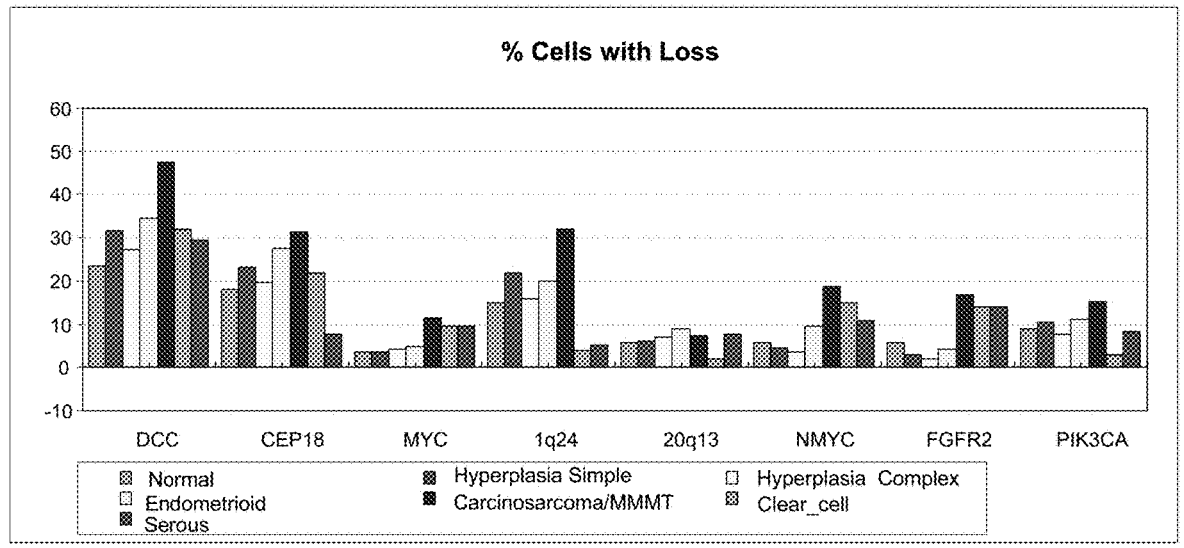
Figure 6C:
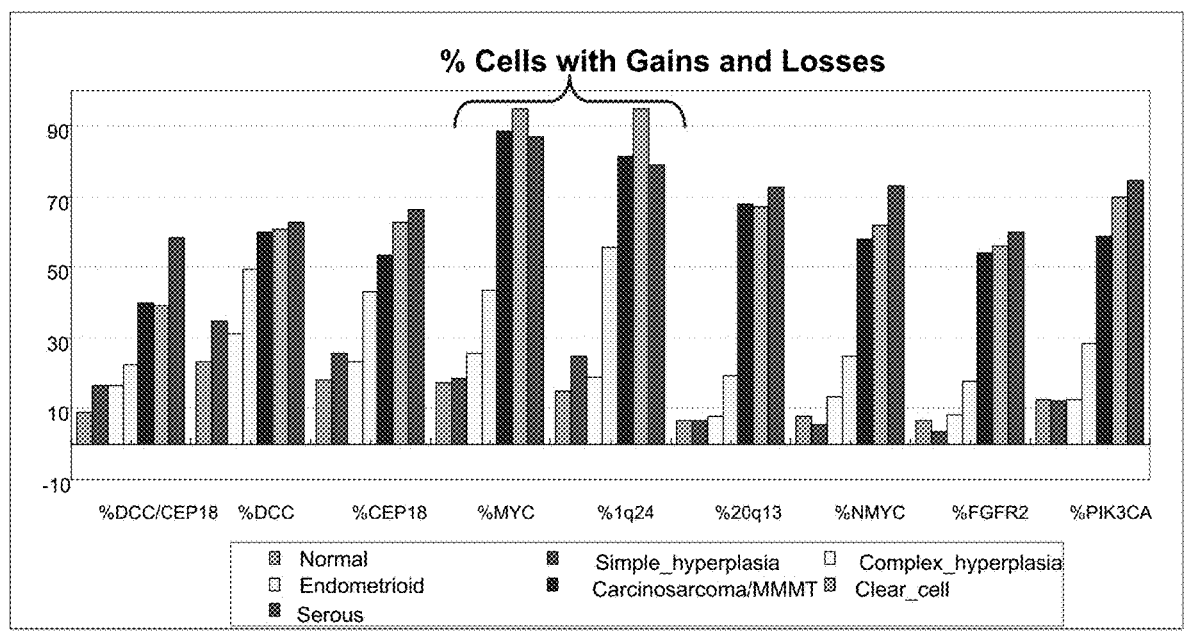

Two probe sets, #1 and #2, were evaluated on all specimens. FIG. 6 illustrates the proportion of cells with chromosomal abnormalities by histologic subtype for each of the eight probes. Normal endometrial specimens exhibited zero or very few cells with chromosomal gains and approximate 5-20% of cells showed a form of chromosomal loss. In additional very few (<10%) cells with chromosomal gains were identified in hyperplasia specimens.

The following FISH parameters were analyzed:

1. % Gain, percent of cells with a copy number gain (>2 copies per cell) of a locus out of 50 cells counted (50=100%)
2. % Loss, percent of cells with a copy number loss (<2 copies per cell) of a locus out of 50 cells counted (50=100%)
3. % Abnormal, percent of cells with either a copy number loss (<2 copies per cell) OR a copy number gain (>2 copies per cell) of a locus out of 50 cells counted (50=100%)

The conclusions drawn from FIG. 6 are: No gains were observed in Normal specimens for DCC, CEP18, MYC and 1q24. The increase in % cells with gains was observed from normal to hyperplasia to cancer, with most gains in Non-Endometrioid tumors. With losses, there is no clear separation between normal, hyperplasia and cancer. A trend is observed in the increase of % Abnormal from normal to hyperplasia to cancer, with the greatest number of abnormalities in Non-Endometrioid tumors. MYC and 1q24 appear to have the largest range of difference.

Probes directed to 1q25 and 8q24 had the highest percentage of abnormal cells in specimens with EN and NE cancers. All other probes detected approximately the same proportion of cells with gains in EN and NE cancers. For chromosomal losses, 18q (DCC) and CEP 18 exhibited the most cells with loss in EN and NE cancers, as well as normal and hyperplasia specimens.

A multivariate analysis was performed to determine which four-probe combination yielded the great combination of sensitivity and specificity for NE and NE cancers. Using JMP 8.0 Statistical Analysis software (SAS Institute, 2008) 70 4-probe combinations of 8 probes were tested. "% Abnormal" was chosen as FISH parameter for analysis (see definitions) and Nominal Logistic Regression platform was utilized with the Test specimens chosen as "all cancers" and Control specimens as hyperplasia+normal. ROCs were constructed, and 20 best combinations with the highest AUC were selected. The combinatorial Excel program was run on the selected combinations to obtain high-resolution data on sensitivity and specificity. The program constructed contingency tables and calculated DFI values for the 4-probe combinations at each cutoff level of % "abnormal" for each probe.

The results of these analyses revealed numerous possible candidate four-probe sets (Table 5). The best probe set combination included DCC, 1q24, MYC, and CEP18 which had a AUC of 0.952 with a sensitivity of 1.000 and a specificity of 0.9048. Three other combinations had a sensitivity of 0.979 and a specificity of 0.900 which included (set 2) 1q24, MYC, FGFR2, CEP18, (set 3) DCC, 1q24, FGFR2, CEP18, and (set 4) 1q24, MYC, CEP18 and PIK3CA.

TABLE 5

Probe combinations that discriminate Cancer from Normal and Hyperplasia. Analyzed % Cells with any abnormality (% abnormal) using JMP8.0 with combinatorial Excel program (contingency table analysis).

| Locus 1 | Locus 2 | Locus 3 | Locus 4 | AUC (JMP) | Best Sens LM | Best Spec LM |
|---|---|---|---|---|---|---|
| DCC | 1q24 | MYC | CEP18 | 0.95238 | 1.0000 | 0.9048 |
| 1q24 | MYC | FGFR2 | CEP18 | 0.95918 | 0.9796 | 0.9000 |
| DCC | 1q24 | FGFR2 | CEP18 | 0.95867 | 0.9796 | 0.9000 |
| 1q24 | MYC | CEP18 | PIK3CA | 0.95306 | 0.9796 | 0.9000 |
| DCC | 1q24 | MYC | FGFR2 | 0.95714 | 0.9592 | 0.9000 |
| 1q24 | NMYC | FGFR2 | CEP18 | 0.95714 | 0.9592 | 0.9000 |
| 1q24 | FGFR2 | CEP18 | PIK3CA | 0.95714 | 0.9592 | 0.9000 |
| 1q24 | FGFR2 | CEP18 | 20q13 | 0.95612 | 0.9592 | 0.9000 |
| 1q24 | CEP18 | PIK3CA | 20q13 | 0.95612 | 0.9592 | 0.9000 |
| 1q24 | NMYC | CEP18 | PIK3CA | 0.9551 | 0.9592 | 0.9000 |
| DCC | 1q24 | FGFR2 | 20q13 | 0.95408 | 0.9388 | 0.9000 |
|  | 1q24 | MYC | CEP18 |  | 0.9796 | 0.9048 |
| DCC | 1q24 |  | CEP18 |  | 0.9796 | 0.9048 |
|  | 1q24 |  | CEP18 |  | 0.9592 | 0.9048 |

Test = all cancers;
Control = hyperplasia + normal

Figure 7:
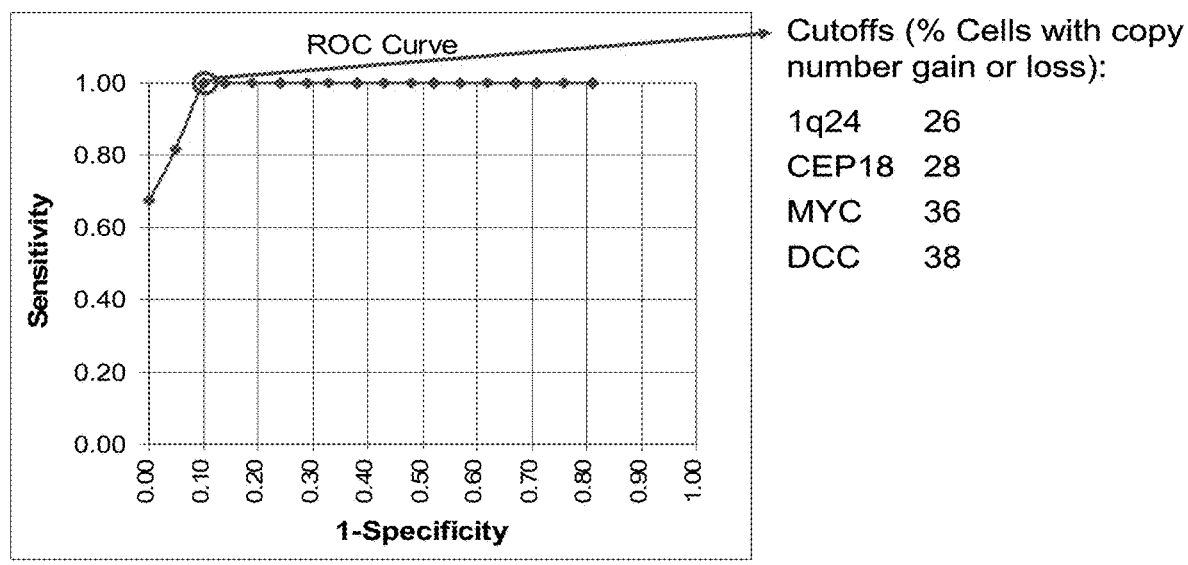
FIG. 7: ROC Curve for CEP18+1q24+MYC+DCC, % Abnormal (% cells with either copy number gain or copy number loss for at least 1 of 4 loci).
Figure 8:
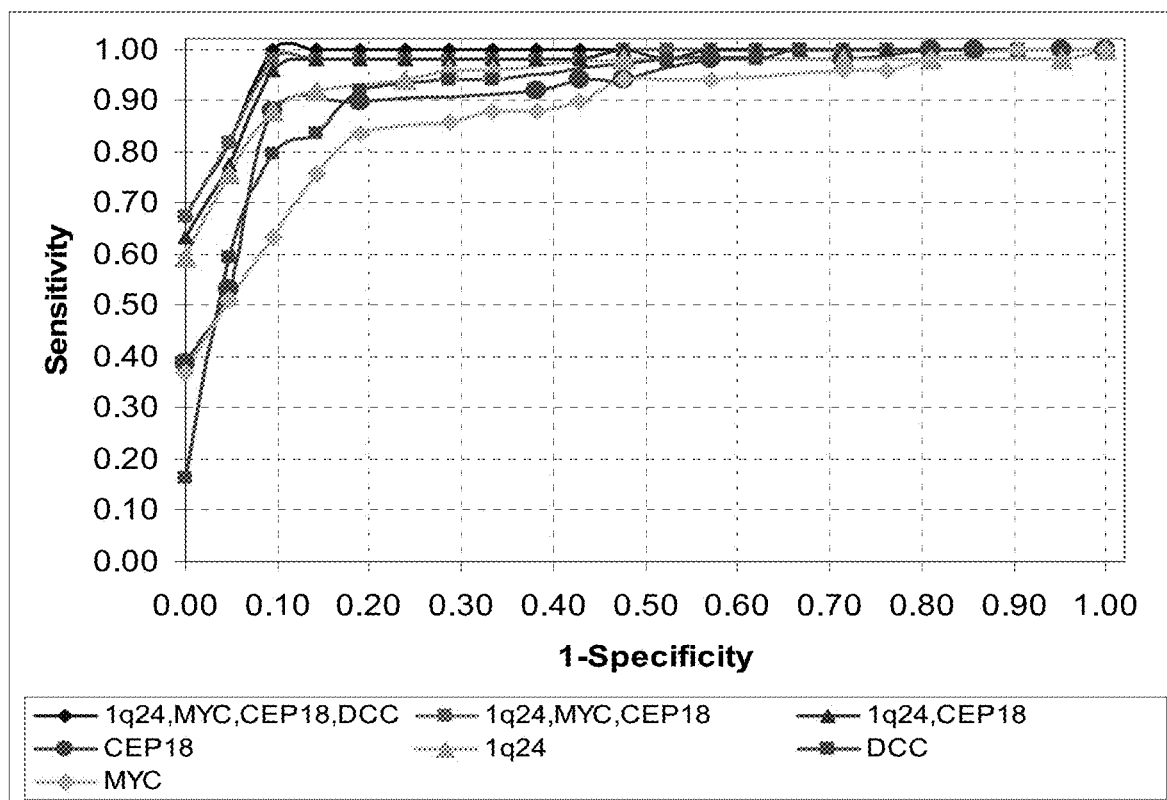
FIG. 8: Individual Probes and Combinations (ROC Curves, % Abnormal).

FIGS. 7 and 8 present Receiver Operator curves for the selected probe combination. It is evident from the figures that adding probes to a single-probe FISH assay improves sensitivity and specificity.

The distribution by tumor type and grade is shown below (Table 6):

TABLE 6

Tumor Type and Grade By FISH (4Best) % Abnormal: POS or NEG. Cutoffs used as listed in FIG. 7.

| Count Row % | NEG | POS | Total |
|---|---|---|---|
| Normal | 10 | 0 | 10 |
|  | 100.00 | 0.00 |  |
| Simple hyperplasia | 4 | 1 | 5 |
|  | 80.00 | 20.00 |  |
| Complex hyperplasia | 5 | 1 | 6 |
|  | 83.33 | 16.67 |  |
| Endometrioid Grade 1 | 0 | 15 | 15 |
|  | 0.00 | 100.00 |  |
| Endometrioid Grade 2 | 0 | 10 | 10 |
|  | 0.00 | 100.00 |  |
| Endometrioid Grade 3 | 0 | 10 | 10 |
|  | 0.00 | 100.00 |  |
| Carcinosarcoma/MMMT | 0 | 3 | 3 |
|  | 0.00 | 100.00 |  |
| Clear cell | 0 | 2 | 2 |
|  | 0.00 | 100.00 |  |
| Serous | 0 | 9 | 9 |
|  | 0.00 | 100.00 |  |
|  | 19 | 51 | 70 |

Detection of positives in the complex hyperplasia specimens could be due to heterogeneity in this category and could reflect risk of progression to cancer.

Comparison of FISH to CGH Array Data

Performance of the 1q24, CEP16, DCC and MYC FISH probe set was compared by contingency analysis in JMP 8.0 to the aCGH Probe Selection Set #1:

DCC (18q21.3)—frequency of loss in all cancers~17%
Cep18 included for FISH probe set (detection of deletions)
LAMC2 (1q25)—frequency of gain in all cancers >20%
MYC (8q24.12-q24.13)—frequency of gain in all cancers~17%

Contingency Table Array (Ca vs N)
One of Loci Changed

| Count Row % |  | NEG | POS |  |
|---|---|---|---|---|
| Ca/NoCa | Ca | 28 | 29 | 57 |
|  |  | 49.12 | 50.88 |  |
|  | N | 8 | 1 | 9 |
|  |  | 88.89 | 11.11 |  |
|  |  | 36 | 30 | 66 |

Sensitivity = 50.88% (29 out of 57)
Specificity = 88.89% (8 out of 9)

Contingency Table FISH (Ca vs N + Hyperplasia)
FISH (4Best) % Imbal: POS or NEG

| Count Row % |  | NEG | POS |  |
|---|---|---|---|---|
| Test or Ref? | Ca | 0 | 49 | 49 |
|  |  | 0.00 | 100.00 |  |
|  | N + Hyperpl | 19 | 2 | 21 |
|  |  | 90.48 | 9.52 |  |
|  |  | 19 | 51 | 70 |

Sensitivity = 100% (49 out of 49)
Specificity = 90.48% (19 out of 21)

It is apparent that FISH assay with probe designed based on microarray results has significantly improved on array performance. This is possibly due to influence of benign cells in the macro-dissected tumors that dilute the analyte tumor DNA and thus lead to lower sensitivity. This problem in microarray experiments could be overcome by careful selection of specimens with high percentage of tumor cells and by micro-dissection of the tumor area.

Analysis of Copy Number Gains Only, Best Combinations: Cancer Vs Normal+Hyperplasia For a practical FISH application, an alternative probe combination was evaluated that avoids technically challenging detection of losses (looses and gains are considered in "% abnormal" parameter).

Figure 9:
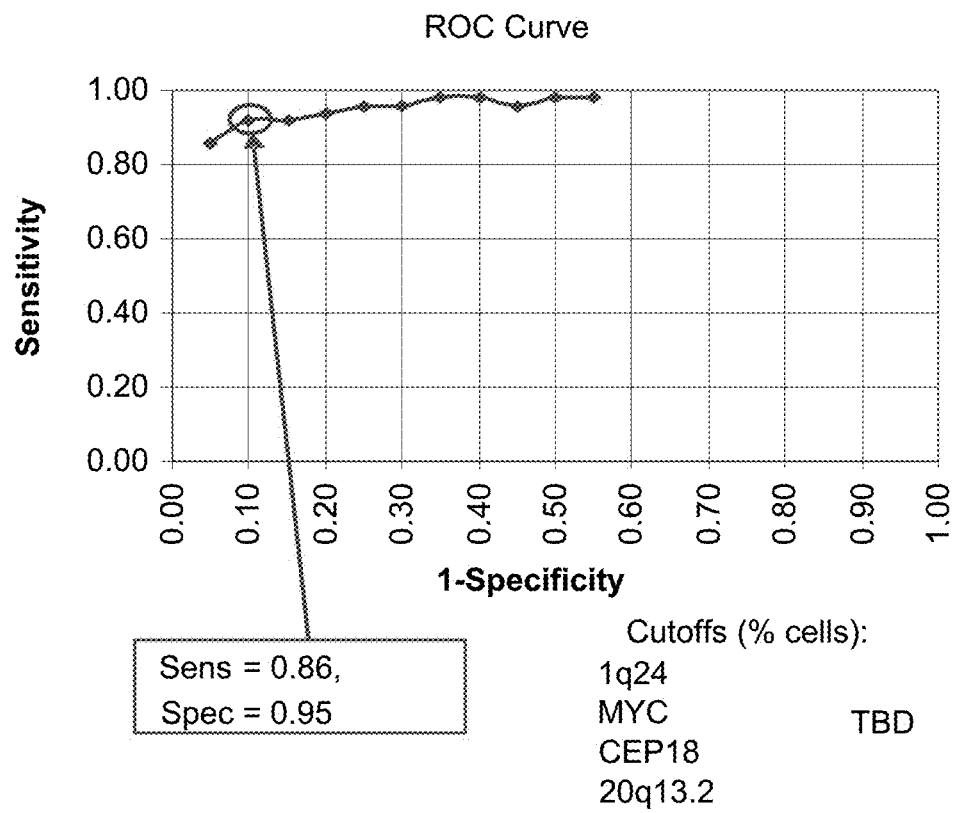
FIG. 9: ROC Curves, 4-Probe Combination, Gains of 1q24, MYC, CEP18 and 20q13.2.

Following the procedure outlined above, all 4-probe combinations were analyzed, and best were selected (preliminary analysis using SD of % Cells in excel), Table 7 and FIG. 9.

TABLE 7

Best 4-probe combinations, Gains only.

| PROBE 1 | PROBE 2 | PROBE 3 | PROBE 4 | SENS | SPEC | DFI | CUTOFF 1 | CUTOFF 2 | CUTOFF 3 | CUTOFF 4 |
|---|---|---|---|---|---|---|---|---|---|---|
| 1q24 | MYC | CEP18 | 20q13.2 | 0.84 | 0.95 | 0.17 | 41.30 | 8.36 | 7.91 | 4.46 |
| 1q24 | CEP18 | PIK3CA | 20q13.2 | 0.84 | 0.95 | 0.17 | 8.36 | 7.91 | 18.47 | 4.46 |
| 1q24 | CEP18 | 20q13.2 | FGFR2 | 0.84 | 0.90 | 0.19 | 8.36 | 7.91 | 4.46 | 15.71 |

Interestingly, the combinations listed above have improved on specificity of cancer detection but have decreased sensitivity, especially to early-stage endometrioid tumors (FIG. 9 and Table 8).

The distribution of positive and negative specimens using the 1q24, MYC, CEP18 and 20q13 probe set is shown in Table 8.

TABLE 8

Tumor Type and Grade By FISH: Gains of MYC, CEP18, 1q24, 20q13. Cutoffs used as listed in FIG. 9.

| Count<br>Row % | NEG | POS | Total |
|---|---|---|---|
| Normal | 10 | 0 | 10 |
|  | 100.00 | 0.00 |  |
| Simple hyperplasia | 4 | 1 | 5 |
|  | 80.00 | 20.00 |  |
| Complex hyperplasia | 5 | 1 | 6 |
|  | 83.33 | 16.67 |  |
| Endometrioid Grade 1 | 3 | 12 | 15 |
|  | 20.00 | 80.00 |  |
| Endometrioid Grade 2 | 1 | 9 | 10 |
|  | 10.00 | 90.00 |  |
| Endometrioid Grade 3 | 0 | 10 | 10 |
|  | 0.00 | 100.00 |  |
| Carcinosarcoma/MMMT | 0 | 3 | 3 |
|  | 0.00 | 100.00 |  |
| Clear cell | 0 | 2 | 2 |
|  | 0.00 | 100.00 |  |
| Serous | 0 | 9 | 9 |
|  | 0.00 | 100.00 |  |
|  | 23 | 47 | 70 |

As evident from the table, this set (FISH gains) has lower sensitivity towards low-grade endometrial tumors.

Probe Set #3 Evaluation

Probe set #3 was evaluated on 16 early-stage endometrioid cancer specimens and 12 benign (normal and hyperplasia) specimens to determine whether it improves on sensitivity of detection of early-stage (grade 1 and 2) endometrioid tumors with the FISH assay that evaluates gains of MYC, CEP18, 1q24, 20q13.

The analysis of the FISH data has demonstrated that the addition of the PTEN loss to the selected probe set at a cutoff of 14% could increase the sensitivity of detection of endometrial cancer to 100%, however decreasing the specificity (FIG. 10). This finding is in agreement with aCGH data discussed above. In contrast, an addition of Chromosome 10 "% abnormal cells" to the selected probes at a cutoff of 10-12% of cells with any abnormality (gain or loss), allowed for increased sensitivity without sacrificing the specificity. Interestingly, a combination of CEP10 with MYC, CEP18, and 1q24 yielded the same 100% sensitivity for the 16 cancer specimens and 92% specificity against 12 normal+ hyperplasia specimens. Therefore, an added assessment of aneusomy 10 to the FISH probe set could be a beneficial. Addition of FGFR1 did not significantly improve cancer detection, however, when used in combination with CEP10, 1q24 and MYC probes, FGFR1 gain at a cutoff of 2% cells yielded 100% sensitivity for the 16 cancer specimens and 92% specificity against 12 normal+hyperplasia specimens. However, when all the 70 specimens are considered (with limited data included for the probe set #3), the only probe that did not result in decrease in specificity when combined with the MYC, 1q24, 20q13, and CEP18 gain probes was FGFR1 at the cutoff of ≥2% cells with gain of the probe:

Test or Ref? By MYC gain, 1q24 gain, 20q13 gain, CEP18 gain, FGFR1 gain:

| Count<br>Row % | NEG | POS | Total |
|---|---|---|---|
| Ca | 2 | 47 | 49 |
|  | 4.08 | 95.92 |  |
| N + Hyperpl | 19 | 2 | 21 |
|  | 90.48 | 9.52 |  |
|  | 21 | 49 | 70 |

Interestingly though, a combination of 20q13.2, 1q24, CEP10 and FGFR1 on all 70 specimens (with the data available thus far) demonstrated sensitivity and specificity of 96% and 91%, as shown below:

Test or Ref? By 20q13, CEP10, 1q24, FGFR1

| Count<br>Row % | NEG | POS | Total |
|---|---|---|---|
| Ca | 2 | 47 | 49 |
|  | 4.08 | 95.92 |  |
| N + Hyperpl | 19 | 2 | 21 |
|  | 90.48 | 9.52 |  |
|  | 21 | 49 | 70 |

As data for all of the specimens is unavailable at this point for Probe Set #3, it appears feasible that the combination of 4 probes that evaluate 20q13 gain, 1q24 gain, CEP10 imbalance, and FGFR1 gain could prove to be superior to the 1q24, MYC, CEP8 and 20q13.2 probe set in future experiments.

Probe Set #4 Evaluation

Probe set #4 was evaluated on the same set of endometrioid cancer specimens, normal and hyperplasia specimens described above to determine whether it improves on sensitivity of detection of low grade (grade 1 and 2) endometrioid tumors above that obtained with the FISH assay that evaluates gains of MYC, CEP18, 1q25, 20q13.

The analysis of the FISH data demonstrates that the substitution of the FGFR1 gain (with a cutoff of 4%) for 20q in the MYC, 1q25, and CEP18 probe set provided a sensitivity of 90%, which was similar to the MYC, 1q25, CEP18 and 20q probe set. However, the addition of FGFR1, resulted in one additional complex hyperplasia specimen to be diagnosed as positive. (Table 9).

Interestingly, further analyses revealed that FGFR1 could significantly increase the sensitivity of the four probe set over 20q. When the cutoff of FGFR1 was reduced to 2%, the probe combination of FGFR1, MYC, 1q25, and CEP18 had a sensitivity and specificity of 96% and 81% respectively.

TABLE 9

Evaluation of additional probes (probe set 3) to improve sensitivity of endometrial cancer detection over that obtained with MYC, CEP 18, 1q25 and 20q13.

| ID# | Type and Grade | MYC % Gain >4 | CEP18 % Gain >4 | 1q25 % Gain >6 | 20q13.2 % Gain >4 | FGFR1 % Gain >4 | FGFR1 % Gain >2 | DCC/ CEP18 % Loss >16 | PTEN/ CEP10 % Loss >12 | PTEN % Loss >18 | CEP10 % Loss >10 | FGFR1 % Gain OR Loss >10 |
|---|---|---|---|---|---|---|---|---|---|---|---|---|
| 101 | N | NEG | NEG | NEG | NEG | NEG | NEG | NEG | NEG | NEG | NEG | NEG |
| 102 | N | NEG | NEG | NEG | NEG | NEG | NEG | NEG | NEG | NEG | NEG | POS |
| 103 | N | NEG | NEG | NEG | NEG | NEG | NEG | NEG | NEG | NEG | NEG | NEG |
| 104 | N | NEG | NEG | NEG | NEG | NEG | NEG | POS | NEG | NEG | NEG | NEG |
| 105 | N | NEG | NEG | NEG | NEG | NEG | NEG | NEG | NEG | NEG | NEG | NEG |
| 106 | N | NEG | NEG | NEG | NEG | NEG | NEG | NEG | NEG | NEG | NEG | NEG |
| 107 | N | NEG | NEG | NEG | NEG | NEG | NEG | NEG | NEG | NEG | NEG | NEG |
| 108 | N | NEG | NEG | NEG | NEG | NEG | NEG | NEG | NEG | NEG | NEG | NEG |
| 109 | N | NEG | NEG | NEG | NEG | NEG | NEG | NEG | NEG | NEG | NEG | NEG |
| 110 | N | NEG | NEG | NEG | NEG | NEG | NEG | NEG | NEG | POS | POS | NEG |
| 86 | SH | NEG | NEG | NEG | NEG | NEG | NEG | POS | NEG | POS | POS | NEG |
| 88 | SH | POS | POS | POS | NEG | NEG | NEG | NEG | NEG | NEG | NEG | NEG |
| 96 | SH | NEG | NEG | NEG | NEG | NEG | NEG | NEG | NEG | NEG | NEG | NEG |
| 97 | SH | NEG | NEG | NEG | NEG | NEG | NEG | NEG | NEG | NEG | NEG | NEG |
| 100 | SH | NEG | NEG | NEG | NEG | NEG | NEG | NEG | NEG | NEG | NEG | NEG |
| 85 | CH | POS | POS | NEG | NEG | POS | POS | POS | POS | POS | POS | NEG |
| 87 | CH | NEG | NEG | NEG | NEG | NEG | NEG | NEG | NEG | NEG | NEG | NEG |
| 89 | CH | NEG | NEG | NEG | NEG | NEG | NEG | NEG | NEG | NEG | NEG | NEG |
| 90 | CH | NEG | NEG | NEG | NEG | POS | POS | NEG | NEG | NEG | NEG | POS |
| 91 | CH | NEG | NEG | NEG | NEG | POS | NEG | POS | NEG | NEG | NEG | NEG |
| 93 | CH | NEG | NEG | NEG | NEG | NEG | NEG | NEG | NEG | NEG | NEG | NEG |
| 2 | EG1 | NEG | NEG | NEG | NEG | NEG | NEG | POS | NEG | POS | POS | POS |
| 3 | EG1 | POS | POS | POS | NEG | NEG | NEG | NEG | NEG | NEG | POS | NEG |
| 4 | EG1 | POS | POS | POS | POS | POS | NEG | NEG | NEG | NEG | NEG | NEG |
| 5 | EG1 | POS | POS | POS | POS | POS | POS | NEG | NEG | NEG | POS | NEG |
| 14 | EG1 | POS | POS | POS | POS | POS | POS | NEG | NEG | NEG | NEG | POS |
| 15 | EG1 | NEG | NEG | NEG | POS | POS | NEG | POS | NEG | NEG | POS | POS |
| 16 | EG1 | NEG | NEG | NEG | NEG | POS | POS | POS | NEG | POS | POS | NEG |
| 18 | EG1 | POS | POS | POS | NEG | NEG | NEG | POS | NEG | NEG | NEG | NEG |
| 56 | EG1 | NEG | NEG | NEG | NEG | NEG | NEG | POS | NEG | POS | POS | NEG |
| 57 | EG1 | POS | NEG | NEG | NEG | NEG | NEG | NEG | NEG | POS | POS | NEG |
| 58 | EG1 | NEG | POS | NEG | POS | NEG | POS | NEG | NEG | NEG | POS | NEG |
| 59 | EG1 | NEG | NEG | POS | NEG | NEG | NEG | NEG | NEG | POS | POS | NEG |
| 61 | EG1 | NEG | POS | NEG | NEG | NEG | NEG | NEG | POS | NEG | POS | NEG |
| 63 | EG1 | POS | POS | POS | NEG | NEG | NEG | NEG | NEG | NEG | NEG | NEG |
| 65 | EG1 | NEG | POS | NEG | NEG | NEG | POS | NEG | NEG | POS | POS | NEG |
| 7 | EG2 | POS | POS | POS | NEG | NEG | POS | NEG | NEG | NEG | NEG | NEG |
| 8 | EG2 | POS | POS | NEG | NEG | NEG | NEG | NEG | NEG | NEG | NEG | NEG |
| 33 | EG2 | POS | POS | POS | NEG | NEG | NEG | POS | NEG | POS | POS | NEG |
| 34 | EG2 | POS | NEG | NEG | NEG | POS | POS | NEG | NEG | NEG | NEG | POS |
| 35 | EG2 | POS | POS | POS | NEG | POS | NEG | NEG | NEG | NEG | NEG | POS |
| 36 | EG2 | POS | POS | POS | POS | POS | POS | NEG | POS | NEG | NEG | POS |
| 37 | EG2 | POS | POS | POS | NEG | NEG | NEG | NEG | NEG | POS | POS | NEG |
| 66 | EG2 | POS | POS | POS | POS | POS | NEG | POS | POS | POS | POS | NEG |
| 67 | EG2 | NEG | NEG | NEG | NEG | POS | NEG | NEG | NEG | NEG | NEG | NEG |
| 70 | EG2 | POS | POS | POS | NEG | POS | POS | POS | NEG | POS | POS | POS |
| 9 | EG3 | POS | POS | POS | NEG | NEG | POS | POS | NEG | POS | POS | NEG |
| 42 | EG3 | POS | POS | POS | POS | POS | NEG | POS | NEG | NEG | NEG | POS |
| 43 | EG3 | POS | POS | POS | POS | POS | POS | POS | NEG | NEG | NEG | POS |
| 44 | EG3 | POS | POS | POS | NEG | POS | NEG | NEG | NEG | NEG | NEG | NEG |
| 45 | EG3 | POS | POS | POS | POS | POS | POS | NEG | NEG | NEG | NEG | POS |
| 47 | EG3 | POS | POS | POS | POS | POS | POS | POS | POS | POS | NEG | POS |
| 75 | EG3 | POS | POS | POS | POS | POS | POS | NEG | NEG | NEG | NEG | POS |
| 76 | EG3 | POS | NEG | POS | POS | NEG | POS | POS | POS | POS | POS | POS |
| 77 | EG3 | POS | POS | POS | POS | POS | POS | NEG | POS | NEG | NEG | POS |
| 83 | EG3 | POS | POS | POS | POS | POS | POS | NEG | NEG | NEG | POS | POS |
| 11 | C/M | POS | NEG | NEG | POS | POS | POS | NEG | POS | POS | POS | POS |
| 12 | C/M | POS | POS | POS | POS | POS | POS | POS | POS | POS | POS | POS |

TABLE 9-continued

Evaluation of additional probes (probe set 3) to improve sensitivity of endometrial cancer detection over that obtained with MYC, CEP 18, 1q25 and 20q13.

| ID# | Type and Grade | MYC % Gain >4 | CEP18 % Gain >4 | 1q25 % Gain >6 | 20q13.2 % Gain >4 | FGFR1 % Gain >4 | FGFR1 % Gain >2 | DCC/ CEP18 % Loss >16 | PTEN/ CEP10 % Loss >12 | PTEN % Loss >18 | CEP10 % Loss >10 | FGFR1 % Gain OR Loss >10 |
|---|---|---|---|---|---|---|---|---|---|---|---|---|
| 78 | C/M | POS | POS | POS | POS | POS | POS | POS | POS | NEG | NEG | POS |
| 54 | Clear cell | POS | POS | POS | POS | POS | POS | NEG | POS | NEG | NEG | POS |
| 81 | Clear cell | POS | POS | POS | POS | POS | POS | POS | POS | NEG | NEG | POS |
| 1 | S | POS | POS | POS | POS | POS | POS | POS | POS | NEG | POS | POS |
| 6 | S | POS | POS | POS | POS | POS | POS | POS | POS | NEG | NEG | POS |
| 10 | S | POS | POS | POS | POS | POS | POS | POS | POS | NEG | NEG | POS |
| 49 | S | POS | POS | POS | POS | POS | POS | POS | POS | NEG | NEG | POS |
| 50 | S | POS | POS | POS | POS | POS | POS | NEG | NEG | NEG | NEG | POS |
| 51 | S | POS | POS | POS | POS | POS | POS | POS | POS | NEG | NEG | POS |
| 79 | S | POS | POS | POS | POS | POS | POS | POS | POS | NEG | NEG | POS |
| 80 | S | POS | POS | POS | POS | POS | POS | POS | POS | NEG | NEG | POS |
| 94 | S | POS | POS | POS | POS | POS | POS | POS | POS | NEG | POS | POS |

Table Abbreviations:
N = Normal;
SH = Simple hyperplasia;
CH = Complex hyperplasia;
EG1 = Endometrioid Grade 1;
EG2 = Endometrioid Grade 2;
EG3 = Endometrioid Grade 3;
Carcinosarcoma/MMMT = C/M;
S = Serous;
POS = Number of cells with abnormal sign patterns identified met or exceeded the threshold for the probe;
NEG = Number of cells with abnormal sign patterns identified was less than the threshold for the probe Analyses of other probes to increase the sensitivity of MYC, 1q25 and CEP18 are shown in Table 10. The addition of DCC, CEP10, PTEN, or FGFR1 increase the sensitivity of the combination probe set to 94-98%. However, the increase in sensitivity was achieved at the expense of decreased specificity (76-81%).

TABLE 10

Analysis of adding DCC, CEP10, PTEN or FGFR1 to a probe set of MYC, 1q25 and CEP18 to increase the sensitivity of endometrial cancer detection

| | Gains | | | Losses Probe 4 | Sensitivity | Specificity |
|---|---|---|---|---|---|---|
| | Probe 1 | Probe 2 | Probe 3 | | | |
| Cutoff | MYC >4 | 1q25 >6 | CEP18 >4 | DCC/CEP18 >16 | 98% | 76% |
| Cutoff | MYC >4 | 1q25 >6 | CEP18 >4 | CEP10 >10 | 98% | 81% |
| Cutoff | MYC >4 | 1q25 >6 | CEP18 >4 | PTEN >18 | 96% | 81% |
| Cutoff | MYC >4 | 1q25 >6 | CEP18 >4 | FGFR1 >10 (gains and loss) | 94% | 81% |

Additional analyses were performed to determine the optimal probe set with cutoffs to attain very high specificity for endometrial carcinoma. Results from this analysis can be seen in Table 11. Numerous probe and abnormality combinations achieved at least 95% specificity. Those that produced the highest sensitivity with greater than 95% specificity are highlighted in yellow at the top of Table 11. All of these combinations included the evaluation of locus loss or combination of loss and gains (imbal). The best performing probe set that only evaluated gains had a sensitivity of 84% and specificity of 95%, which included FGFR1, 1q25, CEP18 and 20q13 with cutoffs of 8%, 8%, 8% and 8% respectively (highlighted in blue). Two other probe sets containing 1q25, MYC, CEP18 and FGFR1 or 20q13 using cutoffs of 12%, 12%, 12%, and 12%, respectively, achieved a sensitivity of 80% and specificity of 95% (highlighted in green).

The most appealing probe set included 4 LSI probes of 1q25, MYC, FGFR1 and 20q13 using similar cutoffs also had a sensitivity and specificity of 80% and 95%, respectively (seen in red). This probe set is ideal due because it performs nearly as well as other probe sets while only analyzing specimens for chromosomal gains. Chromosomal gains are easier to identify by technologists and would likely have a higher inter-observer reproducibility than when evaluating chromosomal losses.

TABLE 11

Analysis of different probes and cutoffs to achieve specificity of >95% for endometrial cancer detection

| PROBE 1 | | | PROBE 2 | | | PROBE 3 | | | PROBE 4 | | | | |
|---|---|---|---|---|---|---|---|---|---|---|---|---|---|
| Probe | Abn | Cut off | Probe | Abn | Cut off | Probe | Abn | Cut off | Probe | Abn | Cut off | SENS | SPEC |
| PTEN/CEP10 | loss | 12 | FGFR1 | imbal | 12 | 1q25 | gain | 12 | MYC | gain | 12 | 0.857 | 0.952 |
| FGFR1 | imbal | 12 | FGFR1 | loss | 12 | 1q25 | gain | 12 | MYC | gain | 12 | 0.857 | 0.952 |
| FGFR1 | imbal | 12 | FGFR1 | gain | 12 | 1q25 | gain | 12 | MYC | gain | 12 | 0.857 | 0.952 |
| FGFR1 | imbal | 12 | 1q25 | gain | 12 | MYC | gain | 12 | CEP18 | gain | 12 | 0.857 | 0.952 |
| FGFR1 | gain | 8 | 1q25 | gain | 8 | CEP18 | gain | 8 | 20q13.2 | gain | 8 | 0.837 | 0.952 |
| PTEN/CEP10 | loss | 12 | FGFR1 | loss | 12 | 1q25 | gain | 12 | MYC | gain | 12 | 0.816 | 0.952 |
| PTEN/CEP10 | loss | 12 | FGFR1 | imbal | 12 | 1q25 | gain | 12 | CEP18 | gain | 12 | 0.816 | 0.952 |
| FGFR1 | loss | 12 | 1q25 | gain | 12 | MYC | gain | 12 | CEP18 | gain | 12 | 0.816 | 0.952 |
| PTEN/CEP10 | loss | 12 | FGFR1 | gain | 12 | 1q25 | gain | 12 | MYC | gain | 12 | 0.796 | 0.952 |
| FGFR1 | gain | 28 | CEP 10 | imbal | 28 | 1q25 | gain | 28 | MYC | gain | 28 | 0.796 | 0.952 |
| PTEN/CEP10 | loss | 12 | 1q25 | gain | 12 | MYC | gain | 12 | CEP18 | gain | 12 | 0.796 | 0.952 |
| FGFR1 | gain | 12 | 1q25 | gain | 12 | MYC | gain | 12 | CEP18 | gain | 12 | 0.796 | 0.952 |
| PTEN/CEP10 | loss | 12 | 1q25 | gain | 12 | MYC | gain | 12 | 20q13.2 | gain | 12 | 0.796 | 0.952 |
| FGFR1 | gain | 12 | 1q25 | gain | 12 | MYC | gain | 12 | 20q13.2 | gain | 12 | 0.796 | 0.952 |
| 1q25 | gain | 12 | MYC | gain | 12 | CEP18 | gain | 12 | 20q13.2 | gain | 12 | 0.796 | 0.952 |

Abbreviations: Probe = locus of interest; Abn = Type of abnormality; loss = evaluates only loss of locus; gain = evaluates only gain of locus; imbal = evaluates gains or loss; cutoff = % of cells with abnormality to consider a specimen as positive.

ATTACHMENT 1. GeneSensor ™ 300 Array Clone List

| | | Cyto Loc, Locus Link | Utility |
|---|---|---|---|
| 1 | CEB108/T7 | 1p tel | Sub Tel |
| 2 | 1PTEL06 | 1p tel | Sub Tel |
| 3 | CDC2L1(p58) | 1p36 | u DEL |
| 4 | PRKCZ | 1p36.33 | u DEL |
| 5 | TP73 | 1p36.33 | u DEL/LOH |
| 6 | D1S2660 | 1p36.32 | u DEL/LOH |
| 7 | D1S214 | 1p36.31 | u DEL/LOH |
| 8 | D1S1635 | 1p36.22 | LOH |
| 9 | D1S199 | 1p36.13 | LOH |
| 10 | FGR(SRC2) | 1p36.2-p36.1 | AMP(1) |
| 11 | MYCL1(LMYC) | 1p34.3 | AMP(1) |
| 12 | D1S427, FAF1 | 1p32.3 | LOH |
| 13 | D1S500 | 1p31.1 | LOH |
| 14 | D1S418 | 1p13.1 | LOH |
| 15 | NRAS | 1p13.2 | AMP(1) |
| 16 | D1S2465, D1S3402 | 1p12 | |
| 17 | WI-5663, WI-13414 | 1q21 | |
| 18 | LAMC2 | 1q25-q31 | AMP(1) |
| 19 | PTGS2(COX2) | 1q31.1 | |
| 20 | TGFB2 | 1q41 | |
| 21 | AKT3 | 1q44 | AMP |
| 22 | SHGC-18290 | 1q tel | Sub Tel |
| 23 | 1QTEL10 | 1q tel | Sub Tel |
| 24 | U32389 | 2p tel | Sub Tel |
| 25 | 2PTEL27 | 2p tel | Sub Tel |
| 26 | MYCN(N-myc) | 2p24.1 | AMP(1) |
| 27 | MSH2, KCNK12 | 2p22.3-2p22.1 | LOH |
| 28 | REL | 2p13-p12 | AMP(1) |
| 29 | GNLY | 2p12-q11 | M |
| 30 | SGC34236 | 2q13 | M |
| 31 | BIN1 | 2q14 | pTSG |
| 32 | LRP1B | 2q21.2 | pTSG |
| 33 | TBR1 | 2q23-q37 | M |
| 34 | ITGA4 | 2q31-q32 | M |
| 35 | CASP8 | 2q33-q34 | LOH |
| 36 | ERBB4(HER-4) | 2q33.3-q34 | HER-2 homol |
| 37 | WI-6310 | 2q tel | Sub Tel |
| 38 | D2S447 | 2q tel | Sub Tel |
| 39 | 3PTEL25 | 3p tel | Sub Tel |
| 40 | 3PTEL01, CHL1 | 3p tel | Sub Tel |
| 41 | VHL | 3p25-p26 | TSG |
| 42 | RAF1 | 3p25 | AMP(1) |
| 43 | THRB | 3p24.3 | LOH |
| 44 | MLH1 | 3p21.3-p23 | Del |
| 45 | RASSF1 | 3p21.3 | pTSG |
| 46 | FHIT | 3p14.2 | pTSG |
| 47 | p44S10 | 3p14.1 | |
| 48 | D3S1274, ROBO1 | 3p12-3p13 | LOH |
| 49 | RBP1, RBP2 | 3q21-q22 | |
| 50 | TERC | 3q26 | AMP(1) |
| 51 | EIF5A2 | 3q26.2 | |
| 52 | PIK3CA | 3q26.3 | AMP(1) |
| 53 | TP63 | 3q27-q29 | TSG |
| 54 | MFI2 | 3q tel | Sub Tel |
| 55 | 3QTEL05 | 3q tel | Sub Tel |
| 56 | GS10K2/T7 | 4p tel | Sub Tel |
| 57 | SHGC4-207 | 4p tel | Sub Tel |
| 58 | D4S114 | 4p16.3 | u DEL |
| 59 | WHSC1 | 4p16.3 | u DEL |
| 60 | DDX15 | 4p15.3 | M |
| 61 | KIT | 4q11-q12 | ONC |
| 62 | PDGFRA | 4q11-q13 | AMP(1) |
| 63 | EIF4E | 4q24 (by ucsc) | AMP |
| 64 | PGRMC2 | 4q26 | |
| 65 | PDZ-GEF1 | 4q32.1 | M |
| 66 | 4QTEL11 | 4q tel | Sub Tel |
| 67 | D4S2930 | 4q tel | Sub Tel |
| 68 | C84C11/T3 | 5p tel | Sub Tel |
| 69 | D5S23 | 5p15.2 | u DEL |

ATTACHMENT 1. GeneSensor™ 300 Array Clone List

| | | Cyto Loc, Locus Link | Utility |
|---|---|---|---|
| 70 | D5S2064 | 5p15.2 | u DEL |
| 71 | DAB2 | 5p13 | pTSG |
| 72 | DHFR, MSH3 | 5q11.2-q13.2 | gain/loss Ca |
| 73 | APC | 5q21-q22 | Del |
| 74 | EGR1 | 5q31.1 | Del |
| 75 | CSF1R | 5q33-q35 | Del |
| 76 | NIB1408 | 5q tel | Sub Tel |
| 77 | 5QTEL70 | 5q tel | Sub Tel |
| 78 | 6PTEL48 | 6p tel | Sub Tel |
| 79 | PIM1 | 6p21.2 | M |
| 80 | CCND3 | 6p21 | AMP |
| 81 | D6S414 | 6p12.1-p21.1 | |
| 82 | HTR1B | 6q13 | M |
| 83 | D6S434 | 6q16.3 | Del |
| 84 | D6S268 | 6q16.3-q21 | LOH |
| 85 | MYB | 6q22-q23 | AMP(1) |
| 86 | D6S311 | 6q23-24 | LOH |
| 87 | ESR1 | 6q25.1 | AMP(1) |
| 88 | 6QTEL54 | 6q tel | Sub Tel |
| 89 | G31341 | 7p tel | Sub Tel |
| 90 | IL6 | 7p21 | M |
| 91 | EGFR | 7p12.3-p12.1 | AMP(1) |
| 92 | ELN | 7q11.23 | u DEL |
| 93 | RFC2, CYLN2 | 7q11.23 | u DEL |
| 94 | ABCB1(MDR1) | 7q21.1 | AMP(1) |
| 95 | CDK6 | 7q21-q22 | AMP |
| 96 | SERPINE1 | 7q21.3-q22 | pTSG |
| 97 | MET | 7q31 | AMP(1) |
| 98 | TIF1 | 7q32-q34 | M |
| 99 | stSG48460 | 7q tel | Sub Tel |
| 100 | 7QTEL20 | 7q tel | Sub Tel |
| 101 | D8S504 | 8p tel | Sub Tel |
| 102 | D8S596 | 8p tel | Sub Tel |
| 103 | CTSB | 8p22 | AMP(1) |
| 104 | PDGRL | 8p22-p1.3 | Del |
| 105 | LPL | 8p22 | Del |
| 106 | FGFR1 | 8p11.2-p11.1 | AMP(1) |
| 107 | MOS | 8q11 | AMP(1) |
| 108 | E2F5 | 8p22-q21.3 | M |
| 109 | EXT1 | 8q24.11-q24.13 | TSG, uDel |
| 110 | MYC | 8q24.12-q24.13 | AMP(1) |
| 111 | PTK2 | 8q24-qter | AMP |
| 112 | SHGC-31110 | 8q tel | Sub Tel |
| 113 | U11829 | 8q tel | Sub Tel |
| 114 | AF170276 | 9p tel | Sub Tel |
| 115 | D9S913 | 9ptel | Sub Tel |
| 116 | MTAP | 9p21.3 | LOH |
| 117 | CDKN2A(p16), MTAP | 9p21 | TSG |
| 118 | AFM137XA11 | 9p11.2 | M |
| 119 | D9S166 | 9p12-q21 | |
| 120 | PTCH | 9q22.3 | TSG |
| 121 | DBCCR1 | 9q33.2 | TSG |
| 122 | TSC1 | 9q34 | TSG |
| 123 | ABL1 | 9q34.1 | AMP(1) |
| 124 | H18962 | 9q tel | Sub Tel |
| 125 | D9S325 | 9q tel | Sub Tel |
| 126 | 10PTEL006 | 10p tel | Sub Tel |
| 127 | SHGC-44253 | 10p tel | Sub Tel |
| 128 | D10S249, D10S533 | 10p15 | TSG |
| 129 | GATA3 | 10p15 | |
| 130 | WI-2389, D10S1260 | 10p14-p13 | u DEL |
| 131 | BMI1 | 10p13 | gain |
| 132 | D10S167 | 10p11-10q11 | near Cen |
| 133 | EGR2 | 10q21.3 | M |
| 134 | PTEN | 10q23.3 | TSG |
| 135 | FGFR2 | 10q26 | AMP(1) |
| 136 | DMBT1 | 10q25.3-q26.1 | |
| 137 | stSG27915 | 10q tel | Sub Tel |
| 138 | 10QTEL24 | 10q tel | Sub Tel |
| 139 | 11PTEL03 | 11p tel | Sub Tel |
| 140 | INS | 11p tel | Sub Tel |
| 141 | HRAS | 11p15.5 | AMP(1) |
| 142 | CDKN1C(p57) | 11p15.5 | TSG |
| 143 | WT1 | 11p13 | TSG |
| 144 | KAI1 | 11p11.2 | |
| 145 | D11S461 | 11q12.2 | near cen |
| 146 | MEN1 | 11q13 | |
| 147 | CCND1 | 11q13 | AMP(1) |
| 148 | FGF4, FGF3 | 11q13 | AMP(1) |
| 149 | EMS1 | 11q13 | AMP(1) |
| 150 | GARP | 11q13.5-q14 | AMP(1) |
| 151 | PAK1 | 11q13-q14 | AMP(1) |
| 152 | RDX | 11q22.3 | LOH |
| 153 | ATM | 11q22.3 | LOH |
| 154 | MLL | 11q23 | AMP(1) |
| 155 | WI-6509 | 11q tel | Sub Tel |
| 156 | AF240622 | 11q tel | Sub Tel |
| 157 | 8M16/SP6 | 12p tel | Sub Tel |
| 158 | SHGC-5557 | 12p tel | Sub Tel |
| 159 | CCND2 | 12p13 | AMP(1) |
| 160 | CDKN1B(p27) | 12p13.1-p12 | TSG |
| 161 | KRAS2 | 12p11.2 | AMP(1) |
| 162 | WNT1(INT1) | 12q12-q13 | AMP(1) |
| 163 | CDK2, ERBB3 | 12q13 | AMP |
| 164 | GLI | 12q13.2-q13.3 | AMP(1) |
| 165 | SAS, CDK4 | 12q13-q14 | AMP(1) |
| 166 | MDM2 | 12q14.3-q15 | AMP(1) |
| 167 | DRIM, ARL1 | 12q23 | |
| 168 | stSG8935 | 12q tel | Sub Tel |
| 169 | U11838 | 12q tel | Sub Tel |
| 170 | BRCA2 | 13q12-q13 | TSG |
| 171 | RB1 | 13q14 | TSG |
| 172 | D13S319 | 13q14.2 | LOH |
| 173 | D13S25 | 13q14.3 | LOH |
| 174 | D13S327 | 13q tel | Sub Tel |
| 175 | PNN(DRS) | 14q13 | |
| 176 | TCL1A | 14q32.1 | gain/loss |
| 177 | AKT1 | 14q32.32 | AMP(1) |
| 178 | IGH(D14S308) | 14q tel | Sub Tel |
| 179 | IGH(SHGC-36156) | 14q tel | Sub Tel |
| 180 | D15S11 | 15q11-q13 | u DEL |
| 181 | SNRPN | 15q12 | u DEL |
| 182 | UBE3A, D15S10 | 15q11-q13 | u DEL |
| 183 | GABRB3 | 15q11.2-q12 | u DEL |
| 184 | MAP2K5 | 15q23 | |
| 185 | FES | 15q26.1 | AMP(1) |
| 186 | IGF1R | 15q25-q26 | AMP(1) |
| 187 | PACE4C | 15q tel | Sub Tel |
| 188 | WI-5214 | 15q tel | Sub Tel |
| 189 | 16PTEL03 | 16p tel | Sub Tel |
| 190 | stSG48414 | 16p tel | Sub Tel |
| 191 | CREBBP | 16p13.3 | u DEL |
| 192 | EMP2 | 16p13.3 | |
| 193 | ABCC1(MRP1) | 16p13.1 | AMP(1) |
| 194 | CYLD | 16q12-q13 | TSG |
| 195 | CDH1 | 16q22.1 | LOH |
| 196 | FRA16D | 16q23.2 | |
| 197 | CDH13 | 16q24.2-q24.3 | LOH |
| 198 | LZ16 | 16q24.2 | Del |
| 199 | FANCA | 16q24.3 | |
| 200 | stSG30213 | 16q tel | Sub Tel |
| 201 | 16QTEL013 | 16q tel | Sub Tel |
| 202 | 282M15/SP6 | 17p tel | Sub Tel |
| 203 | WI-14673 | 17p tel | Sub Tel |
| 204 | HIC1 | 17p13.3 | LOH |
| 205 | D17S379, MNT | 17p13.3 | u DEL/LOH |
| 206 | PAFAH1B1(LIS1) | 17p13.3 | u DEL |
| 207 | TP53(p53) | 17p13.1 | TSG |
| 208 | D17S125, D17S61 | 17p12-p11.2 | u Del/u Dup |
| 209 | D17S1296, D17S1523 | 17p12-p11.2 | u Del/u Dup |
| 210 | LLGL1 | 17p12-17p11.2 | u DEL |
| 211 | FLI, TOP3A | 17p12-17p11.2 | u DEL |
| 212 | NF1 5' | 17q11.2 | |
| 213 | NF1 3' | 17q11.2 | |
| 214 | BRCA1 | 17q21 | TSG |
| 215 | PPARBP(PBP) | 17q12 | AMP |
| 216 | ERBB2(HER-2) | 17q11.2-17q12 | AMP(1) |
| 217 | THRA | 17q11.2 | AMP |

ATTACHMENT 1. GeneSensor™ 300 Array Clone List

| | | Cyto Loc, Locus Link | Utility |
|---|---|---|---|
| 218 | TOP2A | 17q21-q22 | AMP |
| 219 | NME1(NME23) | 17q21.3 | LOH? |
| 220 | RPS6KB1(STK14A) | 17q23 | AMP(1) |
| 221 | D17S1670 | 17q23 | |
| 222 | TK1 | 17q23.2-q25.3 | AMP? |
| 223 | SHGC-103396 | 17q tel | Sub Tel |
| 224 | AFM217YD10 | 17q tel | Sub Tel |
| 225 | D18S552 | 18p tel | Sub Tel |
| 226 | SHGC17327 | 18p tel | Sub Tel |
| 227 | YES1 | 18p11.31-p11.21 | AMP(1) |
| 228 | TYMS(TS) | 18p11.32 | AMP |
| 229 | LAMA3 | 18q11.2 | |
| 230 | FRA18A(D18S978) | 18q12.3 | |
| 231 | DCC | 18q21.3 | Del |
| 232 | MADH4(DPC4) | 18q21.1 | TSG |
| 233 | BCL2 3' | 18q21.3 | AMP |
| 234 | CTDP1, SHGC-145820 | 18q tel | Sub Tel |
| 235 | 18QTEL11 | 18q tel | Sub Tel |
| 236 | 129F16/SP6 | 19p tel | Sub Tel |
| 237 | stSG42796 | 19p tel | Sub Tel |
| 238 | INSR | 19p13.2 | AMP(1) |
| 239 | JUNB | 19p13.2 | AMP(1) |
| 240 | CCNE1 | 19q12 | AMP(1) |
| 241 | AKT2 | 19q13.1-q13.2 | LOH |
| 242 | GLTSCR2, SULT2A1 | 19q13.32 | |
| 243 | D19S238E | 19 q tel | Sub Tel |
| 244 | 20PTEL18 | 20p tel | Sub Tel |
| 245 | SOX22 | 20p tel | Sub Tel |
| 246 | JAG1 | 20p12.1-p11.23 | uDel |
| 247 | MKKS, SHGC-79896 | 20p12.1-p11.23 | uDel |
| 248 | TOP1 | 20q12-q13.1 | AMP(1) |
| 249 | NCOA3(AIB1) | 20q12 | AMP(1) |
| 250 | MYBL2 | 20q13.1 | AMP(1) |
| 251 | CSE1L(CAS) | 20q13 | AMP(1) |
| 252 | PTPN1 | 20q13.1-q13.2 | AMP(1) |
| 253 | STK6(STK15) | 20q13.2-q13.3 | AMP(1) |
| 254 | ZNF217(ZABC1) | 20q13.2 | AMP(1) |
| 255 | CYP24 | 20q13.2 | AMP |
| 256 | TNFRSF6B(DCR3) | 20q13 | AMP |
| 257 | TPD52L2, TOM | 20q tel | Sub Tel |
| 258 | 20QTEL14 | 20q tel | Sub Tel |
| 259 | D21S378 | 21q11.2 | M |
| 260 | RUNX1(AML1) | 21q22.3 | AMP(1) |
| 261 | DYRK1A | 21q22 | gain |
| 262 | D21S341, D21S342 | 21q22.3 | gain |
| 263 | PCNT2(KEN) | 21q tel | Sub Tel |
| 264 | 21QTEL08 | 21q tel | Sub Tel |
| 265 | D22S543 | 22q11 | M |
| 266 | GSCL | 22q11.21 | u DEL |
| 267 | HIRA(TUPLE1) | 22q11.21 | u DEL |
| 268 | TBX1 | 22q11.2 | u DEL |
| 269 | BCR | 22q11.23 | AMP(1) |
| 270 | NF2 | 22q12.2 | TSG |
| 271 | PDGFB(SIS) | 22q13.1 | AMP(1) |
| 272 | ARHGAP8 | 22q13.3 | |
| 273 | ARSA | 22q tel | Sub Tel |
| 274 | 22QTEL31 | 22q tel | Sub Tel |
| 275 | DXYS129 | X/Yp tel | Sub Tel |
| 276 | STS 3' | Xp22.3 | u DEL |
| 277 | STS 5' | Xp22.3 | u DEL |
| 278 | KAL | Xp22.3 | u DEL |
| 279 | DMD exon 45-51 | Xp21.1 | |
| 280 | DXS580 | Xp11.2 | |
| 281 | DXS7132 | Xq12 | |
| 282 | AR 3' | Xq11-q12 | AMP(1) |
| 283 | XIST | Xq13.2 | |
| 284 | OCRL1 | Xq25 | |
| 285 | EST CDY16c07 | X/Yq tel | Sub Tel |
| 286 | SRY | Yp11.3 | |
| 287 | AZFa region | Yq11 | |

Sub Tel Single copy sequence near the telomere
AMP(1) Cancer Amplicon previously placed on AmpliOncl Chip
AMP Cancer Amplicon not previously placed on AmpliOncl Chip
u DEL Region lost in microdeletion syndrome
TSG Tumor Supressor Gene
pTSG putqtive Tumor Supressor Gene
M Marker added to reduce genomic gaps
gain Region gained in cancer
u Dup Micro Duplication
LOH Region of Loss of Heterozygosity
Del Deletion Region near
Cen Single copy sequence near the centromere

What is claimed is:

1. A hybridization method comprising:
   contacting a biological sample from a subject with a set of detectably labeled or substrate-immobilized nucleic acid probes, the set consisting of:
   a) a probe for 1q24;
   b) a probe for the centromeric region of chromosome 18;
   c) a probe for 2q26; and
   d) a probe for 20q13;
   incubating the probes of the set with the sample under conditions in which each probe selectively hybridizes with a polynucleotide sequence in its target chromosomal region to form a stable hybridization complex; and
   detecting hybridization of the set of probes to determine a hybridization pattern.

2. The method of claim 1, wherein the hybridization pattern shows a gain in one or more chromosome regions selected from the group consisting of 1q24, CEP18, 2q26, or 20q13.

3. The method of claim 1, wherein the hybridization pattern shows a loss in one or more chromosome regions selected from the group consisting of 1q24, CEDP18, 2q26, or 20q13.

4. The method of claim 1, wherein the method is carried out by array comparative genomic hybridization (aCGH) to substrate-immobilized probes.

5. The method of claim 1, wherein the method is carried out by fluorescence in situ hybridization, and each probe in the set is labeled with a different fluorophore.

6. The method of claim 1, wherein the sample comprises an endometrial brushing specimen or an endometrial biopsy specimen.

* * * * *